(12) United States Patent
Seshi

(10) Patent No.: US 7,049,072 B2
(45) Date of Patent: May 23, 2006

(54) GENE EXPRESSION ANALYSIS OF PLURI-DIFFERENTIATED MESENCHYMAL PROGENITOR CELLS AND METHODS FOR DIAGNOSING A LEUKEMIC DISEASE STATE

(75) Inventor: Beerelli Seshi, Torrance, CA (US)

(73) Assignee: University of South Florida, Tampa (*) Notice: Subject to any disclaimer, the term of this patent is extended or adjusted under 35 U.S.C. 154(b) by 0 days.

(21) Appl. No.: 10/263,419

(22) Filed: Oct. 3, 2002

(65) Prior Publication Data

US 2003/0203483 A1    Oct. 30, 2003

Related U.S. Application Data

(63) Continuation-in-part of application No. 09/914,508, filed as application No. PCT/US01/16408 on May 21, 2001, which is a continuation-in-part of application No. 09/862,231, filed on May 21, 2001.

(60) Provisional application No. 60/412,450, filed on Sep. 20, 2002, provisional application No. 60/352,636, filed on Jan. 28, 2002, provisional application No. 60/334,277, filed on Nov. 28, 2001, provisional application No. 60/327,140, filed on Oct. 3, 2001, provisional application No. 60/277,700, filed on Mar. 21, 2001, provisional application No. 60/209,245, filed on Jun. 5, 2000.

(51) Int. Cl.
  *C12Q 1/68*   (2006.01)
  *C12P 19/34*  (2006.01)
  *C07H 21/02*  (2006.01)
  *C07H 21/04*  (2006.01)

(52) U.S. Cl. ............ 435/6; 435/7.2; 435/91.2; 435/372; 435/372.1; 536/23.5

(58) Field of Classification Search ............... 435/6, 435/91.2, 7.2, 372, 372.1
  See application file for complete search history.

(56) References Cited

U.S. PATENT DOCUMENTS

| | | |
|---|---|---|
| 5,486,359 A | 1/1996 | Caplan et al. |
| 5,521,067 A | 5/1996 | Seshi |
| 5,733,542 A | 3/1998 | Haynesworth et al. |
| 5,879,940 A | 3/1999 | Torok-Storb et al. |
| 5,942,225 A | 8/1999 | Bruder et al. |
| 6,010,696 A | 1/2000 | Caplan et al. |
| 2003/0003084 A1 | 1/2003 | Seshi |

FOREIGN PATENT DOCUMENTS

| | | |
|---|---|---|
| WO | WO 01/94541 A2 | 12/2001 |
| WO | WO 03/029432 A2 | 4/2003 |

OTHER PUBLICATIONS

Lazarus, H.M. et al. "Human bone marrow-derived mesenchymal (stromal) progenitor cells (MPCs) cannot be recovered from peripheral blood progenitor cell collections" *J. Hemotherapy*, 1997, 6:447-455.

Simmons, P.J. et al. "Isolation, characterization and functional activity of human marrow stromal progenitors in hemopoiesis" *Advances in Bone Marrow Purging and Processing*, 1994, 389:271-280.

Sullivan, A.K. et al. "Cellular composition of rat bone marrow stroma" *Lab. Invest.*, 1989, 60(4):667-676.

Chakrabarti, O. and S. Krishna "Molecular interactions of 'high risk' human papillomaviruses E6 and E7 oncoproteins: implications for tumour progression" *J. Biosci.*, 2003, 28(3):337-348.

Charbord, P. et al. "Stromal cells from human long-term marrow cultures, but not cultured marrow fibroblasts, phagocytose horse serum constituents: studies with a monoclonal antibody that reacts with a species-specific epitope common to multiple horse serum proteins" *Exp. Hematol.*, 1987, 15:72-77.

Conget, P.A. and J.J. Minguell "Phenotypical and functional properties of human bone marrow mesenchymal progenitor cells" *J. Cell. Physiol.*, Oct. 1999, 181:67-73.

Dennis, J.E. et al. "A quadripotential mesenchymal progenitor cell isolated from the marrow of an adult mouse" *J. Bone and Mineral Res.*, 1999, 14(5):700-709.

Deunsing, S. and K. Munger "The human papillomavirus type 16 E6 and E7 oncoproteins independently induce numerical and structural chromosome instability" *Cancer Res.*, 2002, 62:7075-7082.

Deunsing, S. et al. "The human papillomavirus type 16 E6 and E7 oncoproteins cooperate to induce mitotic defects and genomic instability by uncoupling centrosome duplication from the cell division cycle" *PNAS*, 2000, 97(18):10002-10007.

Dorshkind, K. "Multilineage development from adult bone marrow cells" *Nature Immunology*, 2002, 3(4):311-313.

Durst, M. et al. "Inverse relationship between human papillomavirus (HPV) type 16 early gene expression and cell differentiation in nude mouse epithelial cysts and tumors induced by HPV-positive human cell lines" *J. Virology*, 1991, 65(2):796-804.

Friedenstein, A.J. et al. "Fibroblast precursors in normal and irradiated mouse hematopietic organs" *Exp Hemat.*, 1976, 4:267-274.

(Continued)

*Primary Examiner*—Carla J. Myers
(74) *Attorney, Agent, or Firm*—Saliwanchik, Lloyd & Saliwanchik

(57) ABSTRACT

Pluri-differentiated human mesenchymal progenitor cells (MPCs) are isolated. A method isolates and purifies human mesenchymal progenitor cells from Dexter-type cultures for characterization of and uses, particularly therapeutic uses for such cells. Specifically, isolated MPCs can be used for diagnostic purposes, to enhance the engraftment of hematopoietic progenitor cells, enhance bone marrow transplantation, or aid in the treatment or prevention of graft versus host disease.

65 Claims, 19 Drawing Sheets

OTHER PUBLICATIONS

Eaves, A.C. and C.J. Eaves "Maintenance and proliferation control of primitive hemopoietic progenitors in long-term cultures of human marrow cells" *Blood Cells*, 1988, 14:355-368.

Gerson, S.L. "Mesenchymal-stem cells: No longer second class marrow citizens" *Nature Med.*, 1999, 5(3):262-264.

Graf, L. et al. "Gene expression profiling of the functionally distinct human bone marrow stromal cell lines HS-5 and HS-27a" *Blood*, 2002, 100(4):1509-1511.

Gravitt, P. "HPV: The ultimate cancer initiator?" *HPV Today*, No. 3, Sep. 2003, pp. 1-4.

Haynesworth, S.E. et al. "Characterization of cells with osteogenic potential from human marrow" *Bone*, 1992, 13:81-88.

Haynesworth, S.E. et al. "Cell surface antigens on human marrow-derived mesenchymal cells are detected by monoclonal antibodies" *Bone*, 1992, 13:69-80.

Henderson, A.J. et al. "Functional characterization of two stromal cell lines that support B lymphopoiesis" *J. Immunology*, 1990, 145:423-428.

Hicok, K.C. et al. "Development and characterization of conditionally immortalized osteoblast precursor cell lines from human bone marrow stroma" *J. Bone and Mineral Res.*, 1998, 13(2):205-217.

Horwitz, E.M. et al. "Transplantability and therapeutic effects of bone marrow-derived mesenchymal cells in children with osteogenesis imperfecta" *Nature Med.*, 1999, 5(3):309-313.

Iwata, M. et al. "Functional interleukin-7 receptors (IL7R) are expressed by marrow stromal cells: binding of IL-7 increases levels of IL-6 mRNA and secreted protein" Aug. 2002 (epub date May 2002), 100:1318-1325.

Keating, A. et al. "Donor origin of the in vitro haematopoletic microenvironment after marrow transplantation in man" *Nature*, 1982, 298:280-283.

Kelly, K.A. and J.M. Gimble "1,25-Dihydroxy vitamin $D_3$ inhibits adipocyte differentiation and gene expression in murine bone marrow stromal cell clones and primary cultures" *Endocrinology*, 1998, 139:2622-2628.

Koç, O.N. et al. "Bone marrow-derived mesenchymal stem cells remain host-derived despite successful hematopoietic engraftment after allogeneic transplantation in patients with lysosomal and peroxisomal storage diseases" *Exp. Hematology*, 1999, 27:1675-1681.

Kopen, G.C. et al. "Marrow stromal cells migrate throughout forebrain and cerebellum, and they differentiate into astrocytes after injection into neonatal mouse brains" *Proc. Natl. Acad. Sci. USA*, 1999, 96:10711-10716.

Liesveld, J.L. et al. "Characterization of human marrow stromal cells: Role in progenitor cell binding and granulopoiesis" *Blood*, 1989, 73(7):1794-1800.

Moore, M.A.S. et al. "Prolonged hematopoiesis in a primate bone marrow culture system: Characteristics of stem cell production and the hematopoietic microenvironment" *Blood*, 1979, 54(4):775-793.

Park, S.R. et al. "Interconversion potential of cloned human marrow adipocytes in vitro" *Bone*, 1999, 24(6):549-554.

Penn, P.E. et al. "Dissecting the hematopoietic microenvironment. IX. Further characterization of murine bone marrow stromal cells" *Blood*, 1993, 81(5):1205-1213.

Pessina, A. et al. "Expression of B cell markers on SR-4987 cells derived from murine bone marrow stroma" *Exp. Hematology*, 1997, 25:536-541.

Prockop, D.J. "Marrow stromal cells as stem cells for nonhematopoietic tissues" *Science*, 1997, 276:71-74.

Roecklein, B.A. and B. Torok-Storb "Functionally distinct human marrow stromal cell lines immortalized by transduction with the human papilloma virus E6/E7 genes" *Blood*, 1995, 85(4):997-1005.

Seshi, B. et al. "Multilineage gene expression in human bone marrow stromal cells as eveidenced by single-cell microarray analysis" *Blood Cells, Molecules, and Diseases*, 2003, 31:268-285.

Siler, U. et al. "Laminin γ2 chain as a stromal cell marker of the human bone marrow microenvironment" *Brit. J. Haematology*, 2002, 119:212-220.

Simmons, P.J. et al. "Host origin of marrow stromal cells following allogeneic bone marrow transplantation" *Nature*, 1987, 328:429-432.

Singer, J.W. et al. "Evidence for a stem cell common to hematopolesis and its in vitro microenvironment: Studies of patients with clonal hematopoietic neoplasia" *Leukemia Res.*, 1985, 8(4):535-545.

Stedman, T.L., Stedman's Medical Dictionary, 5th Edition, 1984, pp. 931-932.

Stoppler, H. et al. "The human papillomavirus type 16 E6 and E7 oncoproteins dissociate cellular telomerase activity from the maintenance of telomere length" *J. Biol. Chem.*, 1997, 272(20):13332-13337.

Taichman, R.S. et al. "Human osteoblasts support human hematopoietic progenitor cells in in vitro bone marrow cultures" *Blood*, 1996, 87(2):518-524.

Torok-Storb, B., ATCC Catalog, ATCC No. CRL-2496.

Torok-Storb, B. et al. "Dissecting the marrow microenvironment" *Ann. NY Acad. Sci.*, 1999, 872:164-170.

Taichman, R.S. and S.G. Emerson "Human osteoblasts support hematopoiesis through the production of granulocyte colony-stimulating factor" *J. Exp. Med.*, 1994, 179:1677-1682.

Terada, N. et al. "Bone marrow cells adopt the phenotype of other cells by spontaneous cell fusion" *Nature*, 2002, 416:542-545.

Thomas, T. et al. "Leptin acts on human marrow stromal cells to enhance differentiation to osteoblasts and to inhibit differentiation to adipocytes" *Endocrinology*, 1999, 140:1630-1638.

Tremain, N. et al. "MicroSAGE analysis of 2,353 expressed genes in a single cell-derived colony of undifferentiated human mesenchymal stem cells reveals mRNAs of multiple cell lineages" *Stem Cells*, 2001, 19:408-418.

Wineman, J. et al. "Functional heterogeneity of the hematopoietic microenvironment: Rare Stromal elements maintain long-term repopulating stem cells" *Blood*, 1996, 87(10):4082-4090.

Woodbury, D. et al. "Adult bone marrow stromal stem cells express germline, ectodermal, endodermal, and mesodermal genes prior to neurogenesis" *J. Neuroscience Res.*, 2002, 96:908-917.

Yamazaki, K. et al. "A comparative morphometric study on the ultrastructure of adherent cells in long-term bone marrow culture from normal and congenitally anemic mice" *Blood Cells*, 1989, 15:343-364.

Seshi, B. "Proteomics knocks on hematology's door" *Blood*, May 2004, 103(10):3607.

Ager, A. et al. Immune Receptor Supplement, 2nd edition, *Immunology Today*, Oct. 1997, pp. 1-35.

Bordignon, C. et al. "Cell Therapy: Achievements and Perspectives" *Haematologica*, 1999, 84:1110-1149.

Dexter, T.M. et al. "Long-Term Marrow Culture: An Overview of Techniques and Experience" in Long-Term Bone Marrow Culture, Wright, D.G. et al., Eds., 1984, pp. 57-96.

Dexter, T.M. et al. "Condition Controlling the Proliferation of Haemopoietic Stem Cells in Vitro" *J. Cell. Physiol.*, 1977, 91(3):335-344.

Gartner, s. and H.S. Kaplan "Long-term culture of human bone marrow cells" *Proc. Natl. Acad. Sci. USA*, 1980, 77(8):4756-4759.

Greenberger, J.S. "Sensitivity of corticosteroid-dependent insulin-resistant lipogenesis in marrow preadipocytes of obese-diabetic (db/db) mice" *Nature*, Oct. 26, 1978, 275:752-754.

Keating, A. et al. "Effect of Different Promoters on Expression of Genes Introduced into Hematopoietic and Marrow Stromal Cells by Electroporation" *Exp. Hematol.*, 1990, 18:99-102.

Majumdar et al. "Phenotypic and Functional Comparison of Cultures of Marrow-Derived Mesenchymal Cells (MSCs) and Stromal Cells" *J. Cell. Physiol.*, 1998, 176:57-66.

Marini, F. et al. "Mesenchymal Stem Cells (MSC) from Patients with Chronic MyeLogenous Leukemia (CML) Patients can be Transduced with Common Gene Transfer Vectors at High Efficiency, and are Genotypically Normal" Abstract from American Society of Hematology 42nd Annual Meeting, Part 1. Dec. 1-5, 2000. San Francisco, Ca.

Pittenger, M.F. et al. "Multilineage Potential of Adult Human Mesenchymal Stem Cells" *Science*, 1999, 284:143-147.

Seshi, B. "Discovery of Novel Hematopoietic Cell Adhesion Molecules From Human Bone Marrow Stromal Cell Membrane Protein Extracts by a New Cell-Blotting Technique" *Blood*, May 1994, 83(9):2399-2409.

Seshi, B. et al. "Human Bone Marrow Stromal Cell: Coexpression of Markers Specific for Multiple Mesenchymal Cell Lineages" *Blood Cells, Molecules, and Diseases*, Jun. 2000, 26(3):234-246.

Seshi, B. et al. "Multilineage gene expression in human bone marrow stromal cells as evidenced by single-cell microarray analysis" *Blood Cells, Molecules, and Diseases*, 2003, 31:268-285.

Affymetrix reference guide, Statistical Algorithms Description Document, 2002.

Choi, Y. et al. "A workshop on the marrow microenvironment and hematological malignancy" *Can. Res.*, 2003, 63:7539-7541.

Eisen, M. et al. "Cluster analysis and display of genome-wide expression patterns" *Proc. Natl. Acad. Sci. USA*, 1998, 95:14863-14868.

Glanzer, J.G. and Eberwine, J.H. "Expression profiling of small cellular samples in cancer: less is more" *Brit. J. Canc.*, 2004, 90:1111-1114.

Seshi, B. et al. "Common Progenitor for nonhematopoietic mesenchymal cells and bone marrow derived (B) lymphocytes as evidenced by single-cell microarray analysis of isolated bone marrow stromal cells" abstract No. 550748, presented at American Society of Hematology (ASH) workshop, Sep. 23-25, 2002 and 44th Annual ASH Meeting Dec. 6-10, 2002.

Taylor, T. et al. "Microgenomics: Identification of new expression profiles via small and single-cell sample analyses" *Cytometry Part A*, 2004, 59A:254-261.

Vasseur, S. et al. "Gene expression profiling by DNA microarray analysis in mouse embryonic fibroblasts transformed by $ras^{v12}$ mutated protein and the EIA oncogene" *Molecular Cancer*, 2003, 2:19.

Collective MPCs
(Samples 1-5)
Single cell MPCs
(Samples 6-15)
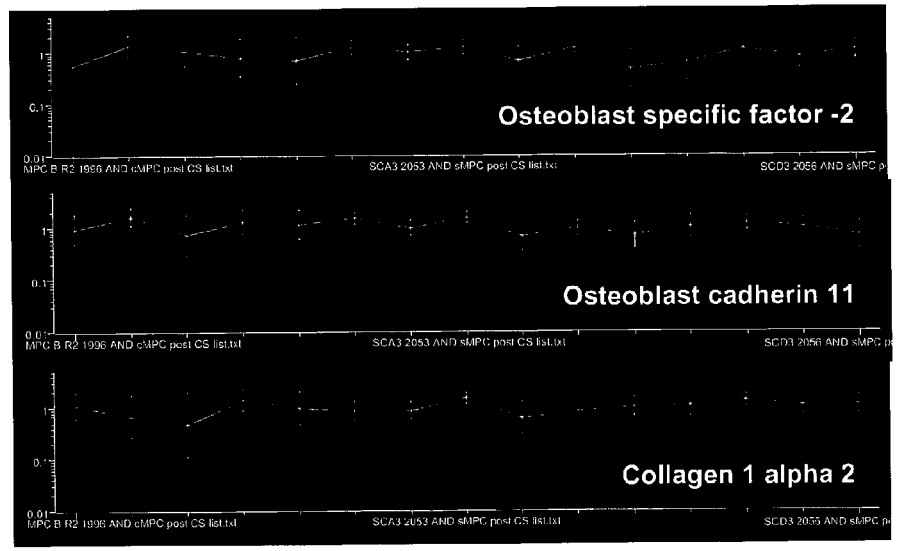
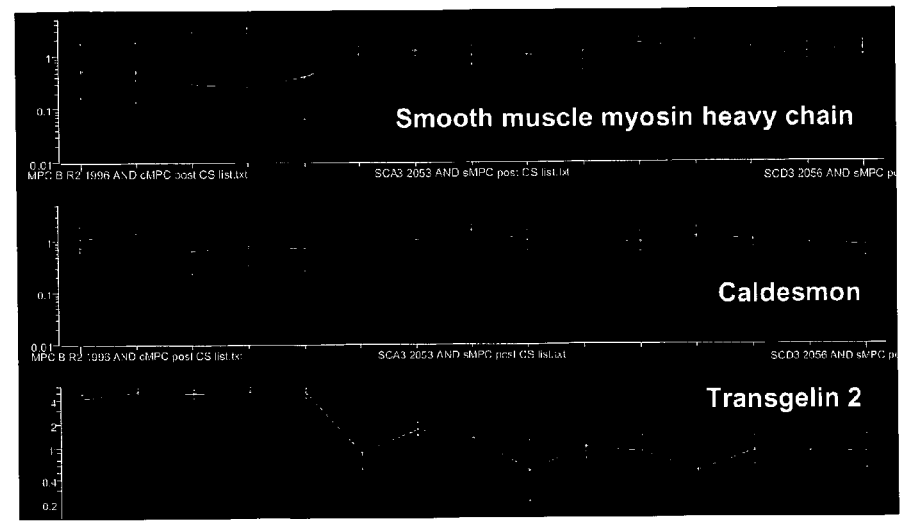
FIG - 19

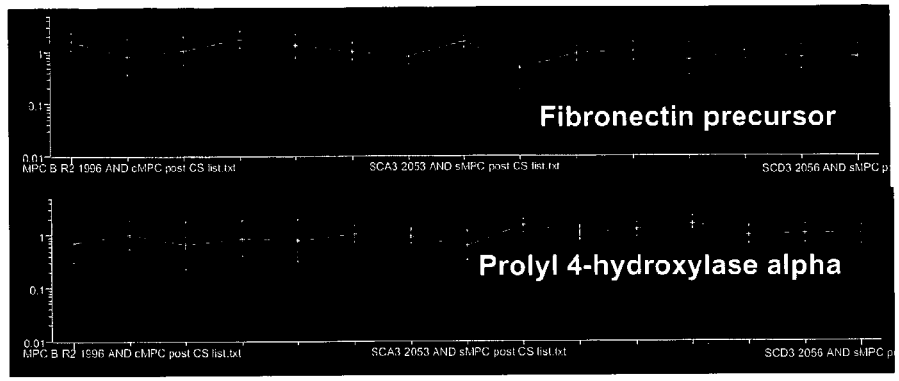
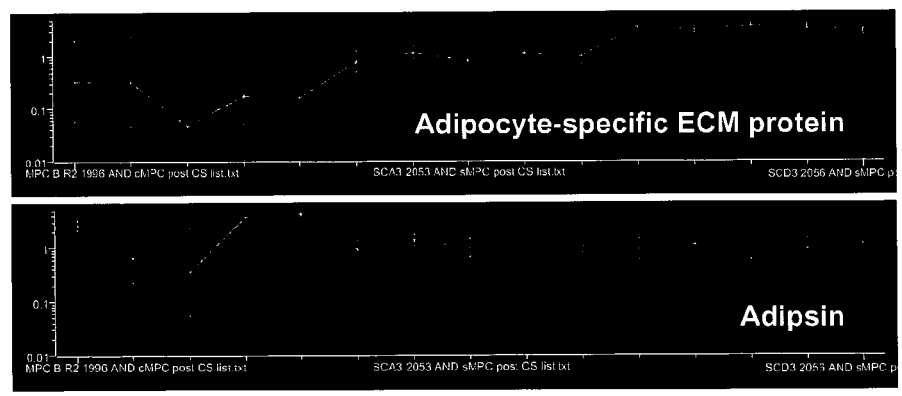
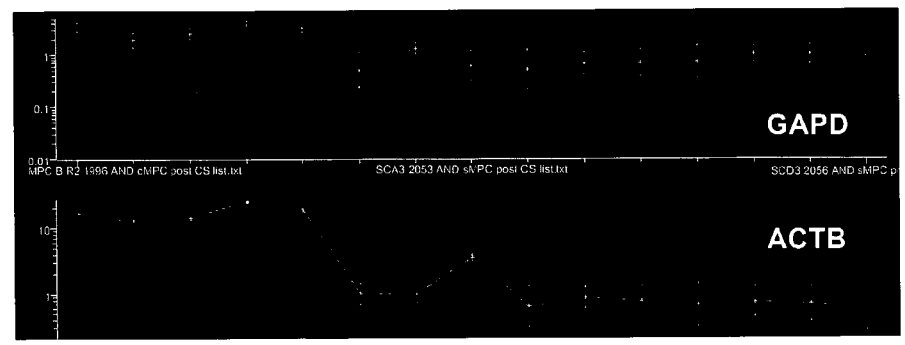
FIG-20

GENE EXPRESSION ANALYSIS OF PLURI-DIFFERENTIATED MESENCHYMAL PROGENITOR CELLS AND METHODS FOR DIAGNOSING A LEUKEMIC DISEASE STATE

CROSS-REFERENCE TO RELATED APPLICATIONS

The present application claims benefit of priority under 35 U.S.C. 119(e) of U.S. Provisional Application Ser. Nos. 60/327,140, filed Oct. 3, 2001, 60/334,277, filed Nov. 28, 2001, 60/352,636, filed Jan. 28, 2002, and 60/412,450, filed Sep. 20, 2002, and is a Continuation in Part application of U.S. Ser. No. 09/914,508, filed Nov. 7, 2001, which is a National Phase Concerning a Filing Under 35 U.S.C 371, claiming the benefit of priority of PCT/US01/16408, filed May 21, 2001, which claims the benefit of priority of U.S. Provisional Ser. Nos. 60/277,700, filed Mar. 21, 2001, and 60/209,245, filed Jun. 5, 2000, and which is a CIP of U.S. patent application Ser. No. 09/862,231, filed May 21, 2001, all of which are incorporated herein by reference.

GRANT INFORMATION

National Heart Lung Blood Institute (NHLBI) and National Institute of Health (NIH). Grant No. HL59683.

CROSS-REFERENCE TO CD-ROM APPENDIX

Attached hereto are two copies of a compact disk, each containing the file "2755 Master Stromal Cell Ge," created on Oct. 3, 2002, the file size of which is 499 kilobytes, the contents of which are herein incorporated by reference. The total number of compact disks including duplicates is two.

FIELD OF THE INVENTION

The present invention generally relates to pluri-differentiated mesenchymal progenitor cells and therapeutic uses for the same. More specifically, the isolated mesenchymal progenitor cells are isolated from hematopoietic cells and macrophages in Dexter-type cultures cells.

BACKGROUND OF THE INVENTION

Bone marrow, the site of blood cell production and home to various leukemia and lymphoma cells, comprises a complex cellular population including hematopoietic progenitor or stem cells and the stromal cells that support them. Hematopoietic stem cells have the capacity for self-regeneration and for generating all blood cell lineages while stromal stem cells have the capacity for self-renewal and for producing the hematopoietic microenvironment.

Two bone-marrow culture systems introduced in the mid-1970's have evolved as favored media for the in vitro analysis of mesengenesis and hematopoiesis. The Friedenstein culture system was introduced in 1976 as a media for the analysis and study of mesengenesis. (Friedenstein, et al, in *Exp Hematol* 4, 267–74 (1976). In is necessary to first isolate rare pluripotant mesenchymal stem cells from other cells in the bone marrow. In the Friedenstein culture system, isolating the nonhematopoietic cells is achieved by utilizing their tendency to adhere to plastic. Once isolated, a monolayer of homogeneous, undifferentiated stromal cells is then grown in the culture medium, in the absence of hematopoietic cells. The stromal cells from this system have the potential to differentiate into discrete mesenchymal tissues, namely bone, cartilage, adipose tissue and muscle depending on specific growth supplements. These MSCs have been the target of extensive investigation including exploration of their potential clinical utility in repair or replacement of genetically damaged mesenchymal tissues.

In 1977, Dexter, et al. developed another bone marrow culture system for the study of hematopoiesis. (Dexter et al. *J Cell Physiol* 91, 335–44 (1977). The Dexter culture does not require isolation of the mesenchymal cells before culturing. Thus, the monolayer of stromal cells is grown in the presence of hematopoietic cells. Greenberger later modified the Dexter system by the addition of hydrocortisone to the culture medium, making it more reproducible (Greenberger, *Nature* 275, 752–4 (1978).

Based on the Dexter system's ability to support sustained growth and preservation of hematopoietic progenitor cells, it has become the standard in vitro model for the study of hematopoiesis. Although the Dexter-type stromal cells and the MSCs in Friedenstein-type cultures express similar cytokine/growth factor profiles, the Dexter cultures have been found to be more efficient at maintaining preservation of hematopoietic progenitor cells. Over the last 23 years, questions have remained as to whether the cells from the Dexter cultures retained the potential to differentiate, like the MSCs in the Friedenstein culture, or whether they have differentiated into another and discrete phenotype due to their interaction with the hematopoietic cells (Prockop, *Science* v276 n5309, p71 (4)(April 1997)). It has been widely believed that the stromal cells of the Dexter cultures are a heterogeneous mixture of adipocytes, osteoblasts, fibroblasts, muscle cells, and vascular endothelial cells.

The in vitro analysis and study of hematopoiesis in Friedenstein and Dexter culture systems has been of great importance in both veterinary and human medicine. A number of diseases and immune disorders, as well as malignancies, appear to be related to disruptions within the hematopoietic system.

Allogeneic bone marrow transplantation is the preferred treatment for a variety of malignant and genetic diseases of the blood and blood-forming cells. The success rate of allogeneic bone marrow transplantation is, in large part, dependent on the ability to closely match the major histocompatibility complex of the donor cells with that of the recipient cells to minimize the antigenic differences between the donor and the recipient, thereby reducing the frequency of host-versus-graft responses and graft-versus-host disease (GvHD). Unfortunately, only about 20% of all potential candidates for bone marrow transplantation have a suitable family member match.

Bone marrow transplantation can be offered to those patients who lack an appropriate sibling donor by using bone marrow from antigenically matched, genetically unrelated donors (identified through a national registry), or by using bone marrow from a genetically related sibling or parent whose transplantation antigens differ by one to three of six human leukocyte antigens from those of the patient. Unfortunately, the likelihood of fatal GvHD and/or graft rejection increases from 20% for matched sibling donors to 50% in the cases of matched, unrelated donors and un-matched donors from the patient's family.

The potential benefits of bone marrow transplantation have stimulated research on the cause and prevention of GvHD. The removal of T cells from the bone marrow obtained from matched unrelated or unmatched sibling donors results in a decreased incidence of graft versus host reactions, but an increased incidence of rejection of the allogeneic bone marrow graft by the patient.

Current therapy for GvHD is imperfect, and the disease can be disfiguring and/or lethal. Thus, risk of GvHD restricts the use of bone marrow transplantation to patients with otherwise fatal diseases, such as severe immunodeficiency disorders, severe aplastic anemia, and malignancies.

The potential to enhance engraftment of bone marrow or stem cells from antigenically mis-matched donors to patients without graft rejection or GvHD would greatly extend the availability of bone marrow transplantation to those patients without an antigenically matched sibling donor.

Thus, it would be useful to develop methods of improving and/or enhance bone marrow transplantation by enhancing the engraftment of bone marrow or hematopoietic progenitor cells and/or decreasing the occurrence of graft rejection or GvHD in allogenic transplants.

Studies of hematopoiesis and mesengenesis and the urgent need for improved methods of treatment in the field of bone marrow transplants have led to the isolation of MSCs from bone marrow stroma. These MSCs are the same pluri-potential cells that result from expansion in Friedenstein type cultures. Several patents describe the isolation and therapeutic uses of these MSCs.

U.S. Pat. No. 5,486,359, to Caplan, et al., discloses isolated human MSCs, and a method for their isolation, purification, and culturing. Caplan, et al. also describes methods for characterizing and using the purified mesenchymal stem cells for research, diagnostic, and therapeutic purposes. The invention in '359, to Caplan, et al., describes pluri-potential cells that remain pluri-potential, even after cultural expansion. Caplan, et al. also teaches that it is necessary to first isolate the pluri-potent MSCs from other cells in the bone marrow and then, in some applications, uses culture medium to expand the population of the isolated MSCs. The Caplan et al. patent fails to disclose the use of Dexter-type cultures, pluri-differentiated mesenchymal progenitor cells, or the isolation of cells from Dexter-type cultures.

U.S. Pat. No. 5,733,542, to Haynesworth, et al., discloses methods and preparations for enhancing bone marrow engraftment in an individual by administering culturally expanded MSC preparations and a bone marrow graft. U.S. Pat. No. 6,010,696, to Caplan, et al., discloses methods and preparations for enhancing hematopoietic progenitor cell engraftment in an individual by administering culturally expanded MSC preparations and hematopoietic progenitor cells. The cells utilized in the Haynesworth, et al. patent and the '696 patent to Caplan, et al. are the pluri-potential cells described in U.S. Pat. No. 5,486,359. Neither patent discloses the use of Dexter-type cultures, pluri-differentiated mesenchymal progenitor cells, or the isolation of cells from Dexter-type cultures.

Mesenchymal stem cells that are isolated from bone marrow are further described by Prockop, in *Science* v276 n5309, p71 (4)(1997) and Pittenger, et al. in *Science* v284 i5411, p143 (1). These articles also describe pluri-potential but undifferentiated MSCs and fail to teach or disclose a pluri-differentiated mesenchymal cell or the isolation of mesenchymal cells from Dexter-type cultures.

While the cells disclosed in the prior art may provide some benefit, the isolated MSCs in the prior art have not solved the problems associated with engraftment of hematopoietic progenitor cells or bone marrow. Consequently, there exists a need in the art for methods of improving engraftment of hematopoietic progenitor cells and bone marrow in mammals in need of such treatment. There also exists a need in the art for treating and preventing the occurrence of GvHD in mammals that receive allogeneic bone marrow transplants.

SUMMARY OF THE INVENTION

According to the present invention there is provided isolated pluri-differentiated mesenchymal progenitor cells, a method of isolation, diagnostic uses, and therapeutic uses relating to enhancing the engraftment of human bone marrow or hematopoietic progenitor cells and treating GvHD.

The present invention provides an isolated mesenchymal progenitor cell that is pluri-differentiated.

Accordingly, the present invention also provides a method for purifying pluri-differentiated mesenchymal progenitor cells including the steps of: providing a cell culture preparation by the Dexter method, treating the cells to obtain a cell suspension, removing macrophages, fractionating the cells, and collecting the fraction of pluri-differentiated mesenchymal progenitor cells.

The present invention also provides a method for enhancing bone marrow engraftment in a mammal in need thereof which includes administering to the mammal (i) isolated pluri-differentiated mesenchymal progenitor cells and (ii) a bone marrow graft, wherein the pluri-differentiated mesenchymal progenitor cells are administered in an amount effective to promote engraftment of the bone marrow in the mammal.

The present invention provides a method for enhancing engraftment of hematopoietic progenitor cells in a mammal in need thereof which includes the step of administering to the mammal (i) isolated pluri-differentiated mesenchymal progenitor cells and (ii) hematopoietic progenitor cells, wherein the pluri-differentiated mesenchymal progenitor cells are administered in an amount effective to promote engraftment of the hematopoietic progenitor cells in the mammal.

Another embodiment of the present invention provides a method for treating graft-versus-host disease (GvHD) in a mammal about to undergo bone marrow or organ transplantation or suffering from GvHD caused by bone marrow or organ transplantation, by administering to the mammal an effective amount of isolated pluri-differentiated mesenchymal progenitor cells.

Yet another embodiment of the present invention provides a method for diagnosing a disease state by: a) establishing gene expression patterns of normal state bone marrow derived isolated pluri-differentiated mesenchymal progenitor cells; b) establishing gene expression patterns of various leukemic state bone marrow derived isolated pluri-differentiated mesenchymal progenitor cells; c) identifying gene sets that are unique to a given state; and d) comparing a profile of bone marrow derived isolated mesenchymal progenitor cell of unknown state to the gene sets.

Additionally, the present invention provides a method for identifying therapeutic targets for treatment of hematopoietic function by: a) determining the median gene expression profile of bone marrow isolated pluri-differentiated mesenchymal progenitor cells associated with each disease state of interest; b) identifying gene groups that are up-regulated, down regulated, and common to each disease state; and c) identifying gene sets that are unique to a given state.

The present invention also includes therapeutic compositions including isolated pluri-differentiated mesenchymal progenitor cells and a pharmaceutically acceptable carrier, wherein the pluri-differentiated mesenchymal progenitor cells are present in an amount effective to enhance bone marrow engraftment in a mammal in need thereof; enhance hematopoietic progenitor cell engraftment in a mammal in need thereof; or treat GvHD in a mammal about to undergo bone marrow or organ transplantation or suffering from GvHD caused by bone marrow or organ transplantation.

BRIEF DESCRIPTION OF THE FIGURES

Other advantages of the present invention can be readily appreciated as the same becomes better understood by reference to the following detailed description when considered in connection with the accompanying drawings. The following is a brief description of the drawings which are presented only for the purposes of further illustrating the invention and not for the purposes of limiting same. Referring to the drawing figures, like reference numerals designate identical or corresponding elements throughout the several figures.

(FIG. 4A) Wright-Giemsa (Harleco stain using HMS Series Programmable Slide Stainer, Carl Zeiss, Inc.). (FIG. 4B) Immunostain using anti-CD68 antibody (Immunotech, Clone PG-M1; Vector, Vectastain Elite ABC Kit). (FIG. 4C) Immunostain using anti-CD45 antibody (Dako, Clone PD7/26 & 2B11; ABC Kit). (FIG. 4D) Periodic acid-Schiff (Sigma). (FIG. 4E) Nile Red (Sigma), counterstained with DAPI (Vector). (FIG. 4F) Alkaline phosphatase (Sigma Kit No. 85), counterstained with Nuclear Fast Red (Baker). (FIG. 4G) Immunostain using antibody to fibronectin (Immunotech, Clone 120.5; ABC Kit). (FIG. 4H) Immunostain using anti-muscle actin antibody (Ventana, clone HUC 1—1; Ventana system using a section of formalin-fixed, paraffin-embedded cell block, instead of a cytospin). Appropriate positive controls and isotype-matched negative controls were employed to ascertain antibody staining-specificity. All parts of figure as shown, except 4E and 4H, have clearly identifiable built-in cell controls. The morphological features of the cells are listed in row 1 of Table 1.

FIGS. 6A–M represent different gene probes used for hybridization. The following outlines the sources of the gene probes employed and the approximate sizes of the major transcripts observed (shown in parentheses): FIG. 6A) CD68 (Clone ID 3176179, Genome Systems, Inc (GSI); 2–3 kb); FIG. 6B) Cathepsin B (Clone ID 2806166, GSI; 2–3 kb); FIG. 6C) GAPDH probe (generated using PCR primers from R&D Systems, Inc; ~2 kb) hybridized to same blot as A and B; FIG. 6D) Adipsin (probe generated using PCR primers as described, Ref 20; 0.5–1 kb); FIG. 6E) Osteoblast-specific cadherin-11 (Clone ID 434771, GSI; ~3 kb); FIG. 6F) Chondroitin sulfate proteoglycan 2 (Clone ID 1623237, GSI; >10 kb); FIG. 6G) Collagen type I alpha 1 (Clone ID 782235, GSI; >10 kb); FIG. 6H) Decorin (Clone ID 3820761, GSI; 2–3 kb); FIG. 6I) GAPDH probe hybridized to same blot as D–H; FIG. 6J) Fibronectin (Clone ID 3553729, GSI; >10 kb); FIG. 6K) Caldesmon (Clone ID 1319608, GSI; ~4 kb); FIG. 6L) Transgelin (Clone ID 4049957, GSI; ~1.5 kb); and FIG. 6M) GAPDH probe hybridized to same blot as J–L.

FIG. 9A shows CD45+/CD34+ progenitors in the marrow. FIG. 9B shows CD45/CD34—mature hematopoietic cells circulating in the blood.

FIG. 10A shows a serial section of a mouse spleen stained with H & E. FIG. 10B shows a serial section of a mouse spleen stained with immunoperoxidase stain for CD45. FIG. 10C shows bone marrow stained for CD45. FIG. 10D shows a serial section of the mouse liver stained with H&E depicting involvement of periportal areas. FIG. 10E shows a serial section of the mouse stomach stained with H&E showing transmural infiltration. FIG. 10F shows a serial section of the mouse lung stained with H&E showing involvement of peribronchial area. FIG. 10G shows a serial section of the mouse pancreas stained with H&E. FIG. 10H shows a serial section of the mouse paravertebral ganglia stained with H&E.

FIG. 12A shows that hybridization of sample DNA using a DNA probe specific for human chromosome 17 alpha satellite DNA (p17H8) results in a 2.7 Kb band (7) (arrow; autoradiogram exposed for only 45 minutes). FIG. 12B shows EcoR1 digest of thymic genomic DNA from SCID mice. FIG. 12C shows EcoR1 digest of lymph node genomic DNA from SCID mice. FIG. 14A shows a serial section of the liver of the mouse that survived. FIG. 14B shows a serial section of the liver of the mouse that died. FIG. 14C shows a serial section of the spleen of the mouse that survived.

FIGS. 19 and 20 show gene-expression plots of diverse mesenchymal lineage-associated genes and housekeeping genes by collective MPCs and single-cell MPCs. Individual samples are represented on X-axis. Signal intensity of a transcript in log scale normalized across samples is shown on Y-axis. Note the differing log scales, particularly the wide range of log scale for ACTB. Representative lineage markers are shown as follows. Osteoblast markers: osteoblast-specific factor 2 (probe ID 1451_s-at), osteoblast cadherin 11 (ID 2087_s_at) and collagen 1 alpha 2 (ID 32306_g_at). Muscle markers: caldesmon (ID 41738_at), transgelin-2 (ID 36678_at) and smooth muscle myosin heavy chain (ID 32838_at). Fibroblast markers: fibronectin (ID 31719_at) and prolyl 4-hydroxylase (ID 37037_at). Adipocyte markers: adipsin (ID 40282_at) and adipocyte-specific ECM protein (ID 39673_i_at). Housekeeping genes: GAPD (ID 35905_s_at) and ACTB (ID 32318_s_at). Samples 1–5, respectively, represent MPC A, MPC B R2, MPC C R2, MPC D R1, MPC D R2. Samples 6–15, respectively, represent SCA1, SCA2, SCA3, SCB1, SCB3, SCC1, SCC3, SCD1, SCD2, SCD3.

DETAILED DESCRIPTION OF THE INVENTION

Generally, the present invention provides isolated and purified mesenchymal progenitor cells that are pluri-differentiated. Also provided by the present invention is a therapeutic composition including an effective amount of isolated and purified pluri-differentiated mesenchymal progenitor cells and a pharmaceutically acceptable carrier.

The terms "enhance" or "improve" as used herein are intended to indicate that the there is a more beneficial end result. In other words, the product provides a more effective result.

The term "pluri-differentiated" as used herein refers to cells that are a single cell type co-expressing genes specific for multiple lineages. The term "pluri-potential" as used herein refers to cells that are undifferentiated and have the potential to be differentiated into discrete mesenchymal tissues.

Dexter-type cultures contain stromal cells that co-express multiple message lineage markers. These pluri-differentiated cells are referred to by the inventor as mesenchymal progenitor cells (MPCs). Disclosed herein is a process for isolating and purifying MPCs from Dexter-type cultures. Purified MPCs provide a sufficiently defined system to permit detailed elucidation of the role of bone marrow in normal and leukemic hematopoiesis.

The present invention also provides various methods for using MPCs to enhance bone marrow transplantation, enhance hematopoietic progenitor cell engraftment, for diagnostic purposes, or for the treatment of GvHD.

The exact cell types in Dexter cultures have been identified. No evidence was found for the existence of discrete cellular populations, such as adipocytes, osteoblasts, fibroblasts, smooth muscle cells and endothelial cells, notwithstanding the abundance of literature and wide spread belief (See, J. L. Liesveld et al., *Blood* 73, 1794 (1989); A. K. Sullivan, D. Claxton, G. Shematek et al., *Lab Invest* 60, 667 (1989); K. Dorshlind, *Ann Rev Immunol* 8, 126 (1990); S. Perkins, R. A. Fleischman, *Blood* 75, 620 (1990); I. A. Denkers, R. H. Beelen, G. J. Ossenkoppele et al., *Ann Hematol* 64, 210 (1992); P. E. Penn, D. Z. Jiang, R. G. Fei et al., *Blood* 81, 1205 (1993); E. de Wynter et al., *J Cell Sci* 106, 761 (1993); A. Ferrajoli et al., *Stem Cells (Dayt)* 12, 638 (1994); B. R. Clark, A. Keating, *Ann NY Acad Sci* 770, 70 (1995); B. S. Wilkins, D. B. Jones, *Br J Haematol* 90, 757 (1995); S. Gronthos, P. J. Simmons, J Hematother 5, 15 (1996); D. Soligo et al., Abstract #3926, *Blood* 94, Supplement 1 (Part 2 of 2), p. 168b, Forty 1$^{st}$ Annual Meeting of the American Society of Hematology, New Orleans, La., Dec. 3–7, 1999, M-A. Dorheim et al., *J Cell Physiol* 154, 317 (1993), M. K. Majumdar, M. A. Thiede, J. D. Mosca et al., *J Cell Physiol.* 176, 57 (1998), D. J. Prockop, *Science* 276, 71 (1997), R. S. Taichman, S. G. Emerson, *J Exp Med* 179, 1677 (1994); R. S. Taichman, M. J. Reilly, S. G. Emerson, *Blood* 87, 518 (1996); C. M. Verfaillie, in *HEMA-*

Figure 3:
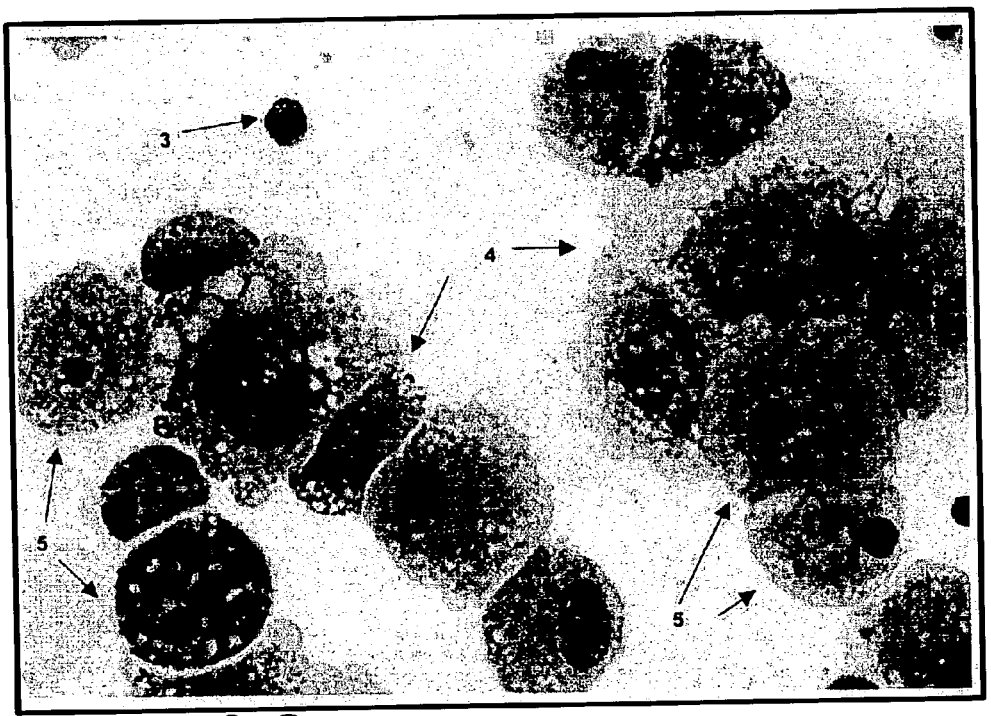
FIG. 3 is a photograph showing the Wright-Giemsa staining of Dexter-type stromal cell cultures depicting three morphologically identifiable cell populations, macrophages (5), hematopoietic cells (3), and the mesenchymal progenitor cells (4) of the present invention.
Figure 4:
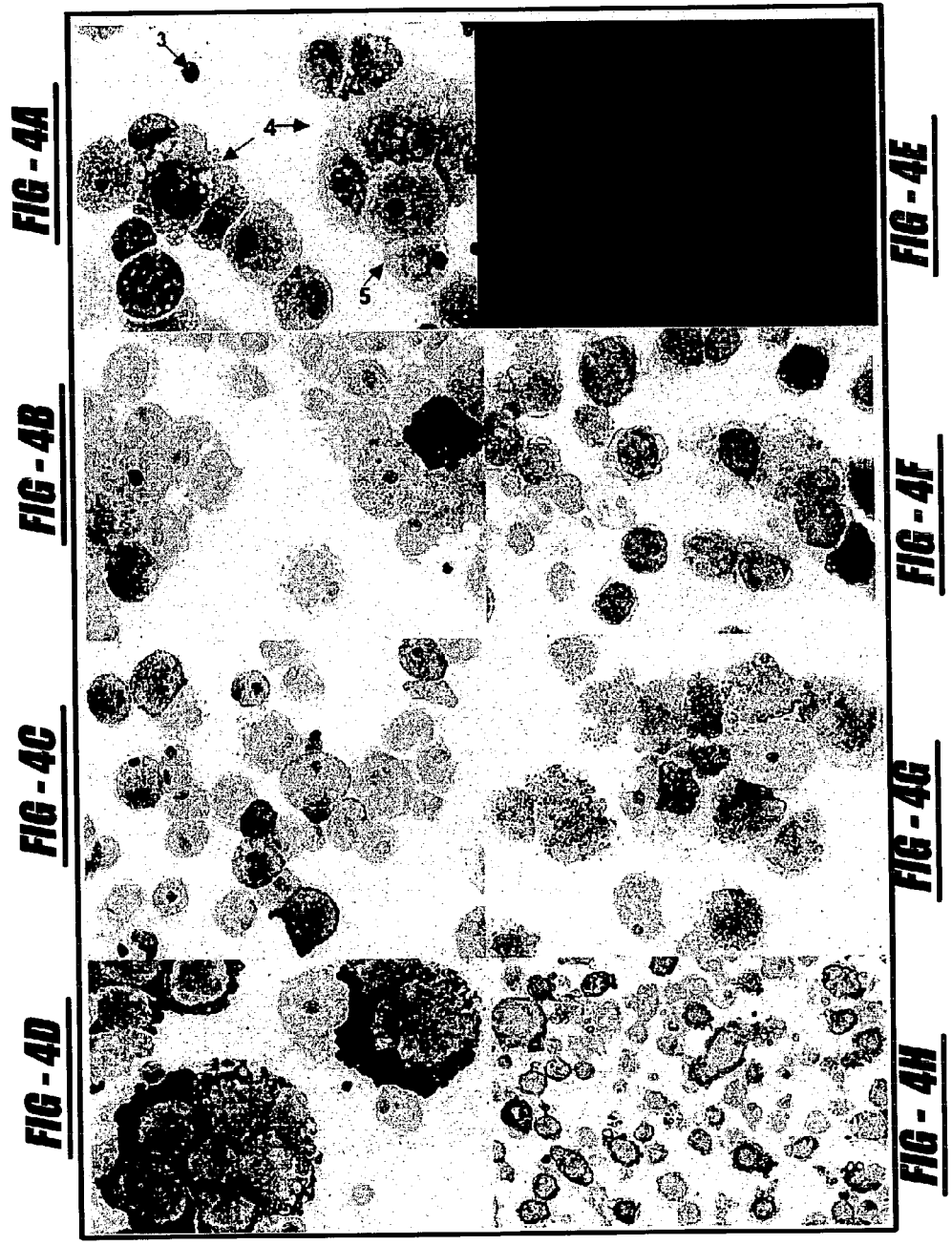
FIGS. 4A–H show a series of photomicrographs showing the morphologic and phenotypic characteristics of the MPCs of the present invention, as uncovered by staining for representative mesenchymal cell lineage markers. The methods applied are shown in parentheses.
Figure 5:
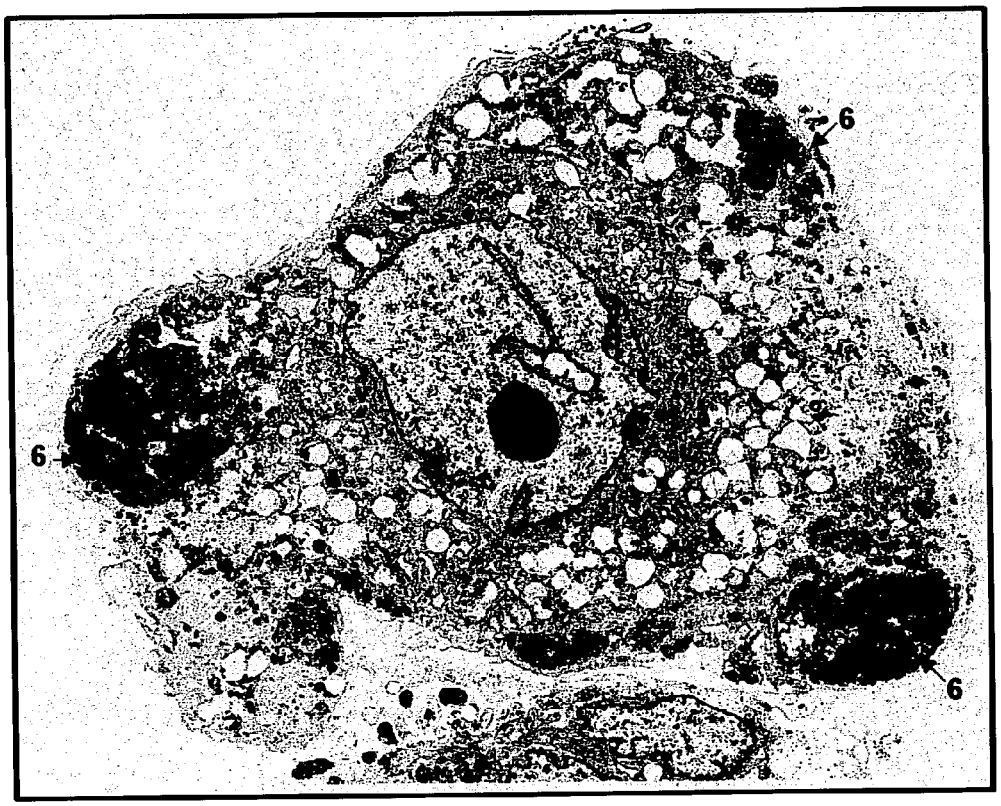
FIG. 5 is a photograph which shows a transmission electron micrograph of an MPC of the present invention bearing microvilli, irregular nucleus, and pools of glycogen (6) in the ectoplasm (×4,600).

TOLOGY: Basic Principles and Practice, R. Hoffman, et al., Eds. (Churchill Livingstone, N.Y., 2000), pp. 140–142.), A. J. Henderson, A. Johnson, K. Dorshkind, *J Immunol* 145, 423 (1990); M. W. Long, J. L. Williams, K. G. Mann, *J Clin Invest* 86, 1387 (1990); P. J. Simmons, S. Gronthos, A. Zannettino et al., *Prog Clin Biol Res* 389, 271 1994); B. A. Roecklein, B. Torok-Storb, *Blood* 85, 997 (1995); J. Wineman, K. Moore, I. Lemischka et al., *Blood* 87, 4082 (1996); K. A. Kelly, J. M. Gimble, *Endocrinology* 139, 2622 (1998); K. C. Hicok et al., *J Bone Miner Res* 13, 205 (1998); S. R. Park, R. O. Oreffo, J. T. Triffitt, *Bone* 24, 549 (1999); J. E. Dennis et al., *J Bone Miner Res* 14, 700 (1999); and B. Torok-Storb et al., *Ann NY Acad Sci* 872, 164 (1999)). Instead, the inventor determined that there are only three types of cells in Dexter-type cultures, namely, macrophages (~35%), hematopoietic cells (~5%), and a type applicant calls "nonhematopoietic cells" (~60%)(FIG. 3, FIG. 4A, and Table 1).

Bone marrow mesenchymal cells, the nonhematopoietic cells in Dexter type cultures, possess distinctive features that have previously gone unrecognized. There is both direct visual (FIGS. 4A–E and FIG. 5) and molecular biological (FIG. 6) evidence to support the existence of this unique cell type. These findings challenge the prevailing belief that stromal cells derived from Dexter cultures comprise multiple singly-differentiated mesenchymal cell types. Because Dexter cultures represent a primary cell culture system, and not a cell line, these studies indicate that cells in these primary cultures themselves are pluri-differentiated, which has been previously unsuspected. The nonhematopoietic cells of the present invention (MPCs) simultaneously express marker genes specific for multiple mesenchymal cell lineages, including adipocytes, osteoblasts, fibroblasts and smooth muscle cells. As shown in the present disclosure, MPCs can also differentiate into B cells and therefore be useful in affecting the functionality of the immune system.

The MPCs in Dexter type cultures were characterized using a variety of techniques. Cytospins were prepared using aliquots of unfractionated cells for performance of various cytological, cytochemical and immunocytochemical stains. Reactivity patterns of the bone marrow culture cells are outlined in Table 1. FIGS. 4A–E illustrate morphologic and phenotypic characteristics, as uncovered by staining for representative cell lineage markers.

Only rarely have investigators in this field taken the approach of preparing a cell suspension and staining cells on cytospins as was done to characterize the cells of the present invention (Simmons, et al., *Nature* 328, p 429–32 (1987)) and no other group has used this method to address the issue of pluri-differentiation by bone marrow stromal cells. Almost all of the published studies in the field, with a rare exception (Simmons, et al., *Nature,* 328, p 429–32 (1987)), conducted cytochemical and immunocytochemical staining on layers of stromal cells grown to confluence on coverslips. In this situation, the stromal cultures appear very complex especially in the areas of hematopoietic activity, so-called "cobblestones" with macrophages and hematopoietic cells enmeshed in them. Macrophages and nonhematopoietic cells spread themselves and assume varied shapes when they adhere to and grow on plastic or glass. This spreading further contributes to the perceived heterogeneity and complexity. The complexity precludes a clear morphological visualization of the nonhematopoietic cells and consequently interferes with the determination of what percent of what cell type is positive for any given marker.

In terms of lineage markers, up to 100% of the nonhematopoietic cells or MPCs of the present invention expressed two fat cell markers (Nile Red (FIG. 4E) and Oil Red O); an osteoblast marker (alkaline phosphatase (FIG. 4F)); and two fibroblast markers (fibronectin (FIG. 4G) and prolyl-4-hydroxylase). Greater than 85% of the MPCs were also positive for a muscle marker, actin (FIG. 4H). There was no evidence of expression of endothelial cell differentiation, as judged by immunohistochemical staining for CD34 and CD31.

In addition, the Dexter type stromal cells had not previously been subjected to Periodic Acid-Schiff (PAS) staining, which revealed a strong and uniform positivity by almost 100% of the MPCs studied. This indicates the presence of large stores of glycogen (FIG. 4D). The presence of glycogen (6) was confirmed by electron microscopy (see FIG. 5). In this respect, MPCs are reminiscent of the glycogen-laden reticular cells in the developing bone marrow of human fetuses (observed by L-T. Chen, L. Weiss, *Blood* 46, 389 (1975)). Glycogen deposition is viewed to be a developmentally regulated process during morphogenesis (H. Ohshima, J. Wartiovaara, I. Thesleff, *Cell Tissue Res.* 297, 271 (1999)).

The MPCs also exhibited cytoplasm compartmentalization into endoplasm and ectoplasm. This morphologic finding sheds light on their internal architecture because of correlation of restricted localization of glycogen and smooth muscle actin to ectoplasm; and the restricted localization of acid phosphatase, alkaline phosphotase, Nile Red, Oil Red O, fibronectin, and prolyl-4-hydrolase to endoplasm.

Additional sets of multiple mesenchymal lineage markers were assessed by Northern blotting of unfractionated cells and purified MPCs to eliminate any observer bias that might be inherent in morphological assessment. FIGS. 6A–M represent different gene probes used for hybridization.

Compared to unfractionated cells, the purified nonhematopoietic cells expressed significantly higher levels of markers representing fat cells (adipsin, FIG. 6D); osteoblasts (osteoblast-specific cadherin-11, chondroitin sulfate, collagen type 1 and decorin, FIGS. 6E–H); fibroblasts (fibronectin, FIG. 6J); and smooth muscle cells (caldesmon and transgelin, FIGS. 6K–L).

Taken together, the morphologic, cytochemical, and immunocytochemical results (FIG. 4A-H and Table 1), and the Northern blotting data (FIG. 6A-M) indicate that the nonhematopoietic stromal cells of the Dexter cultures co-express markers specific for at least four different mesenchymal cell lineages. Using a variety of techniques, applicant has demonstrated that the MPCs co-express multilineage mesenchymal cell phenotypes, and in this respect the multi- or pluri-differentiated MPCs are distinct from the pluri-potential, but undifferentiated, MSCs of Friedenstein cultures (Prockop, *Science* 276, 71–74 (1997).

Figure 2:
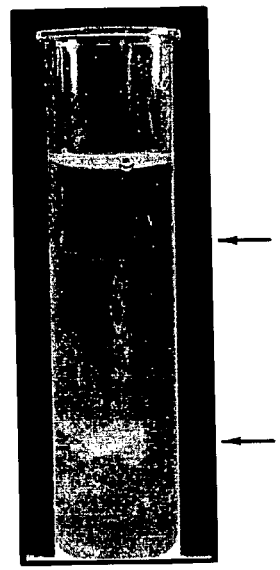
FIG. 2 is a photograph showing the percoll gradient centrifugation technique of the present invention that purifies the MPCs (2) in large quantities to greater than 95% purity.

The nonhematopoietic cells of the present invention were purified from the macrophages, the dominant "contaminating" cell type, using a Percoll gradient method developed by applicant. MPCs were purified by the following process: cells from a Dexter-type culture were treated to obtain a cell suspension, the macrophages were removed, and the cells were fractionated using discontinuous Percoll gradient centrifugation (FIG. 2). The isolated MPCs were then collected and washed.

The purity of the nonhematopoietic cells was demonstrated by a near complete absence of two macrophage markers, CD68 and cathepsin B (as shown by Northern blotting data, FIGS. 6A and 6B). As a positive control, bone marrow mononuclear cells rich in myelomonocytic cells abundantly expressed CD68 (lanes 5 & 6, FIG. 6A). The Northern blot results are consistent with a purity estimate of ~95% (vs. 60% in unfractionated samples) based on morphology and immunocytochemical staining for CD68.

A purified source of MPCs is desirable for a number of reasons. The relative ease with which large numbers of the MPCs can be purified and their distinctive phenotypic characteristics make them valuable targets for future investigations. Purified MPCs provide a sufficiently defined system to permit detailed elucidation of the role of bone marrow in normal and leukemic hematopoiesis in addition to aiding in bone marrow transplantation.

Another major reason that purified cells are desirable is that Dexter cultures also contain a significant percentage of highly immunogenic macrophages that can cause onset of GvHD after transplantation. The MPCs of the present invention are purified to ~95% free of macrophages and hematopoietic cells. Note the increased survival rate in Severe Combined Immunodeficiency Disease (SCID) mice that received purified MPCs versus those that received unfractionated bone marrow stromal cells in FIG. 13B. This data establishes that stromal cells in combination with engraftment or other similar procedures enhances the effectiveness of the treatment.

Figure 7:
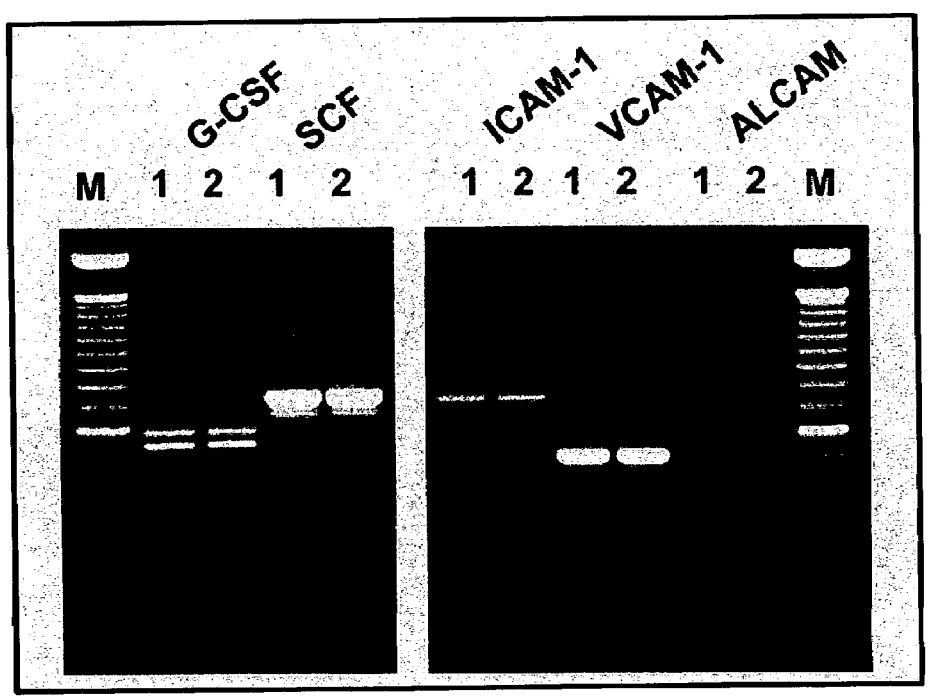
FIG. 7 is a photograph which shows RT-PCR analysis for expression of representative hematopoietic growth factors (G-CSF and SCF) and extracellular matrix receptors (ICAM-1, VCAM-1, and ALCAM) by the MPCs of the present invention.

The present invention also provides methods of enhancing the engraftment of hematopoietic cells and of enhancing the engraftment of bone marrow. The hematopoietic support capacity of the Dexter-type cultures has been repeatedly demonstrated by a number of investigators. RT-PCR analysis showed that Dexter cultures and Friedenstein cultures expressed a similar pattern of cytokine and growth factor mRNAs; yet, Dexter cultures were found to be more efficient than Friedenstein cultures in achieving preservation of hematopoietic progenitors (Majumdar, et al., *J. Cell. Physiol*, 176, 57–66.). The pluri-differentiated MPC is capable of supporting hematopoiesis, as shown by its ability to express representative hematopoietic growth factors/cytokines, i.e., G-CSF and SCF as well as matrix receptors/hematopoietic cell adhesion molecules, i.e., ICAM-1, VCAM-1 and ALCAM (FIG. 7).

Clarification of the nature of the stromal cells and the ability to purify these cells makes it possible to use them as an adjuvant in bone marrow transplantation following high-dose chemotherapy and radiation therapy. These treatment modalities not only cause damage to the hematopoietic stem cells but also to the supportive stromal cells. However, because the bone marrow microenvironment is destroyed, hematopoietic progenitor cell engraftment is delayed until the stromal environment is restored. As a result, a critical aspect of the current invention is directed to the advantages of transplanting isolated mesenchymal progenitor cells to accelerate the process of stromal reconstruction and ultimately bone marrow engraftment. The stromal cells present in the standard bone marrow transplant are not sufficient in number and can be supplemented with the cultured MPCs of the present invention.

Yet another embodiment of the current invention provides the use of MPC transplantation to major leukemic conditions, such as acute myeloid leukemia (AML), myelodysplastic syndromes (MDS), chronic myeloid leukemia (CML) and multiple myeloma (MM). This is based on applicant's determination that bone marrow stromal cells in a leukemia patient are functionally and structurally defective, regardless of the damage caused by chemotherapy and radiation therapy. Such defects in bone marrow stromal cells are likely to aid and abet leukemia development. Alternatively, stromal cell defects could be secondarily induced by surrounding leukemia cells, thus contributing to the loss of hematopoietic support function of stromal cells and hematopoietic failure, which is an invariable feature in leukemia. Regardless whether the observed stromal cell defects are primary or secondary to the leukemic process, by reason of their indisputable impact on normal hematopoiesis, these defects remain to be corrected to improve the hematopoietic function.

Stromal cells have never been carefully investigated in terms of genomics in view of the widespread belief that they represent a heterogeneous mixture of cell types. Tissue or cellular heterogeneity presents a major challenge for the application of microarray technology. The purified stromal cells of the present invention represent a single pluridifferentiated MPC which allows for genomic study of the stromal cells and the development of new, more objective diagnostic tools for patients suffering from leukemia conditions.

The present invention provides a comprehensive phenotype of cultured bone marrow stromal cells at single cell level for the first time. These findings pave the road for ultimate identification and investigation of these cells in fresh samples of marrow, normal as well as diseased, in which they occur at a low frequency and are extremely difficult to study at the present time. The development of this phenotype forms the basis for various diagnostic tests including a comprehensive test that can be used to screen for different abnormalities of bone marrow stromal cells in various hematologic diseases and other diseases effecting stromal cells.

Results show that isolated single stromal cells simultaneously express transcripts for osteoblasts, fibroblasts, muscle cells and adipocytes. Furthermore, there is shown that isolated single stromal cells simultaneously express transcripts for epithelial cells and neural/glial cells as well as transcripts for CD45, CD19, CD10, CD79a, and representative proto-oncogenes and transcription factors, typically known to be affiliated with normal and neoplastic hematopoietic cells. These findings are evidence of existence of a progenitor cell that is common to nonhematopoietic mesenchymal cells and hematopoietic cells, particularly B-lymphocytes. "Lineage burst" characterized by simultaneous activation of diverse differentiation pathways within the same cell appears to be the signature profile of a stromal cell, indicating that a "pluripotent" cell is "pluridifferentiated" at the molecular level. That is, prior to a selective and full-fledged lineage differentiation, progenitors express genes associated with multiple lineages to which they might possibly commit, thus providing insight into the molecular basis of cellular plasticity.

Transcriptomic analysis has been undeniably contributing to the molecular definition of new disease categories with demonstrable therapeutic benefit. The present invention contributes to the further definition of the stromal cell by refining its molecular signature. The in vivo identification of the stromal cell and its possible ontogenic variants as they might occur in different hematological diseases and subsequent targeting of these cells holds the key to ultimately treating some, if not all, of these diseases.

By comprehensively defining the gene expression profile of these cells, the present invention demonstrates the technical applicability of single-cell genomics toward understanding the physiology and pathology of both hematopoietic and nonhematopoietic microenvironments. Classically, the adventitial reticular cells located on the abluminal side of the vascular endothelium within the bone marrow microenvironment were thought to represent the stromal cells or their precursors. As with hematopoietic stem or progenitor cells, the stromal progenitor cells are rare in bone marrow occurring at an estimated frequency of 1 in $10^5$ nucleated cells. Cultured stromal cells represent the progeny of the stromal cell, and not necessarily the stromal cell itself, for which no in vivo assay exists as yet. The technology of single-cell genomics and the blueprint as described in the present invention allows screening for the abnormalities of bone marrow stromal cells in fresh marrow samples that reflect on the ultimate in vivo context.

The ability to purify culture-expanded MPCs from both normal individuals and patients afflicted with various leukemias also allows testing of the hematopoietic supportive role of MPCs in mice models. These systems provide an in vivo model in which to examine the role of human bone marrow microenvironment in normal and leukemic hematopoiesis.

The SCID mouse model is an ideal system in which to investigate MPC function. Engraftment of human hematopoietic progenitors in SCID mice has required either coadministration of exogenous human cytokines, or cotransplantation of human bone marrow plugs or bone fragments. As disclosed herein MPCs are a convenient, new source for human bone marrow stromal cells for enhancing transplantation that does not require cytokines, bone fragment, or marrow.

Figure 13A:
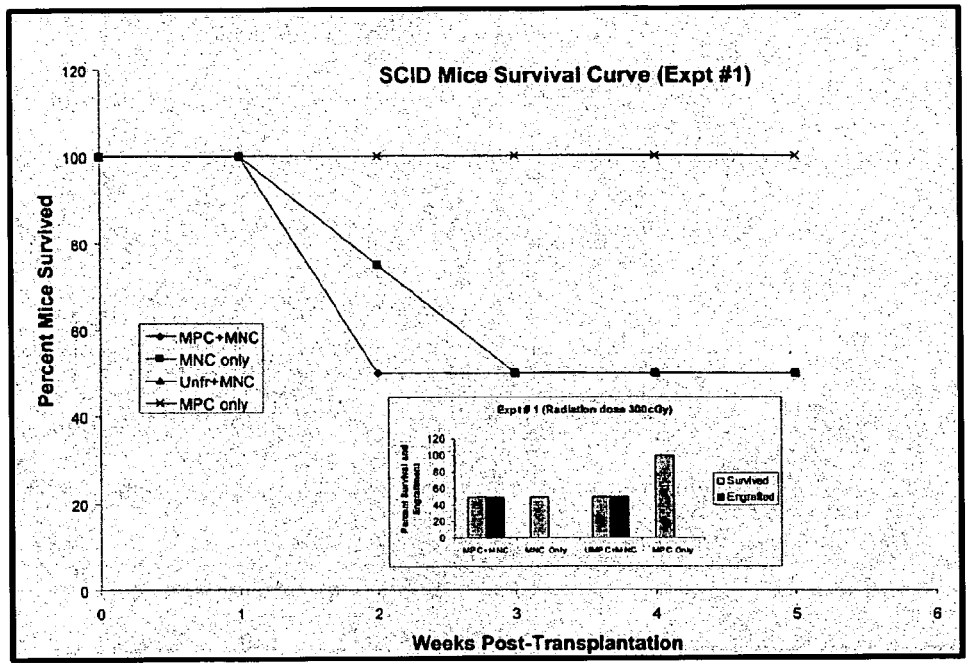
FIG. 13A and FIG. 13B show graphs comparing the survival rate and engraftment of human hematopoietic cells in SCID mice cotransplanted with the purified bone marrow MPCs of the present invention vs. unpurified bone marrow stromal cells. In the line graphs provided the line with diamonds represents MPCs and bone marrow mononuclear cells, squares represents bone marrow mononuclear cells only, triangles represents unfractionated bone marrow stromal cells, the Xs represent MPCs only, and the circles represent the control. In the bar graphs, the gray bars represent mice that survived and the black bars represent mice with engraftment.
Figure 13B:
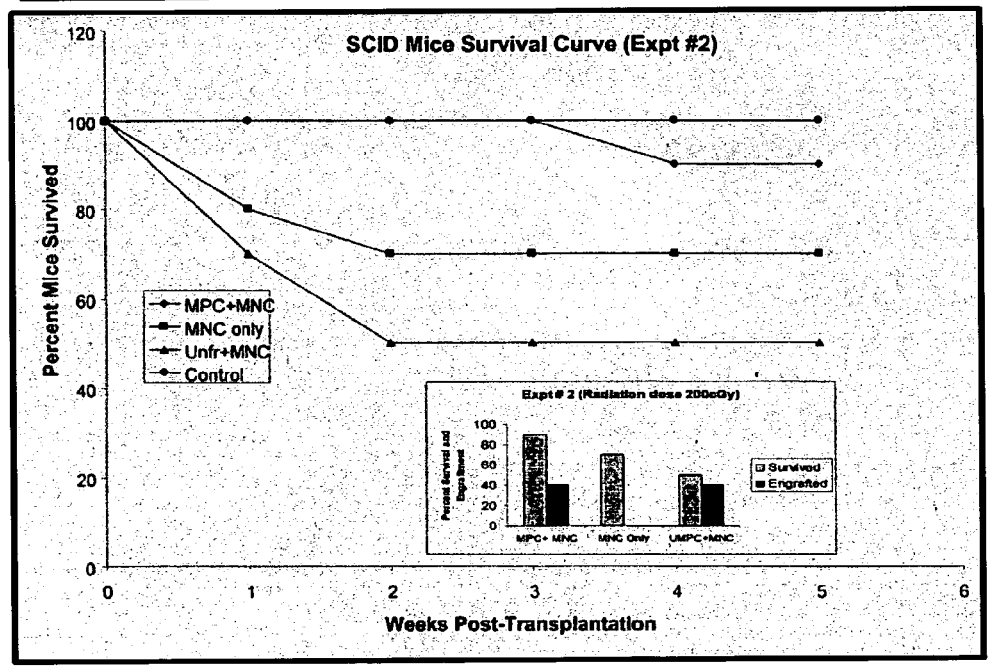

Unlike prior methods, the isolated MPCs of the present invention support human hematopoiesis in the SCID mouse model as effectively as whole marrow stroma. The transplantation of human marrow mononuclear cells combined with purified MPCs results in dramatically vigorous engraftment of human cells in spleen, bone marrow, liver, pancreas, lungs, stomach, and paravertebral neuronal ganglia of SCID mice (FIGS. 10A–H and FIGS. 11A–C). By contrast, mice receiving human bone marrow mononuclear cells alone or MPCs alone expectedly showed no detectable evidence of human hematopoietic cell engraftment (FIG. 13A and FIG. 13B).

The present invention also provides for a method of preventing or treating GvHD. The highest mortality rate, FIG. 13B, was observed in mice receiving the unpurified whole marrow stroma and the bone marrow mononuclear cells. The increased mortality observed is related to the presence of highly immunogenic macrophages and consequent GvHD. The mice with the highest survival rate, shown in FIG. 13A, were the mice receiving purified MPCs and bone marrow mononuclear cells.

Figures 14A, 14B:
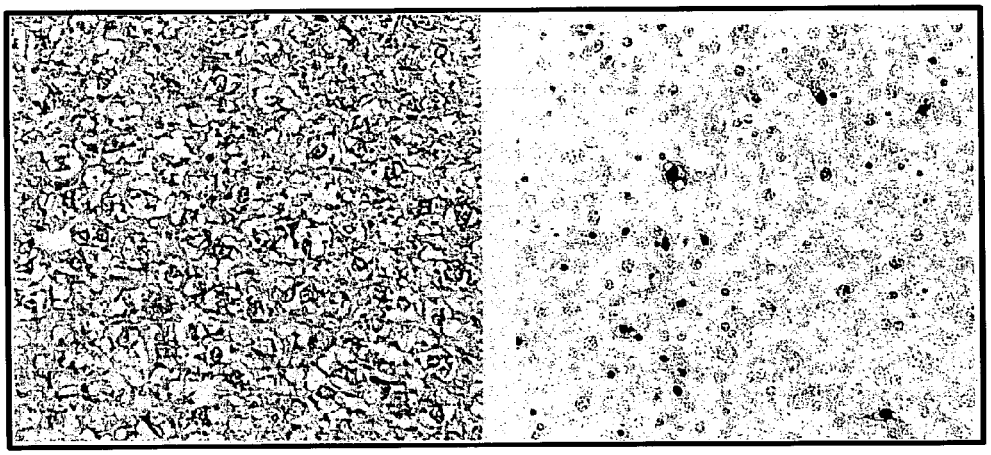
FIGS. 14A–C are photographs which demonstrate apoptosis by TUNEL assay in organs of SCID mice that died after transplantation.
Figures 14C, 14D:
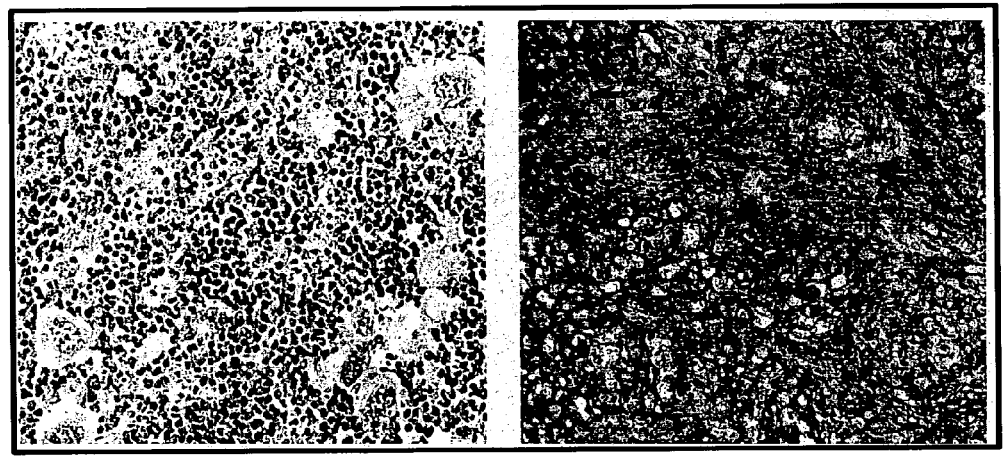
FIG. 14D shows a serial section of the spleen of the mouse that died.

Notably, there is discrete TUNEL-positive nuclei in the liver of the expired mouse in FIG. 14B and complete absence of staining in the liver of the surviving mouse (see FIG. 14A). While some ill-defined globules of staining are observed in the spleen of the mouse that survived, the nuclear integrity of most of the cells is well preserved suggesting minimal or no apoptosis (FIG. 14C). In contrast, the dead mouse spleen (FIG. 14D) showed extensive TUNEL positivity precluding accurate interpretation. Control mouse liver and spleen showed results similar to those of the mouse that survived.

The above results indicate that purified MPCs can support human hematopoiesis in SCID mice as effectively as whole marrow stroma. Equally important is that the purified MPCs increased the survival rate. The evidence shows that the increased survival is due to a reduction in GvHD.

Allogeneic bone marrow transplantation is the preferred method of treatment for a variety of malignant and genetic diseases of the blood and blood forming cells. However, failure of hematopoietic cell engraftment can occur for a number of reasons. These include, microenvironmental defects as part of the underlying disease itself (e.g., aplastic anemia), and/or stromal cell damage caused by chemoradiotherapy and/or microenvironmental damage as part of GvHD which is a dreaded complication following bone marrow transplantation. In GvHD, donor T cells present in the hematopoietic cell graft destroy host tissues. GvHD can involve multiple organs such as skin, liver, GI system etc. The current treatment modalities for preventing or treating graft failure or GvHD are cumbersome, costly and involve some form of immunosuppression. Stromal cell lesions, either primary to the disease process or secondarily induced by allogeneic bone marrow transplantation, play a prominent role in the success or failure of the hematopoietic cell graft. Cotransplantation of MPC not only enhances hematopoietic cell engraftment but also prolongs the life of graft recipients by minimizing GvHD. Co-transplantation of healthy, culture-expanded MPC is a viable option in these situations.

The human bone marrow used in the Dexter-type cultures of the present invention can be obtained from a number of different sources in accordance with the procedures known in the art, including from plugs of femoral head cancerous bone pieces or from aspirated marrow. The cells used in the Dexter culture can be autologous, from the tissue donor, or from other individuals.

Modes of administration of MPCs include, but are not limited to, systemic intravenous injection and injection directly to the intended site of activity. The MPCs can be administered by any convenient route, for example by infusion or bolus injection, and can be administered together with other biologically active agents. Administration is preferably systemic.

The methods of the present invention can be altered, particularly by (1) increasing or decreasing the time interval between administering MPCs and implanting the tissue, cells, or implanting the organs; (2) increasing or decreasing the amount of MPCs administered; (3) varying the number of MPC administrations; (4) varying the method of delivery of the MPCs; and/or (5) varying the source of MPCs.

The MPC preparations are used in an amount effective to promote engraftment of hematopoietic progenitor cells or bone marrow cells; or for the treatment or prevention of GvHD in the recipient. The pharmaceutically effective amount for the purposes herein is thus determined by such considerations as are known in the art. In general, such amounts are typically at least $1 \times 10^4$ MPCs per kg of body weight and most generally need not be more than $7 \times 10^5$ MPCs/kg.

The present invention also provides pharmaceutical compositions. Such compositions comprise a therapeutically effective amount of MPCs and a pharmaceutically acceptable carrier or excipient. Such a carrier includes but is not limited to McCoy's medium, saline, buffered saline, dextrose, water, and combinations thereof. The formulation should suit the method of administration as is known by those of skill in the art.

In one embodiment, the MPC preparation or composition is formulated in accordance with routine procedures as a pharmaceutical composition adapted for intravenous administration to human beings. Typically, compositions for intravenous administration are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The present invention paves the way for applications of mesenchymal progenitor cells in the field of transplantation with respect to hematopoietic support, immunoregulation, and graft facilitation. MPCs can be used as a supporting cell type in bone marrow transplantation, particularly in diseases where defects in the hematopoietic stromal microenvironment are believed to prevail, such as aplastic anemia, myelofibrosis, and bone marrow failure following high dose chemotherapy and radiation therapy.

Another aspect of the invention provides a method for diagnosing various disease states in mammals by identifying new diagnostic markers, specifically the classification and diagnosis of leukemia. Prior to the present invention, stromal cells were not carefully investigated in terms of genomics because of the widespread belief that they represent a heterogeneous mixture of cell types and cellular heterogeneity presents significant challenges for the application of genetic analysis such as microarray technology. The isolated MPCs of the present invention represent a single cell type and allow for genomic study of the stromal cells.

Using the methods of the present invention, it has been determined that bone marrow stromal cells in leukemia patients are functionally and structurally defective regardless of the damage caused by chemotherapy and radiation therapy. Given the almost 25 year history and intense interest in bone marrow stromal cell cultures, previous documentation of stromal cell abnormalities has been disappointingly low (Martinez & Martinez, Exp. Hematol 11:522–26 (1983); Budak-Alpdogan, et al., Am. J. Hematol, 62:212–20 (1999); Nagao, et al., Blood, 61:589–92 (1983); Peled, et al., Exp. Hematol 24:728–37 (1996); Bhatia, et al., Blood 85:3636–45 (1995); Agarwal, et al., Blood 85:1306–12 (1995); Diana, et al., Blood 96:357a(2000)). By identifying gene sets that are unique to a given state, these differences in the stromal cells can be utilized for diagnostic purposes.

In one embodiment of the invention, isolated MPCs from a patient are assayed for expression of a large number of genes. The gene expression profile is projected into a profile of gene set expression values according to the definition of gene sets. A reference database containing a number of reference projected profiles is also created from the isolated MPCs of patients with known states, such as normal and various leukemic disease states. The projected profile is then compared with the reference database containing the reference projected profiles. If the projected profile of the patient matches best with the profile of a particular disease state in the database, the patient is diagnosed as having such disease state. Various computer systems and software (see Example 5) can be utilized for implementing the analytical methods of this invention and are apparent to one of skill in the art. Some of these software programs include Cluster & TreeView (Stanford, URLs: rana.lbl.gov or www.microarray-.org), GeneCluster (MIT/Whitehead Institute, URL: MPR/GeneCluster/GeneCluster.html), Array Explorer (SpotFire Inc, URL: http://www.spotfire.com/products/scicomp.asp#SAE) and GeneSpring (Silicon Genetics Inc, URL: http://www.sigenetics.com/Products/GeneSpring/index.html) (for computer systems and software, see also U.S. Pat. No. 6,203,987).

The methods of the present invention can also be useful for monitoring the progression of diseases and the effectiveness of treatments. For example, by comparing the projected profile prior to treatment with the profile after treatment.

One aspect of the present invention provides methods for therapeutic and drug discovery utilizing bone marrow derived isolated mesenchymal progenitor cells. The present invention can be utilized to identify stromal cell genes that can be therapeutic targets for improvement of normal hematopoietic function, which is constantly compromised, in leukemic patients. In one embodiment, gene sets are defined using cluster analysis. The genes within a gene set are indicated as potentially co-regulated under the conditions of interest. Co-regulated genes are further explored as potentially being involved in a regulatory pathway. Identification of genes involved in a regulatory pathway provides useful information for designing and screening new drugs.

Some embodiments of the present invention employ gene set definition and projection to identify drug action pathways. In one embodiment, the expression changes of a large number of genes in response to the application of a drug are measured. The expression change profile is projected into a gene set expression change profile. In some cases, each of the gene sets represents one particular pathway with a defined biological purpose. By examining the change of gene sets, the action pathway can be deciphered. In some other cases, the expression change profile is compared with a database of projected profiles obtained by perturbing many different pathways. If the projected profile is similar to a projected profile derived from a known perturbation, the action pathway of the drug is indicated as similar to the known perturbation. Identification of drug action pathways is useful for drug discovery. See, Stoughton and Friend, Methods for Identifying pathways of Drug Action, U.S. patent application Ser. No. 09/074,983.

The present invention provides a genomics strategy method for identifying genes differentially expressed in MPCs. The method begins with the preparation of total RNA from MPC samples, which leads to the generation of cDNA. From the cDNA, ds DNA can be prepared for in vitro transcription into cRNA. The cRNA is then fragmented for the hybridization of target RNA to a microarray of known genes (Affymetrix genechip containing DNA from ~12,000 known human genes, e.g., U95A oligonucleotide microarray). Finally, analysis of differentially expressed genes is accomplished using appropriate software (GeneSpring) to discern the patterns of gene expression or genomic signatures by a given MPC type (e.g., up-regulation or down-regulation).

Up-regulated and down-regulated gene sets for a given disease-associated or cytokine-stimulated MPC are combined. The combination enables those of skill in the art to identify gene sets with minimal number of elements that are unique to a given MPC type with a capability to discriminate one MPC type from another (this can be accomplished by means of a series of Venn diagrams and lists of required genes obtained via GeneSpring). Such gene sets are of immense diagnostic value as they can be routinely used in assays that are simpler than microarray analysis (for example "real-time" quantitative PCR). Such gene sets also provide insights into pathogenesis and targets for design of new drugs. For example, the method allows one to establish transcriptional profiles of MPC genes that are pathologically altered.

Those of skill in the art can use the data and methods contained herein for the following: a) study select gene or sets of genes that are relevant to hematopoietic disease conditions by using relatively inexpensive but low-throughput technologies such as Northern blotting, RNase protection assays and/or PCR intended for gene expression analysis; b) identify newer drug targets and diagnostic markers relevant to specific diseases, such as MM or CML etc depending on the research interests of the individual investigators.

The present invention also provides a large-format 2-D gel electrophoretic system for the reproducible separation of MPC proteins and for preparing 2-D PAGE protein maps for normal bone marrow-derived MPCs (untreated and treated with representative cytokines, e.g., TNF-α and/or IL-4) and for MPCs derived from patients with representative pre-leukemic/premalignant and leukemic/malignant conditions. The pre-leukemic conditions include myelodysplastic syndromes (MDS) and the leukemic conditions include chronic myeloid leukemia (CML), acute myeloid leukemia (AML), chronic lymphocytic leukemia (CLL), acute lyinphocytic leukemia (ALL), and multiple myeloma (MM). The protein samples consist of culture supernatants/secreted proteins, extracellular matrix (ECM) proteins, plasma membrane proteins solubilized using a three-step differential extraction protocol, employing conditions of progressively increasing solubility; and whole cell lysate proteins similarly solubilized using the three-step differential extraction protocol. This subproteome approach not only simplifies the 2-D PAGE electrophoretic protein patterns but also reveals additional proteins, which would otherwise have gone undetected.

The 2-D system described herein utilizes an immobilized pH gradient gel (pH 4–7) in the first dimension and a mini non-denaturing but high-resolution lithium dodecyl sulfate-polyacrylamide gel electrophoresis (LDS-PAGE) in the second dimension. As identified by silver staining, this system has resolved greater than 800 protein spots in a pH interval of 2.5 units (4.25–6.75, the isoelectric pH range for most of plasma membrane proteins to migrate) and a molecular mass range of 10–150 kDa. Equally important, the system is compatible with high sample loads (up to 1.5 to 2.0 mg of total protein in up to 350 µl sample volume). All the protein species identifiable by a silver stain that is compatible with subsequent mass spectrometric analysis have been analyzed by a 2-D gel software with respect to isoelectric point, molecular weight and mass abundance. The lectin-binding status of these proteins has also been determined by lectin blotting. Lectin blots and Western blots have subsequently been stained by a gold stain for detection of total proteins on the same PVDF membrane. Although gold-staining of the Western blot is not as sensitive as silver-staining of the gel, gold-staining of the Western blot generates the necessary landmarks for alignment with the silver stained gel, facilitating excision of spots of interest from the gel for identification by MALDI-MS. Representative protein spots were excised from gel and subjected to mass spectrometric profiling (MALDI-MS) and/or sequencing (Nano ESI MS/MS) with subsequent database searching, resulting in a productive identification of ten proteins.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The examples presented herein can be summarized as follows. The data disclosed herein demonstrate that Dexter cultures consist of only three cell types macrophages (~35%), hematopoietic cells (~5%), and nonhematopoietic cells (~60%). Using a percoll gradient centrifugation technique, the nonhematopoietic mesenchymal progenitor cells were isolated, free of macrophages and hematopoietic cells. A variety of techniques were used to identify the isolated cells as a multi-differentiated mesenchymal cell lineage co-expressing genes specific for multiple mesenchymal cell lineages including adipocytes, osteoblasts, fibroblasts and muscle cells.

Evidence that this multi- or pluri-differentiated mesenchymal progenitor cell is capable of supporting hematopoiesis is shown by the expression of a number of hematopoietic growth factors and extracellular matrix receptors. The SCID mouse experimental data provides evidence that since the MPCs can be purified to near homogeneity (95%) with relative ease, MPCs can be of value for enhancing engraftment of hematopoietic stem cells and bone marrow transplants. Additionally, increased survival rate in the SCID mouse model indicates that isolated MPCs can also be useful for the treatment of GvHD. An example of the administration of bone marrow cells and MPCs to breast cancer patients treated with chemotherapy is also provided.

A stepwise genomics strategy and an example of the genomic changes observed in leukemia associated MPCs is also provided. Cluster analysis was performed to show gene expression patterns in isolated MPCs of a normal individual and individuals with different leukemic conditions. The approach presented provides the basis for a new more objective means to diagnose patients suffering from leukemic conditions.

Example 1

Figure 1:
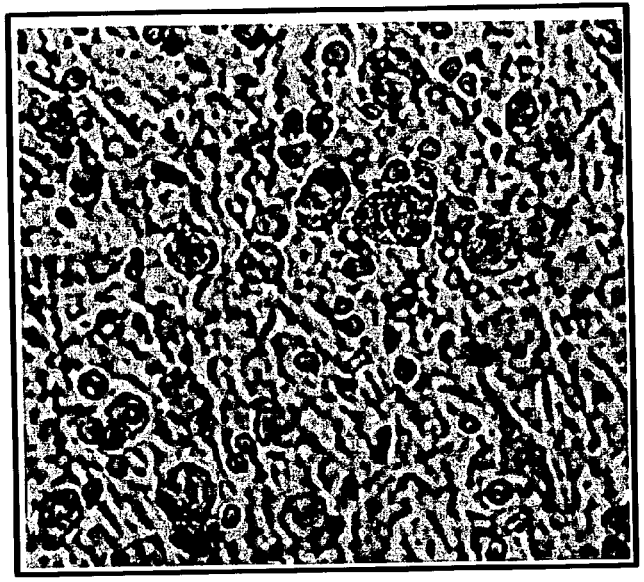
FIG. 1 is a photograph showing the phase contrast photomicrograph view of a Dexter-type stromal cell monolayer reflecting on cellular complexity.

Isolation and Characterization of MPCs from Dexter-Type Bone Marrow Stromal Cell Culture Systems Bone Marrow Culture:

Bone marrow samples were obtained from posterior superior iliac crest under general anesthesia for standard marrow transplantation. Marrow stromal cell cultures were set up using the residual cells recovered from the filters of Fenwal Bone Marrow Collection System after complete filtration, of the marrow samples. The filters were rinsed with phosphate-buffered saline without $Ca^{2+}$ and $Mg^{2+}$ (PBS-CMF). The cell suspension was subjected to Ficoll gradient isolation of the mononuclear cells (bone marrow MNCs). The bone marrow MNCs were washed (×2) in PBS-CMF and suspended in McCoy's 5A with HEPES medium containing 12.5% fetal bovine serum (FBS), 12.5% horse serum, 1 µM/L hydrocortisone and 1% penicillin/streptomycin (for this study McCoy's complete medium) and cultured under standard stromal-cell culture conditions (FIG. 1) (Seshi, et al. *Blood* 83, 2399 (1994) and Gartner, et al. *Proc Natl Acad Sci USA* 77, 4756 (1980). After two weeks, confluent stromal cell cultures were trypsinized (first passage), followed by splitting each T75 flask into two T150 flasks.

Morphologic and Phenotypic Characteristics of MPCs as Uncovered by Staining for Representative Mesenchymal Cell Lineage Markers:

Two weeks after the first passage (above), confluent stromal cells were again trypsinized. Cytospins were prepared using aliquots of unfractionated cells for performance of various cytological, cytochemical and immunocytochemical stains.

Reactivity patterns of the bone marrow culture cells are outlined in Table 1. FIGS. 4A–E illustrate morphologic and phenotypic characteristics, as uncovered by staining for representative cell lineage markers. As illustrated in Table 1 and FIGS. 3 and 4A, Wright-Giemsa staining revealed three morphologically identifiable cell populations in Dexter type stromal cell cultures, macrophages, hematopoietic cells, and nonhematopoietic cells (labeled 4, 3, and 5, respectively).

The identity of macrophages was confirmed by immunostain using anti-CD68 antibody (FIG. 4B) and cytochemical stains for acid phosphatase and Sudan black. The identity of hematopoietic cells (including macrophages) was confirmed by immunostain using anti-CD45 antibody (FIG. 4C).

The remaining nonhematopoietic cells stained intensely positive for Periodic acid-Schiff, which was diastase sensitive, signifying the presence of large stores of glycogen (FIG. 4D). The presence of glycogen (6) was confirmed by electron microscopy (see FIG. 5). In this respect, MPCs are reminiscent of the glycogen-laden reticular cells in the developing bone marrow of human fetuses (observed by L-T. Chen, L. Weiss, *Blood* 46, 389 (1975)). Glycogen deposition is viewed to be a developmentally regulated process during morphogenesis (H. Ohshima, J. Wartiovaara, I. Thesleff, *Cell Tissue Res.* 297, 271 (1999)).

In terms of lineage markers, up to 100% of the nonhematopoietic cells expressed two fat cell markers (Nile Red (FIG. 4E) and Oil Red O); an osteoblast marker (alkaline phosphatase (FIG. 4F)); and two fibroblast markers (fibronectin (FIG. 4G) and prolyl-4-hydroxylase). Greater than 85% of the nonhematopoietic cells were also positive for a muscle marker, actin (FIG. 4H). There was no evidence of expression of endothelial cell differentiation, as judged by immunohistochemical staining for CD34 and CD31 (data not shown).

The results indicate that the nonhematopoietic cells of the Dexter cultures are in fact a single, pluri-differentiated cell type co-expressing multiple mesenchymal cell lineage markers. The pluri-differentiated mesenchymal progenitor cells reported here are to be distinguished from the pluri-potential, but undifferentiated, MSCs that are generated in the absence of hematopoietic cells, such as in Friedenstein-type cultures.

TABLE 1

Reactivity patterns of bone marrow stromal cells based on cytological, cytochemical and immunocytochemical stains*,***

| | Figure | Test Utilized | Macrophages | Hematopoietic cells | Mesenchymal progenitor cells |
|---|---|---|---|---|---|
| 1 | 3 and 4A | Wright-Giemsa (Harleco) | Large cells with a small round nucleus & foamy cytoplasm: 35% of total cells | Small cells with minimal amount of cytoplasm: 5% of total cells | Large cells with a relatively irregular nucleus & cytoplasm compartmentalized into ectoplasm and endoplasm: 60% of total cells |
| 2 | 4D | Periodic acid-Schiff (PAS) (Sigma) | 0 | 0 | ~100% MPCs: staining restricted to ectoplasm in a ring-like fashion; and completely abolished by diastase digestion |
| 3 | 4C | CD45 (Dako, PD7/26 & 2B11) | 100% macrophages (MΦ) | 100% HCs | 0 |
| 4 | 4B | CD68 (Immunotech, clone PG-M1) | 100% MΦ | 0 | 0 |
| 5 | | Sudan Black (Sigma) | ~100% MΦ | 0 | 0 |
| 6 | | Acid phosphatase (Sigma kit No. 387) | 100% MΦ; positive granules packed throughout cytoplasm | 0 | 100% MPCs; positive granules in moderate amounts; staining restricted to endoplasm |
| 7 | 4E | Nile Red (Sigma) | 0 | 0 | ~100% MPCs: staining restricted to endoplasm |
| 8 | | Oil Red O (Sigma) | 0 | 0 | ~95% MPCs: variable number of positive granules; staining preferentially in the endoplasm |
| 9 | 4F | Alkaline phosphatase (Sigma Kit No. 85) | 0 | 0 | ~100% MPCs: variable number of positive granules; staining restricted to endoplasm & plasma membrane** |
| 10 | 4G | Fibronectin (Immunotech, clone 120.5) | 0 | 0 | ~100% MPCs: staining restricted to endoplasm |

TABLE 1-continued

Reactivity patterns of bone marrow stromal cells based on cytological, cytochemical and immunocytochemical stains*,***

| Figure | Test Utilized | Macrophages | Hematopoietic cells | Mesenchymal progenitor cells |
|---|---|---|---|---|
| 11 | Prolyl-4-hydroxylase (Dako, clone 5B5) | 0 | 0 | ~100% MPCs: staining preferentially in the endoplasm |
| 12 4H | Muscle actin (Ventana, clone HUC 1-1) | 0 | 0 | >85% MPCs: variable staining restricted to ectoplasm |

*The lineages of the markers tested above are: 3, hematopoietic cell marker; 4, 5 and 6, monocyte/macrophage markers; 7 and 8, adipocyte markers; 9, osteoblast marker; 10 and 11, fibroblast markers; 12 muscle marker.
**One earlier study (Simmons, et al., Nature 328, 429–432) interpreted the localization of alkaline phosphatase staining as confined to the plasma membrane when in fact it is predominately present within the endoplasm (compare FIG. 1C of this reference with FIG. 4F).
***While well-accepted mesenchymal lineage markers were used, these markers do not necessarily lend themselves to simultaneous assessment of the same cell. For example, muscle-specific actin antibody worked only on formalin-fixed, paraffin embedded material, whereas stains like alkaline phosphatase, Oil Red and Nile Red are not anti-body based and involve varying fixing and staining conditions. Thus, the evidence shows that close to 100% of members of a morphologically distinct populationexpress multiple lineage markers of interest.

Bone Marrow Mesenchymal Progenitor Cell (MPC) Purification:

To further investigate the characteristics of the MPCs, the nonhematopoietic stromal cells were then purified from the macrophages (~95% pure), the dominant "contaminating" cell type using the following method. Confluent monolayers of stromal cells resulting from first passage, above, were washed for three minutes in $Ca^{2+}/Mg^{2+}$ free Hanks' balanced salt solution. Cells were incubated at room temperature for 45 minutes with intermittent mixing in serum-free McCoy's medium containing 10 mM L-leucine methyl ester (LME, Sigma). LME is a lysosomotropic agent that selectively kills and detaches macrophages. The detached macrophages were removed by washing the monolayers twice in McCoy's complete medium, followed by trypsinization of the monolayers. The resulting single cell suspensions were fractionated by discontinuous Percoll gradient (70%, 50%, 30%, 20%, 10%) centrifugation at 800×G for 15 minutes at 4° C. in a fixed angle rotor (Avanti-J25 Beckman centrifuge) (FIG. 2). Low-density cells representing the macrophages resistant to detachment by LME separate as a band at the interface of serum and 10% Percoll and were discarded (1). High-density nonhematopoietic cells representing MPCs form a layer in the region of 30–50% Percoll (2). These were collected and washed twice by centrifugation through PBS-CMF. This protocol is conservatively expected to yield, >2.5×10$^6$ MPCs per T-150 flask (i.e., >50×10$^6$ MPCs per batch of 20 flasks). The purity of these preparations, typically about 95%, was routinely monitored by Wright-Giemsa staining.

Northern Blotting:

Additional sets of multiple mesenchymal lineage markers were assessed by Northern blotting to eliminate any observer bias that might be inherent in morphological assessment. FIGS. 6A–M represent different gene probes used for hybridization. The sources of the gene probes employed and the major transcripts observed are outlined in the brief description of the figures.

Total RNA was prepared by dissolving the high-density cell pellets in Trizol (Life-Technologies). Total RNA samples from unfractionated stromal cells and BM MNCs were similarly prepared. The RNA samples were electrophoresed in a standard 1% agarose gel containing 2% formaldehyde in MOPS/EDTA buffer and blotted onto Immobilon-Ny+ membrane. Probes were labeled using Prime-A-Gene Kit (Promega) and $a^{32}P$ dCTP (NEN). Hybridization was performed at 65° C. in modified Church's hybridization solution using 3×10$^6$ counts/ml in 10 ml (Millipore, 1998).

In FIGS. 6A–M, Northern blot analysis was performed side-by-side on fractionated stromal cells, non-hematopoietic cells freed of macrophages, and initial bone marrow mononuclear cell samples. Lanes 1 and 2 represent total RNA samples (10 µg each) from unfractionated stromal cells (subjects S1 and S2, respectively). Lanes 3 and 4 represent total RNA samples (10 µg each) from purified stromal MPCs (subjects S1 and S2, respectively). Lanes 5 and 6 represent total RNA samples (10 µg each) from bone marrow mononuclear cells, the starting cells for bone marrow cell cultures (subjects S3 and S4, respectively).

The large transcripts, especially of collagen (lane 1, FIG. 6G) and fibronectin (lane 1, FIG. 6J), in RNA extracted from unfractionated stromal cells of subject 1 showed difficulty migrating into the gel. This observation correlates with the presence of an artifact of unresolved positive material in lane 1, FIG. 6A. Since the RNA extracted from unfractionated stromal cells of the subject 2 did not present this problem (lane 2, FIG. 6G, FIG. 6J and FIG. 6A), the observation does not impact on the overall interpretation of the results (see text). The lineages of markers tested were: monocyte/macrophage markers, CD68 and cathepsin B; adipocyte marker, adipsin; osteoblast markers, osteoblast-specific cadherin-11, chondroitin sulfate proteoglycan 2, collagen type I alpha 1 and decorin; fibroblast marker, fibronectin; muscle markers, caldesmon and transgelin. Marker signals were normalized to the amount of RNA loaded, which was based on densitometry of the GAPDH signals on the corresponding blot (Bio-Rad Model GS-700 Imaging Densitometer). Attenuation or enhancement of the marker signals in the purified stromal MPCs (i.e., lanes 3 and 4) relative to unfractionated stromal cells (i.e., lanes 1 and 2, respectively) is shown as fold Δ (decrease/increase) underneath the lanes 3 and 4; ND, means not determined.

The purity of the nonhematopoietic cells was demonstrated by a near complete absence of two macrophage markers, CD68 and cathepsin B (as shown by Northern blotting data, FIGS. 6A and 6B). As a positive control, bone marrow mononuclear cells rich in myelomonocytic cells abundantly expressed CD68 (lanes 5 & 6, FIG. 6A). The Northern blot results are consistent with a purity estimate of ~95% (vs. 60% in unfractionated samples) based on morphology and immunocytochemical staining for CD68.

Compared to unfractionated cells, the purified nonhematopoietic cells expressed significantly higher levels of markers representing fat cells (adipsin, FIG. 6D); osteoblasts (osteoblast-specific cadherin-11, chondroitin sulfate, collagen type 1 and decorin, FIGS. 6E–H); fibroblasts (fibronectin, FIG. 6J); and smooth muscle cells (caldesmon and transgelin, FIGS. 6K–L).

No trace of osteoblast, fibroblast, or smooth muscle cell markers were detected in the bone marrow mononuclear cells, suggesting a less than detectable level of stromal cells or their precursors in bone marrow mononuclear cells. However, the fat cell marker, adipsin, was detected in all samples including the bone marrow mononuclear cells.

Taken together, the morphologic, cytochemical and immunocytochemical results (FIG. 4A–H and Table 1), and the Northern blotting data (FIG. 6A–M) indicate that the nonhematopoietic stromal cells of the Dexter cultures co-express markers specific for at least four different mesenchymal cell lineages.

This finding is especially intriguing because pluri-differentiation is often a feature of neoplastic cells (Brambilia and Brambilia, *Rev. Mal. Respir.* 3,235 (1986); Pfeifer et al., *Cancer Res.* 51, 3793–3801 (1991); Tolmay et al., *Virchow's Arch* 430, 209–12 (1997). However, a cytogenetic analysis of the Percoll-gradient purified MPCs showed a normal GTW banding pattern.

RT-PCR Analysis for expression of representative hematopoietic growth factors and extracellular matrix receptors by MPCs RT-PCR was conducted in a total reaction volume of 100 μl using 2 μg each of total RNA; corresponding primers; and a master mix of the PCR reagents. The RT conditions included sequential incubations at 42° C. for 15 minutes, 99° C. for five minutes, and 5° C. for five minutes. The PCR conditions included: initial melting at 94° C. for four minutes; and cyclical melting at 94° C. for 45 seconds, annealing at 55° C. for 45 seconds and extension at 72° C. for 45 seconds with 34 cycles. PCR was terminated after final extension at 72° C. for ten minutes. Reaction products (G-CSF, SCF, each 25 μl; VCAM-1, ALCAM, each 50 μl; ICAM-1, 75 μl) were concentrated as necessary; electrophoresed along with a 100-bp DNA ladder (GIBCO-BRL) in a standard agarose (1%) gel in TAE buffer; and stained with ethidium bromide.

Figure 6:
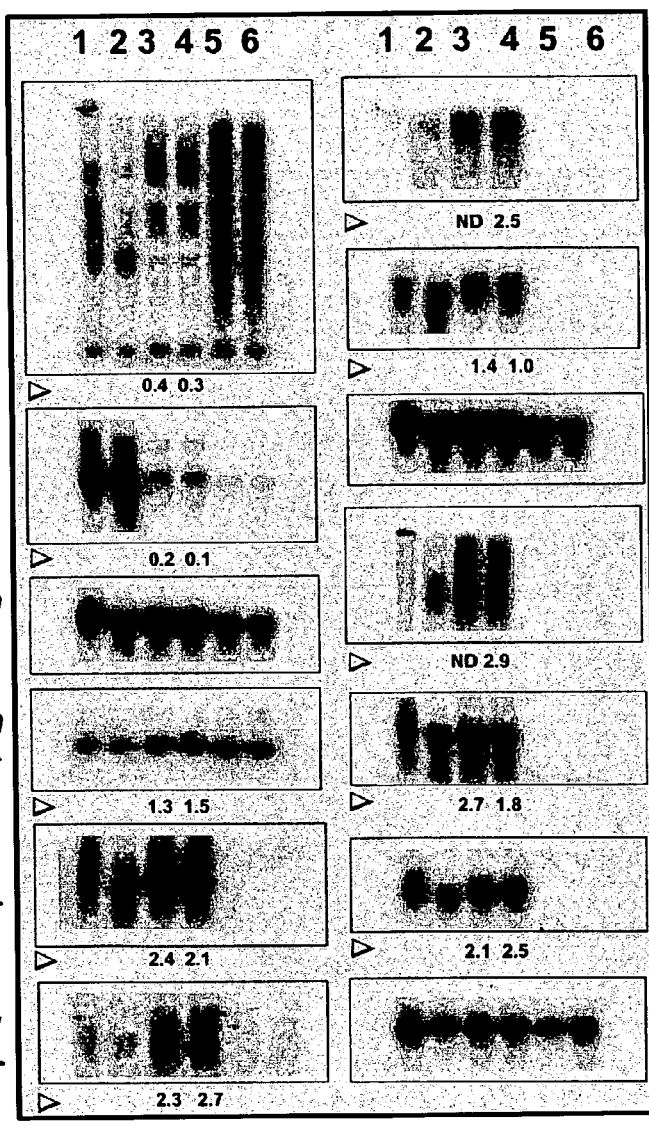
FIG. 6A–M are photographs which show Northern blot analysis of bone marrow stromal cell RNAs for expression of genes specific for multiple mesenchymal cell lineages.

PCR products, shown in FIG. 7 lanes labeled 1–2, were generated using aliquots of the same RNA samples from purified stromal MPCs, as used for Northern blotting shown under FIG. 6 lanes 3 and 4 respectively. The gene transcripts amplified were as follows: G-CSF (granulocyte-colony stimulating factor); (Tachibana et al., *Br. J. Cancer*, 76, 163–74 (1997); SCF (stem cell factor, i.e., c-Kit ligand); (Saito et al., *Biochem, Biophys. Res. Commun.*, 13, 1762–69 (1994) ICAM-1 (intercellular adhesion molecule-1, CD54) and VCAM-1 (vascular cell adhesion molecule-1, CD106) (primers from R&D); and ALCAM (activated leukocyte cell adhesion molecule, CD166) (Bruder et al., *J. Bone Miner. Res.*, 13, 655–63 (1998)).

The observed PCR products for G-CSF (600 bp, i.e., the top bright band) and ALCAM (175 bp) were significantly different from the expected sizes (278 bp; 372 bp, respectively). However, sequencing of the gel-purified PCR bands and subsequent BLAST search showed a 99–100% identity with respective members. Attempts to detect c-Kit (i.e., SCF receptor) using primers as described (Saito et al., *Biochem, Biophys. Res. Commun.*, 13, 1762–69 (1994)) amplified a PCR product of ~300 bp with no homology to c-Kit (data not shown). The observed product sizes for SCF (~730 bp); ICAM-1 (~750 bp); and VCAM-1 (~500 bp) were as expected.

As illustrated in FIG. 7, RT-PCR analysis showed that purified, multi-differentiated MPCs express both critical hematopoietic growth factor/cytokines, such as G-CSF and SCF as well as matrix receptors/hematopoietic cell adhesion molecules, i.e. ICAM-1, VCAM-1, and ALCAM.

Example 2

Figure 8:
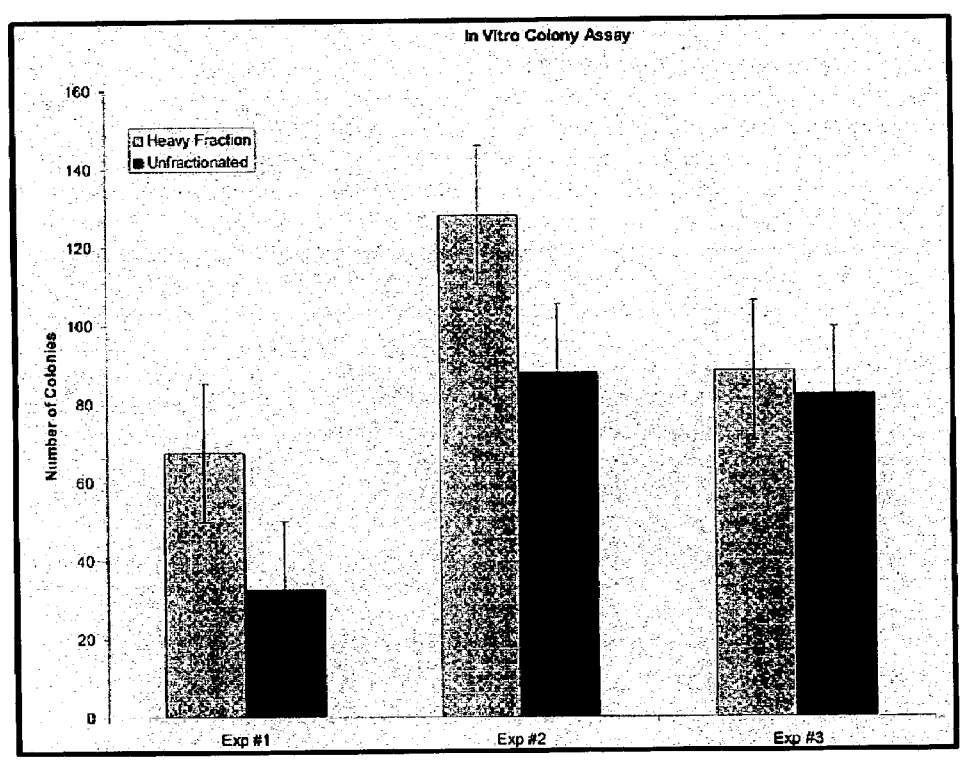
FIG. 8 is a graph comparing of the ability to support in vitro hematopoiesis by the purified MPCs (heavy fraction represented by gray) of the present invention vs. unfractionated bone marrow stromal cells (represented by black).

Comparison of the Ability to Support In Vitro Hematopoiesis by Purified MPCs vs. Unfractionated Bone Marrow Stromal Cells CD34+ positive cells (hematopoietic progenitor cells) were purified (Dynal kit) and cocultured with irradiated stromal monolayers for five weeks, followed by performance of standard colony assays for hematopoietic progenitors using methylcellulose medium supplemented with colony stimulating factors (using MethoCult medium from Stem Cell Technologies, Inc, Canada). Unfractionated bone marrow stromal cells and purified MPCs were prepared in the same manner as in Example 1. Data in FIG. 8 represents results from three experiments. Purified MPC provides increased preservation of hematopoietic progenitor cells compared to unfractionated stromal cells.

Example 3

Animal Model for Enhanced Engraftment Capacity of MPCs

The Severe Combined Immunodeficiency Disease (SCID) mouse model is an ideal system in which to investigate MPC function. Engraftment of human hematopoietic progenitors in SCID mice requires either coadministration of exogenous human cytokines, or cotransplantation of human bone marrow plugs or bone fragments.

There has been discovered a convenient, new source for human bone marrow stromal cells for enhancing transplantation that does not require cytokines, bone fragment, or marrow. Unlike prior methods, the isolated cells of the present invention support human hematopoiesis in the SCID mouse model as effectively as whole marrow stroma. The transplantation of human marrow mononuclear cells combined with purified MPCs results in dramatically vigorous engraftment of human cells in spleen, bone marrow, liver, pancreas, lungs, stomach, and paravertebral neuronal ganglia of SCID mice. By contrast, mice receiving human bone marrow mononuclear cells alone or MPCs alone expectedly showed no detectable evidence of human hematopoietic cell engraftment. Also notably, the mortality rate was highest in mice that received unfractionated whole marrow stroma whereas purified MPC increased the survival rate which can be due to reduction in GvHD.

Transplantation of Human Cells in SCID Mice:

Homozygous CB-17 scid/scid mice, six to eight weeks of age, were used. Lyophilized anti-asialo GM1 rabbit antibody (Wako Chemicals) was suspended in 1 ml sterile $ddH_2O$, followed by pretreatment of mice with an IP injection of 20 ml (600 mg) ASGM1 antibody (to specifically deplete mouse macrophages and NK cells). Alternatively, one could use NOD/SCID mice lacking NK cell function, however, in light of highly promising preliminary results it was elected to continue use of scid/scid mice. The antibody treatment schedule included four-hour pre-engraftment and every seven days thereafter for the duration of the experiment. On the day of transplantation, the mice were irradiated with 200 or 300 cGy gamma-irradiation from a $^{137}Cs$ source. Approximately $2.5 \times 10^6$ MPCs suspended in 0.5 ml McCoy's medium and/or $25 \times 10^6$ MNCs suspended in 0.2 ml were injected per mouse, intraperitoneally. Hematopoietic cell engraftment was assessed after five weeks by harvesting and analyzing representative hematopoietic and nonhematopoietic organs including blood, spleen, bone marrow (from two femurs and tibia) from euthanized mice.

Flow Cytometric Evidence

Figure 9A:
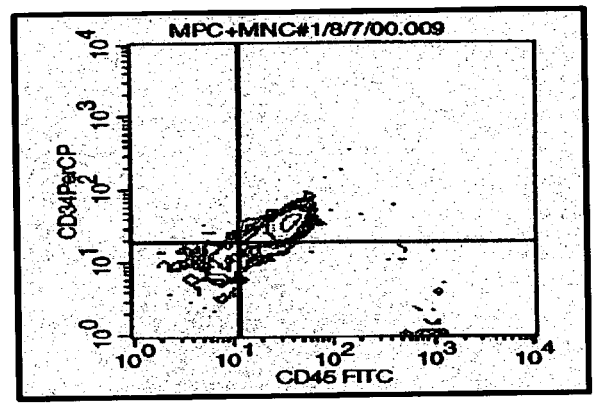
FIG. 9A and FIG. 9B are graphs showing flow cytometric evidence of human hematopoietic cell engraftment in a SCID mouse cotransplanted with the MPCs of the present invention.
Figure 9B:
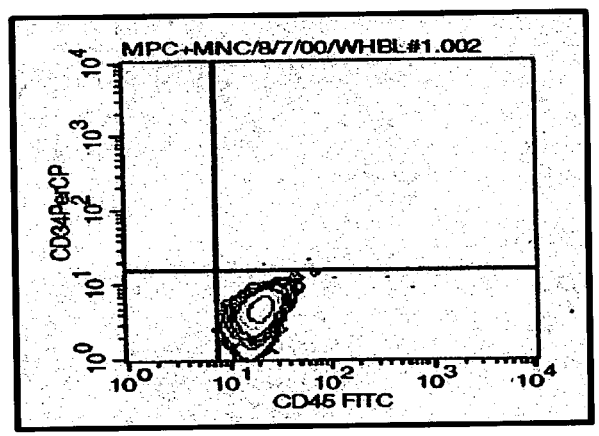

FIGS. 9A and 9B are flow cytometric evidence of human hemopoietic cells in a SCID mouse cotransplanted with marrow MPC. FIG. 9A shows the presence of CD45+/CD34+ progenitors in the marrow. FIG. 9B shows CD45/CD34– mature hematopoietic cells circulating in the mouse's blood.

Photomicrographs of Cells

Figure 10A:
FIGS. 10A–H are photographs which show engraftment of human hematopoietic cells in a SCID mouse cotransplanted with the purified marrow MPCs of the present invention.
Figure 10B:
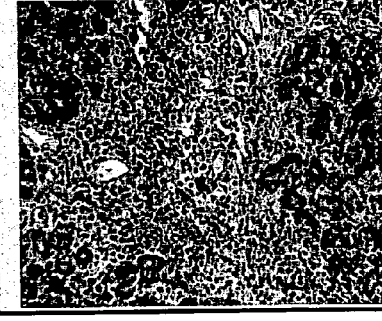
Figure 10C:
Figure 10D:
Figure 10E:
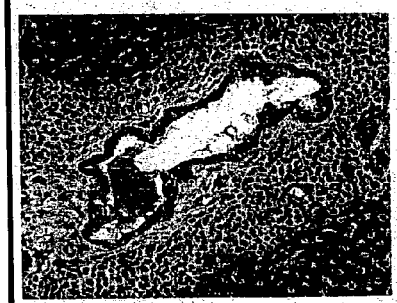
Figure 10F:
Figure 10G:
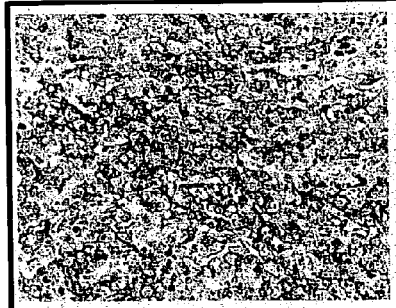
Figure 10H:
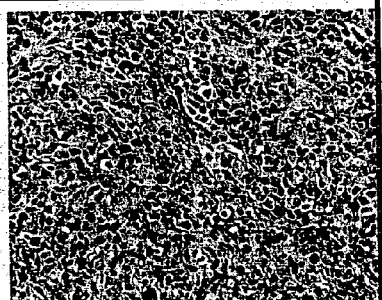

FIGS. 10A–H shows engraftment of human hematopoietic cells in a SCID mouse cotransplanted with the purified marrow MPCs of the present invention. FIG. 10A shows a serial section of a mouse spleen stained with H & E. FIG. 10B shows a serial section of a mouse spleen stained with immunoperoxidase stain for CD45. FIG. 10C shows bone marrow stained for CD45. FIG. 10D shows a serial section of the mouse liver stained with H&E depicting involvement of periportal areas. FIG. 10E shows a serial section of the mouse stomach stained with H&E showing transmural infiltration. FIG. 10F shows a serial section of the mouse lung stained with H&E showing involvement of peribronchial area. FIG. 10G shows a serial section of the mouse pancreas stained with H&E. FIG. 10H shows a serial section of the mouse paravertebral ganglia stained with H&E.

Figure 11A:
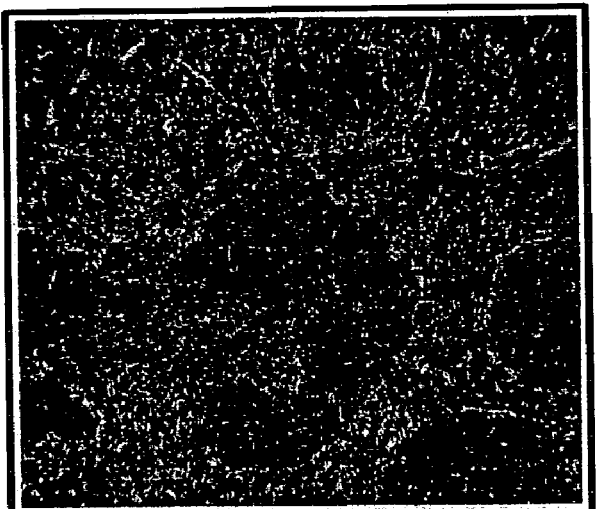
FIG. 11A is a photomicrograph of a serial section of the spleen of a normal BALB/C mouse showing white pulp populated by darkly staining lymphocytes (H&E).
Figure 11B:
FIG. 11B is a photomicrograph of the spleen of a SCID mouse showing white pulp largely consisting of lightly staining stromal framework (H&E).
Figure 11C:
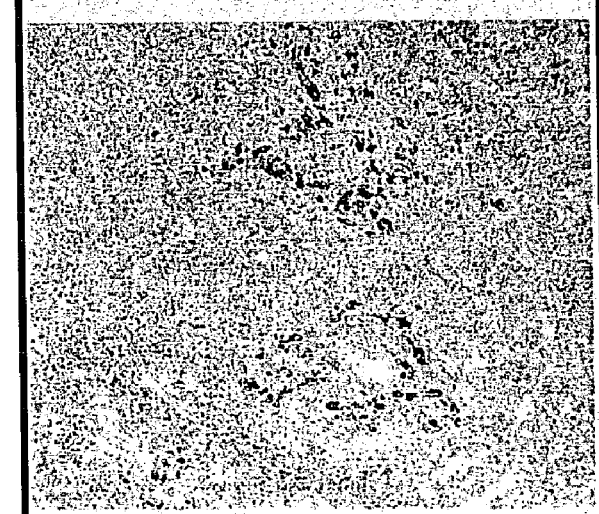
FIG. 11C is a photomicrograph of the spleen of a SCID mouse cotransplanted with human bone marrow MNC and the purified bone marrow MPCs of the present invention showing homing (engraftment) of human B cells to white pulp.

FIG. 11A is a photomicrograph of a serial section of the spleen of a normal BALB/C mouse showing white pulp populated by darkly staining lymphocytes (H&E). FIG. 11B is a photomicrograph of the spleen of a SCID mouse showing white pulp largely consisting of lightly staining stromal framework (H&E). FIG. 11C is a photomicrograph of the spleen of a SCID mouse cotransplanted with human bone marrow MNC and the purified bone marrow MPCs of the present invention showing homing (engraftment) of human B cells to white pulp.

Southern Blotting Data

Figure 12A:
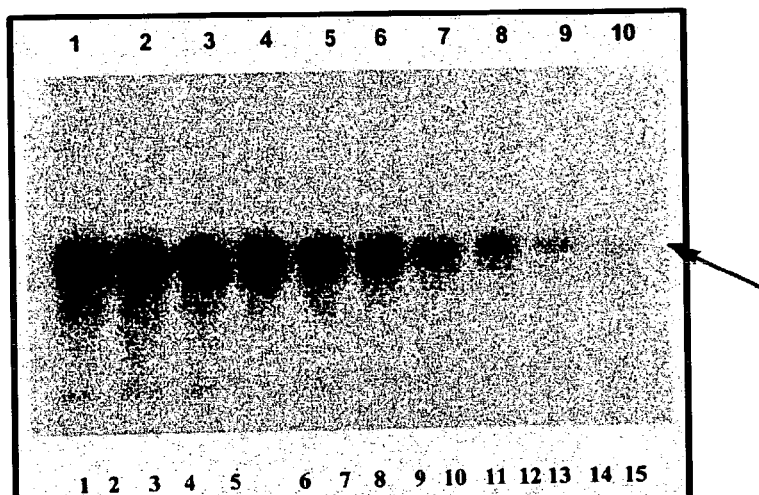
FIGS. 12A–C are photographs which show Southern blotting data.

Hybridization of sample DNA using a DNA probe specific for human chromosome 17 alpha satellite DNA (p17H8) shows linear signal intensity with a 2.7 Kb band (arrow; autoradiogram exposed for only 45 minutes) (FIG. 12A). Lanes 1–10 contain human DNA starting 1000 ng to 100 ng admixed with 0 ng 900 ng of mouse DNA, total amount DNA loaded in each lane being 1 ug, allowing construction of a standard curve. The reported limit of detection with this technique is 0.05% human cells, which is more reliable than flow cytometry in detecting very low levels of human cell engraftment.

Figure 12B:
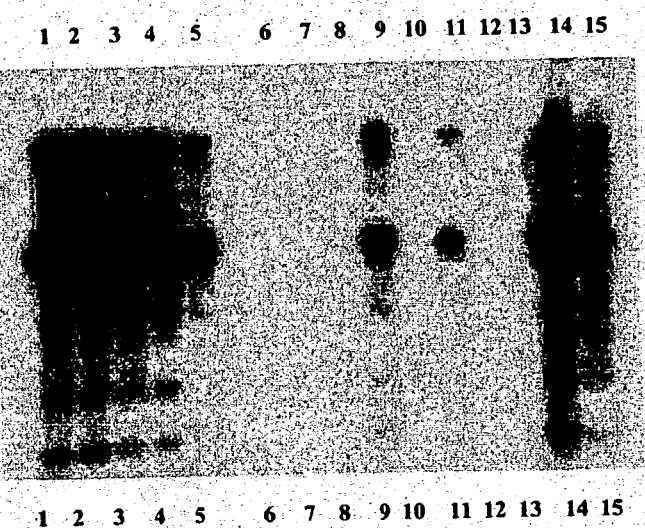

FIG. 12B is a Southern blot of EcoR1 digest of thymic genomic DNA from SCID mice. Lanes 1–5 were loaded with 500 through 100 ng human DNA. Lanes 6, 9–11 were loaded with DNA from mice which received unfractionated bone marrow stroma plus bone marrow mononuclear cells. Lanes 7, 8, 14, 15 were loaded with DNA from mice that received MPCs plus bone marrow mononuclear cells. Lanes 12, 13 were loaded with DNA from mice that received bone marrow mononuclear cells only. There is evidence of human cell engraftment in the mouse thymus in lanes 9 and 11 and lanes 14 and 15 evidenced by the 2.7 Kb band. There was no evidence of engraftment in mice that only received only bone marrow mononuclear cells, lanes 12 and 13.

Figure 12C:
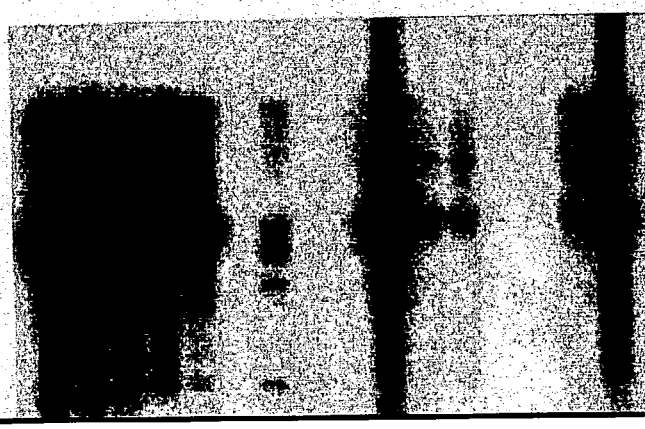

FIG. 12C is EcoR1 digest of Lymph Node genomic DNA from SCID mice. Lanes 1–5 were loaded with 500 through 100 ng human DNA. Lanes 6, 9–11 were loaded with DNA from mice which received unfractionated bone marrow stroma plus bone marrow mononuclear cells. Lanes 7, 8, 14, 15 were loaded with DNA from mice that received MPCs plus bone marrow mononuclear cells. Lanes 12, 13 were loaded with DNA from mice that received bone marrow mononuclear cells only. While there was evidence of engraftment of human cells in the mouse lymph nodes for mice that received unfractioned bone marrow stromal cells and MPCs, there was no evidence of engraftment in mice that only received only bone marrow mononuclear cells, lanes 12 and 13.

Increased Survival and Evidence of MPC Effect on GvHD

FIG. 13A and FIG. 13B show graphs comparing the survival rate and engraftment of human hematopoietic cells in SCID mice cotransplanted with the purified bone marrow MPCs of the present invention versus unpurified bone marrow stromal cells. Mice in FIG. 13A received 300 cGy irradiation dose and mice in FIG. 13B received 200 cGY of irradiation. FIG. 13A and FIG. 13B show comparable engraftment of human hematopoietic cells in SCID mice cotransplanted with purified MPCs versus unpurified bone marrow stromal cells and the markedly enhanced survival of mice receiving purified MPCs. Notably, no engraftment was observed in mice receiving bone marrow mononuclear cells alone.

The highest mortality rate, FIG. 13B, was observed in mice receiving the unpurified stromal cells and the bone marrow mononuclear cells. The increased mortality observed can be related to the presence of highly immunogenic macrophages and consequent GvHD. The mice with the highest survival rate, as shown in FIG. 13A, were the mice receiving purified MPCs and bone marrow mononuclear cells.

FIGS. 14A–C demonstrate apoptosis by TUNEL assay in organs of SCID mice that died after transplantation with human bone marrow mononuclear cells and unpurified bone marrow stromal cells. FIG. 14A shows a serial section of the liver of the mouse that survived. FIG. 14B shows a serial section of the liver of the mouse that died. FIG. 14C shows a serial section of the spleen of the mouse that survived. FIG. 14D shows a serial section of the spleen of the mouse that died. Hematoxylin counterstain was applied to sections in FIG. 14A and FIG. 14C. Methylgreen counterstain was applied to sections in FIG. 14B and FIG. 14D.

Notably, there is discrete TUNEL-positive nuclei in the liver of the expired mouse in FIG. 14B and complete absence of staining in the liver of the surviving mouse FIG.

14A. While some ill-defined globules of staining are observed in the spleen of the mouse that survived, the nuclear integrity of most of the cells is well preserved suggesting minimal or no apoptosis (FIG. 14C). By contrast, the dead mouse spleen (FIG. 14D) showed extensive TUNEL positivity precluding accurate interpretation. Control mouse liver and spleen showed results similar to those of the mouse that survived.

The size of the spleens from the mice that survived and the mice that died were compared. The dead mice were observed to have small and atrophic spleens correlating with lymphoid cell depletion and apoptosis.

The above results indicate that purified MPC can support human hematopoiesis in SCID mice as effectively as whole marrow stroma. Equally important is that the purified MPCs increased the survival rate. Evidence suggests that the increased survival can be due to a reduction in GVHD.

Example 4

Administration of Bone Marrow Cells and Mesenchymal Progenitor Cells to Breast Cancer Patients Treated with Chemotherapy A breast cancer patient undergoes a diagnostic posterior iliac crest bone marrow aspiration and biopsy using a local anesthetic. A small portion (2 to 3 ml) of the aliquot (10 to 20 ml) of marrow is submitted for routine histologic testing and determination of the presence of tumor cells using immunoperoxidase testing. The remainder of the cells are Dexter cultured for MPCs as described above in Example 1.

The patient also undergoes placement of a pheresis central venous catheter, and receives subcutaneous injections of G-CSF (filgrastin) 10 µg/kg/day as described in Peters, et al, Blood, Vol. 81, pgs. 1709–1719 (1993); Chao, et al, Blood, Vol. 81, pgs. 2031–2035 (1993); Sheridan, et al, The Lancet, Vol. 2, pgs. 891–895 (1989); and Winter, et al, Blood, Vol. 82, pg. 293a (1993). G-CSF injections begin at least three days before the first pheresis is initiated. G-CSF therapy is withheld if the white blood cell count rises above 40,000/µL and is resumed once the white blood cell count drops to less than 20,000/µL.

If the patient is receiving only G-CSF as the vehicle for "mobilization" of peripheral blood progenitor cells, the patient must not have received chemotherapy within four weeks of the planned pheresis. If the patient has received both conventional chemotherapy and G-CSF treatment for mobilization, the patient must not have received chemotherapy within ten days of the planned pheresis, and the white blood cell count must be at least 800/µL and the platelet count at least 30,000/µL.

Daily pheresis procedures are performed using a Cobe Spectra instrument (Cobe, Lakewood, Col.), and each cellular collection is cryopreserved using a controlled-rate liquid nitrogen freezer, until at least $15 \times 10^8$ mononuclear cells/kg are collected (Lazarus, et al., Bone Marrow Transplant, Vol. 7, pgs. 241–246 (1991)). Each peripheral blood progenitor cell is processed and cryopreserved according to previously published techniques. (Lazarus, et al., J. Clin, Oncol., Vol. 10, pgs, 1682–1689) (1992); Lazarus et al., (1991)).

Eight days before the patient is infused with the autologous peripheral blood progenitor cells, the patient receives chemotherapy over a period of 96 hours (four days), with the following chemotherapy agents: 1) Cyclophosphamide in a total dosage of 6 g/m$^2$ (1.5 g/m 2/day for four days) is given via continuous intravenous infusion at 500 mg/m$^2$ in 1,000 ml normal saline every eight hours; 2) Thiotepa in a total dosage of 500 mg/m$^2$/day for four days) is given via continuous intravenous infusion at 125 mg/$^2$ in 1,000 ml normal saline every 24 hours; and 3) Carboplatin in a total dosage of 1,800 mg/m$^2$ (200 mg/m$^2$/day for four days) is given via continuous intravenous infusion at 200 mg/m$^2$ in 1,000 ml of 5% dextrose in water every 24 hours.

The patient also receives 500 mg of Mesna in 50 ml normal saline IV over 15 minutes every four hours for six days (144 hours), beginning with the first dose of cyclophosphamide.

At least 72 hours after the completion of the chemotherapy, the MPCs are harvested from the Dexter culture(s). MPCs are collected and purified as described in Example 1. Cells are resuspended at approximately $10^6$ cells/ml, and injected slowly intravenously over 15 minutes to provide a total dosage of from 10 to about $5 \times 10^6$ cells.

MPCs can also be frozen and thawed to use when needed. For example, unfractionated cells from a Dexter culture are frozen. Upon thawing the cells are plated for about two days. The MPCs are then purified as in Example 1 above. The MPCs are then replated with serum or in a serum free media and can remain stable for up to six days.

The day after the patient receives the MPCs, the frozen autologous peripheral blood progenitor cells are removed from the liquid nitrogen refrigerator, transported to the patient in liquid nitrogen, submersed in a 37° C. to 40° C. sterile water bath, and infused rapidly intravenously without additional filtering or washing steps. GM-CSF in an amount of 250 µg/m$^2$ then is given as a daily subcutaneous injection, beginning three hours after completion of the autologous blood progenitor cell infusion. The GM-CSF is given daily until the peripheral blood neutrophil count exceeds 1,000/µL for three consecutive days.

Example 5

Genomic Changes Observed in Leukemia Associated MPCs

The following is one example of how normal hematopoiesis might be compromised in leukemic conditions. The cellular interactions that underlie leukemic bone marrow involve stromal cells, leukemia/lymphoma cells, and normal hematopoietic pro genitors (including those of myelopoiesis, erythropoiesis and megakaryocytopoiesis). In addition to displacing normal hematopoietic cells, the leukemia/lymphoma cells can potentially cause direct damage to the hematopoietic supportive stromal cells by inducing unwanted gene expression profiles and adversely affecting the normal hematopoiesis. The cellular interactions can be schematized as:

Leukemia/lymphoma cells ⇌ stromal cells ⟶ normal hematopoietic progenitors.

The point of this scheme is that regardless of whether stromal cell lesions are primary or secondary to leukemogenesis, the normal hematopoietic function is invariably compromised in leukemic conditions, though different leukemias affect myelopoiesis, erythropoiesis and megakaryocytopoiesis differentially. Contrary to the prevailing notion (see Marini, F et al., Mesenchymal Stem Cells from Patients with Chronic Myelogenous Leukemia Patients can be Transduced with Common Gene Transfer Vectors at High Efficiency, and are Genotypically Normal, 42$^{nd}$ Annual Meeting of the American Society of Hematology, Dec. 1–5, 2000 Poster #665), there has been observed extensive and striking gene expression changes in leukemia-associated bone marrow MPCs by using high-resolution genomics. Therefore, one embodiment of the present invention is to use transplantation of tissue-culture expanded, purified normal MPCs to improve granulopoiesis, erythropoiesis and thrombopoiesis, in for example MDS (most of MDS patients do not die from blast transformation but from complications related to cytopenias, i.e., hematopoietic failure).

The studies targeted acute myeloid leukemia (AML), chronic myeloid leukemia (CML) and multiple myeloma (MM), one case of each. The AML patient was a 57 year-old woman with 52% myeloblasts in the bone marrow with immunophenotype confirmed by flow cytometry and a karyotypic abnormality of 45, XX, −7(6)/46, XX [6]. Together with morphology, the diagnosis was AML arising in a background of myelodysplasia. The CML patient was a 35 year-old man with 2% blasts in the bone marrow and karyotypic abnormalities of Philadelphia chromosome and BCR/ABL gene rearrangement. Together with morphology, the diagnosis was CML in chronic phase. The MM patient was a 61 year-old woman with a IgA myeloma. The serum IgA level was 2.4 g/dl and the marrow plasma cell count was 37%. None of the patients was treated prior to obtaining marrow samples used in this study, to avoid any therapy-induced changes complicating the disease-associated changes.

The leukemic samples consisted of marrow aspirates that remained unused after clinical diagnostic studies were preformed. A bone marrow sample obtained from an adult healthy male who had consented to donate bone marrow for standard marrow transplantation was simultaneously studied. The normal bone marrow sample consisted of residual cells recovered from the filters after complete filtration of the marrow sample. Setting up of Dexter-type stromal cell cultures and isolation of MPC were as described in Example 1. The normal stromal cells were studied without and after stimulation with TNFα because TNFα (and IL-4) are regarded as negative regulators of hematopoiesis. Notably these cytokines, especially TNF α, are elevated in marrow plasma of patients with myelodysplastic syndromes (MDS), the clinical hallmarks of which are anemia, leukopenia and thrombocytopenia (i.e., pancytopenia). TNFα and IL-4 are considered possible mediators of hematopoietic dysregulation typical of MDS.

A Stepwise Genomics Strategy Encompassed:

Preparation of total RNA from MPC samples→generation of cDNA→preparation of ds DNA→in vitro transcription into cRNA→fragmentation of cRNA→hybridization of target RNA to a microarray of known genes (Affymetrix genechip containing DNA from ~12,000 known human genes, e.g., U95A oligonucleotide microarray)→analysis of differentially expressed genes using an appropriate software (GeneSpring) to discern the patterns of gene expression or genomic signatures by a given MPC type.

Cluster Analysis Showing Gene Expression Patterns in Bone Marrow MPC Isolated from a Normal Individual and Patients with Different Leukemic Conditions.

Genes with correlated expression across bone marrow MPC types: GeneSpring was used for cluster analysis. Prior to application of an agglomerative hierarchical clustering algorithm, microarray signals were normalized across experiments (i.e., from one MPC type to another) making the median value of all of measurements unity, so different experiments are comparable to one another. The signals were also normalized across genes in order to remove the differing intensity signals from multiple experimental readings. Genes that are inactive across all samples were eliminated from analysis. Notably, 7398 genes out of 12,626 genes (present on the Affymetrix genechip used) passed the filter of a normalized signal intensity of at least 0.1 across at least one of the five experiments performed. Cluster analysis was performed with standard correlation (same as Pearson correlation around zero) as the distance metric, a separation ratio of 0.5 and a minimum distance of 0.001 as provided by the software application. A closer relationship between CML- and MM-associated MPCs was observed, which in turn are related to AML-associated MPC, thus transforming global patterns of gene expression into potentially meaningful relationships.

Two-dimensional cluster analysis of tissue vs. gene expression vectors: A gene tree was constructed. Genes cluster near each other on the "gene tree" if they exhibit a strong correlation across MPC experiments and MPC tree branches move near each other if they exhibit a similar gene expression profile. The data indicated that the two-way clustering readjusted the location of a number of genes resulting in accentuation of genomic signatures of each cell type. Investigators can usefully catalog genes composing any unique or signature cluster of interest by creating a gene list and disclosing their identities.

Self-Organizing Map (SOM) Clusters (6×5) Show Differential Gene Expression in Bone Marrow MPC Isolated from Different Hematopoietic Conditions.

Generation of SOM clusters involved prior normalization and filtering of the data. SOM algorithm was applied as provided by GeneSpring. Visualization of SOM clusters in combination with hierarchical clustering (i.e., MPC tree) revealed correlated meaningful patterns of gene expression. Predicated on the basis of SOM operating principle, the related SOM clusters tend to be located physically close to each other. For example, the juxtaposition of the SOM clusters with the common denominator containing genes that are up-regulated in AML/MDS-associated MPC. Whole or part of any SOM cluster can be selected to make a gene list providing the identities of the genes involved.

Genes Highly Expressed in Normal MPC but Absent or Minimally Expressed in Leukemia-Associated MPC Lists of genes that are down-regulated in leukemia-associated MPC (AML/MDS, CML and MM) were created in comparison to normal MPC. A Venn diagram was made using these three gene lists. GeneSpring allows creation of sublists of genes corresponding to union, intersection and exclusion. Transcriptional profiles of any of these sublists of genes can be visualized across MPC samples of interest. The following is one such sublist of genes containing genes that are highly expressed in normal MPC and down-regulated in leukemia-associated MPCs revealing the identity of the subset of genes of interest: putative, wg66h09.x1 Soares *Homo sapiens* cDNA clone, *Homo sapiens* mRNA for CMP-N-acetylneuraminic acid hydroxylase, *Homo sapiens* cDNA clone DKFZp586G0421 (symptom: hute 1), Human mRNA for histone H1x, Putative monocarboxylate transporter *Homo sapiens* gene for LD78 alpha precursor, Interacts with SH3 proteins; similar to c-cbl proto-oncogene product, wg82b12.x1 Soares *Homo sapiens* cDNA clone, Human atrial natriuretic peptide clearance receptor (ANP C-receptor) mRNA, Human 71 kDa 2'5' oligoadenylate synthetase (p69 2-5A synthetase) mRNA, *Homo sapiens* hMmTRA1b mRNA, Human GOS2 protein gene, Preproenkephalin, Human guanylate binding protein isoform I (GBP-2) mRNA, Human gene for hepatitis C associated microtubular aggregate protein p44, 17-kDa protein, Human insulin-like growth factor binding protein 5 (IGFBP5) mRNA, GS3686, Human monoamine oxidase B (MAOB) mRNA, Insulin-like growth factor II precursor, Human insulin-like growth factor binding protein 5 (IGFBP5) mRNA, Similar to ribosomal protein L21, X-linked mental retardation candidate gene, and *Homo sapiens* mRNA; cDNA DKFZp434A202. Genes not expressed in normal MPC but highly expressed in leukemia-associated MPC Lists of genes that are upregulated (instead of down-regulated) in leukemia-associated MPCs (AML/MDS, CML and MM) were created in comparison to normal MPC and a Venn diagram was made. The following is one such sublist of genes containing genes that are inactive in normal MPC but up-regulated in leukemia-associated MPCs revealing the identity of the subset of genes of interest: Beta-tropomyosin, *Homo sapiens* clone 24659 mRNA sequence, Human mRNA for DNA helicase Q1, OSF; contains SH3 domain and ankyrin repeat, ym22b12.r1 Soares infant brain 1NIB *Homo sapiens* cDNA clone, Human mRNA for pre-mRNA splicing factor SRp20, Human mRNA for golgi alpha-mannosidasell, OSF-2os, *Homo sapiens* gene for Proline synthetase, hk02952 cDNA clone for KIAA0683, wi24g10.x1 *Homo sapiens* cDNA clone, Lysosomal enzyme; deficient in Sanfilippo B syndrome, CTP synthetase (AA 1-591), WD repeat protein; similar to petunia AN11, Human mRNA for 5'-terminal region of UMK, complete cds, *Homo sapiens* chemokine exodus-1 mRNA, complete cds, Human GPI-H mRNA, complete cds, *Homo sapiens* mRNA encoding RAMP1, Transforming growth factor-beta-2 precursor, and *Homo sapiens* mRNA for KIAA0763 protein.

Those genes determined to be down-regulated 5-fold or more in leukemic-state (AML/CML/MM) cells include: Human mRNA for cartilage specific proteoglycan; *Homo sapiens* tyrosine phosphatase; X-linked mental retardation candidate gene; Human interleukin-10 receptor mRNA; H-interferon inducible peptide (6–16); Interferon-inducible 56 kD protein; Human insulin-like growth factor binding protein 5; and Winged helix transcription factor. Those genes determined to be up-regulated 5-fold or more in leukemic-state (AML/CML/MM) cells include: Interferon γ; Human mRNA for zinc finger protein (clone 431); Apolipoprotein D precursor; p53 tumor antigen; *Homo sapiens* Kueppel family zinc finger protein; Major group rhinovirus receptor precursor; ICE like protease; caspase-10/b; and Human transcription factor SIM2.

Visualizing Expression of Phenotypically & Functionally Relevant Genes Across Samples of Normal & Disease-Associated BM MPC.

Although GeneSpring is a highly flexible and user-friendly software application, it lacks the facility to create functionally relevant gene lists containing user-defined key words. This limitation was overcome by devising the following method via Microsoft Excel. A stepwise protocol to create such a gene list using Excel includes: Open the annotated microarray genome file (e.g., Affymetrix U95A) in Excel→select the column with gene names→select Data from pull-down menu→Filter→AutoFilter→Custom→enter key words (e.g., cell adhesion or cell cycle)→OK→generates a new Excel worksheet with the list of genes containing the key words. Copy and paste the list of genes containing the key words into GeneSpring and save the gene list with a meaningful name. Twenty-two (22) such functionally relevant gene lists (Table 2) were created.

The resulting approach is a simple and powerful way to peer into the expression profiles of focused sets of functionally relevant genes across samples of interest. For example, the human vascular cell adhesion molecule-1 (VCAM-1) gene is completely down-regulated in AML/MDS and the human insulin-like growth factor binding protein (hIGFBP1) gene is up-regulated in AML compared to all other samples. Similarly, *Homo sapiens* gene for LD78 alpha precursor is down-regulated in all of leukemia-associated MPCs. Finally, the lineage markers CD45 and CD68 are essentially absent from the leukemia-associated MPCs attesting to the high degree of purity achieved by the sample preparation technique of the present invention.

Results

The genomic changes observed in leukemia-associated MPCs are striking. As shown in Table 2, the changes (up-regulation and/or down-regulation) involved hundreds of genes. These changes were most dramatic in MPC associated with AML arising in a background of MDS and involved multiple classes of genes (Tables 1–2). Expectedly, the TNFa-induced changes were extensive. Given the high level of purity of MPC preparations, the enormous genomic changes observed are reflective of the underlying pathologic lesions in the MPCs themselves (and not due to the contaminating leukemic cells and/or macrophages). These studies strongly support the hypothesis that stromal cells in a leukemic patient are functionally defective and therefore purified MPCs are of value in restoring the loss of hematopoietic function in leukemic patients.

TABLE 2

Magnitude of global gene expression changes in leukemia-associated and TNFa-stimulated MPCs in comparison to normal MPC

| | AML/MDS MPC | CML MPC | MM MPC | TNFa MPC |
|---|---|---|---|---|
| # of genes up-regulated | 234 | 112 | 108 | 279 |
| # of genes down-regulated | 379 | 208 | 251 | 164 |

TABLE 3

Functional classes of genes analyzed across normal and leukemia-associated MPCs

| | | |
|---|---|---|
| Annexins (14) | Cell division cycle-related transcripts (36) | IGF system (24) |
| Caspases & apoptosis-related transcripts (33) | Cytokines (19) | Interleukins/receptors (76) |
| Cadherins (50) | Epidermal growth factors and related transcripts (22) | Integrins/disintegrins (70) |
| Calmodulins/calmodulin-dependent kinases (25) | Fibroblast growth factors (21) | Lineage-related markers (19) |
| Cell adhesion molecules (20) | Fibronectins (6) | Laminins (13) |
| Cathepsins (19) | Galectins (6) | Platelet-derived growth factors & receptors (12) |
| Collagens (71) | Growth factors (136) | TNF alpha-related transcripts (29) |
| | | TGF beta-related transcripts (25) |

The gene lists in Table 3 were created as described above and analyzed using GeneSpring. The numerical value in parenthesis refers to the number of transcripts in the corresponding class of genes analyzed.

Example 6

The present invention provides the following benefits: a) identification and documentation of BM stromal cell gene expression patterns under varied, normal, and leukemic hematopoietic conditions; b) identification of stromal cell genes that can be therapeutic targets for improvement of normal hematopoietic function that is constantly compromised in leukemic patients, and identification of similar targets for arresting the growth and progression of neoplastic clones since stromal cells provide the necessary support for preferential growth of leukemic cells (CLL, MM) within BM and protect the leukemic cells from chemotherapy-induced death (MM); and c) identification of new biological bases and new diagnostic markers for refinement of the classification and diagnosis of leukemia. This present invention can also lead to important insights into the pathogenesis of leukemia. In broad terms, analysis of global gene expression or transcriptome (transcriptional profile composed of all transcribed regions of the genome) is considered a nonbiased discovery-driven (as opposed to hypothesis-driven) approach to the analysis of gene expression. A stepwise genomic strategy encompasses preparation of total RNA from cells of interest, to generation of cDNA, to preparation of ds DNA, to in vitro transcription into cRNA, to fragmentation of cRNA, to hybridization of target RNA, to a microarray of known genes (and/or ESTs), to analysis of differentially expressed genes using an appropriate software to discern the patterns of gene expression or genomic signatures by a given disease-associated cell type.

Further test utility of sample preparation technology applied to normal EM-derived MPCs (untreated and treated with representative cytokines) and MPCs derived from patients with representative pre-leukemic and leukemic conditions for performance of high-resolution DNA microarray technology (Affymetrix genechip containing DNA from 12,000 known human genes, e.g., U95A oligonucleotide microarray).

Representative cytokines which are pathologically altered in hematopoietic conditions and that can be used in this study include TNF-α, TGF-β and interferon-γ. The pre-leukemic conditions include myelodysplastic syndromes (MDS) and the leukemic conditions include chronic myeloid leukemia (CML), acute myeloid leukemia (AML), acute lymphocytic leukemia (ALL), and multiple myeloma (MM).

The front-end strategy of microarray analysis involves the use of Percoll-gradient purified MPCs. As a follow-up strategy, to validate the stromal cell origin of the differentially expressed genes, MPCs obtained from cytospins of BM stromal cells by laser-capture microdissection (LCM) selected on the basis of morphology (FIG. 3) are used followed by "real-time" quantitative polymerase chain reaction (PCR). This can be performed with an LGM system as well as a "real-time" QPCR system. Validation can be performed on at least one sample from each of 6 normal BM M7NC/MPC types and on one sample from each of 5 leukemia-associated MPC types. Validation is considered successful if the microarray results and PCR results on a given MPC sample match using a suite of 20 genes selected based on median pattern of microarray results for the given cell type. This approach not only validates the microarray results but also ascertains the stromal cell origin of the expressed genes. The standard published protocols involving LGM and "real-time" quantitative PCR and the instructions accompanying the equipment are used for performing the experiments.

Stepwise LCMJ real-time QPCR protocol entails the following. Cytospins are made from BM stromal cells. The cytospins are stained with hematoxylin and MPC is selected for based on morphology. Microdissect up to 1,000 MPC from each sample. RNA is extracted and reverse transcribed into cDNA. The cDNA is amplified using gene-specific primers and "real-time" quantitative PCR.

By applying the combined power of different analytical techniques (such as hierarchical clustering and self-organizing maps) together with the recently developed sample preparation technology for stromal cells the present invention provides a molecular biological basis that can allow refinement of the classification and diagnosis of leukemias and lymphomas, uncovering the suspected disease heterogeneity. This enables the deciphering of the genomic expression profiles or signatures of bone marrow stromal cells in about 10 different physiologic states and about 20 different leukemic states. In addition to aiding in refinement of the classification and diagnosis of the hematopoietic malignancies, the data provides clues to potential novel drug targets and insights into pathogenesis.

The present invention functions by identifying the MPC genes that are differentially expressed after stimulation with different hematopoietic cytokines implicated in the pathogenesis of pre-leukemic conditions (MDS); in actual pre-leukemic disorders (MDS); and in overt leukemias (CML, AML, CLL, ALL, MM) as well as in lymphomas that have a leukemic phase with involvement of BM.

The present invention is accomplished by first determining the median gene expression profiles for MPCs associated with each disease and stimulated by each cytokine of interest (this objective can be achieved by treating the gene expression vectors of individual cases in each MPC category as replicates; this capability is available in GeneSpring software application). Then the gene groups that are up regulated and down regulated and that are common to all the members in a given MPC category are identified (this is accomplished using a series of Venn diagrams and creating required gene lists via GeneSpring). Finally, the up-regulated and down-regulated gene sets for a given disease-associated or cytokine-stimulated MPC are combined. This allows the identification of gene sets with minimal number of elements that are unique to a given MPC type with a capability to discriminate one MPC type from another (this can also be accomplished by means of a series of Venn diagrams and lists of required genes obtained via GeneSpring). Such gene sets can be of immense diagnostic value as they can be routinely used in an assay simpler than microarray analysis (for example "real-time" quantitative PCR). Such gene sets can additionally provide insights into pathogenesis and possible targets for design of new drugs.

Determine expression profiles of MPC genes which are regulated as a result of exposure of normal MPCs to cytokines that are known to have a hematopoietic support role and/or are abnormally elevated in pre-leukemic/leukemic conditions, i.e., TNF α; IL-4; TNF α+IL-4; interferon γ; TGF β; PDGF; FGF; EGF; and calmodulin.

TNF α, IL-4 and IFN γ are potent negative regulators of hematopoiesis. Notably these cytokines, especially TNF α, are elevated in marrow plasma of patients with myelodysplastic syndromes (MDS), the clinical hallmarks of which are anemia, leukopenia and thrombocytopenia (i.e., pancytopenia). TNF α and IL-4 are thus possible mediators of hematopoietic dysregulation typical of MDS. Studies regarding these regulators can uncover the molecular pathways leading to cytopenias in MDS patients. As indicated earlier, myeloproliferative disorders are another, in some ways similar, group of hematopoietic disorders that are clonal in origin but not overtly malignant clinically. These MPDs include polycythemia vera, essential thrombocythemia, idiopathic myelofibrosis (agnogenic myeloid metaplasia) and chronic myelogenous leukemia. These disorders have the potential to change from one to the other at any time, however the signals that trigger such conversion remain enigmatic. Idiopathic myelofibrosis (IMF), in which stromal cells seem to play a profound pathogenetic role, is characterized by fibrosis of the marrow cavity, extramedullary hematopoiesis, splenomegaly, and anemia and leukoerythroblastic features in the peripheral blood. While myeloproliferation is known to be a clonal process, the accompanying stromal cell proliferation and fibrosis are believed to be a polyclonal reactive process that is likely to be due to increased intramedullary activity of a number of cytokines including TGF β, PDGF, FGF, EGF and calmodulin, as shown by other investigators.

Cancer genomics is a rapidly expanding area of investigation. The focus is unique however in emphasizing not the leukemic cells themselves but rather BM stromal cells that provide a haven to various types of pre-leukemia and leukemia cells, non-Hodgkin's lymphomas (NHLs) and metastatic cancers (METs). Pre-leukemic clonal neoplastic conditions include myelodysplastic syndromes (MDSs) and myeloproliferative disorders (MPD5). Stromal cells are known to produce and/or respond to growth factors such as EGF, PDGF, FGF, VEGF, and cytokines such as IL-I or TNF a, partially explaining the interactive relationship between stromal cells and cancer cells, especially in MDS and CML.

In spite of similarities between BM stroma and non-BM stroma, certain sharp distinctions do stand out. Non-BM stromal cells are terminally differentiated fibroblasts, while BM stromal cells represent a unique pluripotent or pluridifferentiated mesenchymal cell type, thus exhibiting preserved developmental "plasticity". Using 5–10 cc BM aspirate samples from adult leukemic patients and 3–5 cc BM samples from pediatric patients with ALL, the study can analyze the BM stroma. One cc of marrow sample can produce at least 1 T-150 flask of stromal cells. One concern is that it can be hard to obtain marrow samples from cases like CML and myelofibrosis. In such cases stromal cells are grown using peripheral blood samples as described in the prior art. At least one flask of stromal cells (i.e., 1 cc marrow) to yield the RNA required for analysis. About 10 cases of each type of leukemia/lymphoma were studied. The study provided important insights into the functioning of the BM microenvironment in normal and leukemic hematopoiesis.

A database including all of the above information and that can include age, gender and associated major illness in terms of clinical/pathologic diagnosis for each subject/patient can be created. This can also include information on cytogenetic, molecular and flow cytometric studies. Finally, also included can be the information on clinical course in terms of disease progression and response to treatment exercising adequate care to protect the identity of individual patients. The study analyzed genomic expression profiles or signatures of bone marrow stromal cells derived from about 12 different normal bone marrow states and about 19 different leukemia/lymphoma states, approximately 10 cases of each as shown in Table 4, accounting for a total of 310 samples.

Using the information of the present invention, those of skill in the art can: a) study select gene or sets of genes as relevant to hematopoietic disease conditions using relatively inexpensive but low-throughput technologies such as Northern blotting, RNase protection assays and/or PCR intended for gene expression analysis; b) reanalyze the primary data by using newer and more powerful bioinformatic tools as they become available; and/or c) identify newer drug targets and diagnostic markers relevant to specific diseases, such as MM or CML etc.

TABLE 4

Scope of human BM samples targeted for DNA microarray analysis
(approximately 10 cases of each)

Normal BM mononuclear cells (NMNC)
Normal BM stromal cells, unfractionated and unstimulated (NBMS)
Normal purified mesenchymal progenitor cells, unstimulated (NMPC)
NMPC stimulated with 9 different cytokines:
NMPC stimulated with TNFα (TNFα MPC)
NMPC stimulated with TGFβ (TGFβ MPC)
NMPC stimulated with interferon y (IFNγ MPC)
NMPC stimulated with IL-4 (IL-4 MPC)
NMPC stimulated with TNFα + IL-4 (TNFα + IL-4 MPC)
NMPC stimulated with PDGF (PDGF MPC)
NMPC stimulated with EGF (EGF MPC)
NMPC stimulated with FGF (FGF MPC)
NMPC stimulated with calmodulin (calmodulin MPC)
MDS - Refractory anemia (MDS-RA MPC)
MDS - Refractory anemia with ringed sideroblasts (MDS-RARS MPC)
MDS - Refractory anemia with excess blasts (MDS-RAEB MPC)
MDS - Chronic myelomonocytic leukemia (M1)S-CMML MPC)
MPD - Polycytheniia vera (MPD-PV MPC)
MPD - Essential thrombocythemia (MPD-ET MPC)
MPD - Myelofibrosis (MPD-LMF MPC)
CML (CML MPC)

TABLE 4-continued

Scope of human BM samples targeted for DNA microarray analysis (approximately 10 cases of each)

AML-M0/M1/M2 (AML-MOJM1JM2 MPC)
AML-M3 (APL) (AML-M3 MPC)
AML-M4/M5 (myelomonocytic) (AML-M4i'M5 MPC)
ALL-L1/L2 (lymphoblastic) (ALL-L1IL2 MPC)
ALL-L3 (Burkitt's) (ALL-L3 MPC)
Multiple myeloma (MM MPC)
CLLISLL (CLL/SLL MPC)
Follicle center cell lymphoma (FCL MPC)
Mantle cell lymphoma (MCL MPC)
Lymphoplasmacytic lymphoma (LPL MPC)
Marginal zone lymphoma (MZL MPC).

Human Subjects

This study involves the use of bone marrow (BM) samples from human subjects. BM samples can be obtained from normal subjects (male and female 20–45 years) as well as leukemic patients after informed consent is obtained. Leukemic cells can be obtained from diagnostic samples of BM of adult and pediatric patients (in those cases in which cells remain unused after clinical diagnostic studies are preformed; i.e., about 90% of cases).

Example 7

In broad terms, global gene expression analysis is considered a nonbiased discovery-driven (as opposed to hypothesis-driven) approach to the analysis of protein expression. A stepwise proteomics strategy encompasses: solubilization of proteins from cells of interest; 2-D gel electrophoresis (IPG DALT); staining and image analysis of gels; excision of protein spots of interest; trypsin digestion of proteins; mass spectrometry (MALDI-TOF MS and/or ESI MS/MS) performed on tryptic fragments; identification of proteins by database searching. The present invention provides a method to analyze the population of expressed proteins (i.e., proteome) of BM MPCs in relation to hematopoiesis in collaboration with a state-of-the-art mass spectrometry facility.

The large-format 2-D gel electrophoretic system is used for reproducible separation of MPC proteins and to prepare 2-D PAGE protein maps for normal bone marrow-derived MPCs (untreated and treated with representative cytokines, e.g., TNF α and/or IL-4) and for MPCs derived from patients with representative pre-leukemic/premalignant and leukemic/malignant conditions. The pre-leukemic conditions include myelodysplastic syndromes (MDS) and the leukemic conditions include chronic myeloid leukemia (CML), acute myeloid leukemia (AML), chronic lymphocytic leukemia (CLL), acute lymphocytic leukemia (ALL), and multiple myeloma (MM). The protein samples can consist of culture supernatants/secreted proteins; extracellular matrix (ECM) proteins; plasma membrane proteins solubilized using a three-step differential extraction protocol, employing conditions of progressively increasing solubility; and whole cell lysate proteins similarly solubilized using the three-step differential extraction protocol. This subproteome approach not only simplifies the 2-D PAGE electrophoretic protein patterns but also reveals additional proteins, which would otherwise have gone undetected.

The system of the present invention can be used to differentially express MPC proteins (i.e., those that increased or decreased in intensity as compared to 2-D PAGE protein maps of normal, unstimulated MPCs) using mass spectrometry (MALDI-MS and/or nanoelectrospray ionization MS/MS) and/or Western blotting and/or Western-ligand blotting.

Using high-resolution proteomics with the added power of high-throughput robotics, enables the system to identify on a larger (semi-comprehensive) scale the MPC proteins that are differentially expressed in conditions that simulate pre-leukemic bone marrow (following stimulation with different cytokines); and in actual pre-leukemic disorders (MDS) as well as in overt leukemias (CML, AML, CLL, ALL, MM).

The system of the present invention enables the identification of MPC proteins whose expression is regulated as a result of exposure of normal MPCs to cytokines that are known to have a hematopoietic support role and/or are abnormally elevated in pre-leukemic/leukemic conditions, i.e., TNF α; IL-4; TNF α+IL-4; interferon γ; TGF β; PDGF; FGF; EGF; and calmodulin.

The system of the present invention also enables the identification of MPC proteins for which expression is altered as a result of exposure of normal MPCs to agents that are clinically used for mobilization of hematopoietic stem cells from BM into peripheral blood to facilitate easy collection and subsequent transplantation, e.g., G-CSF and G-CSF plus cyclophosphaniide.

Further, the system of the present invention enables the identification of Identify the MPC proteins whose expression is pathologically altered in hematopoietic disease states such as: MDS, CML, AML, CLL, ALL and MM by matching the 2-D PAGE protein maps of disease-associated MPCs with the 2-D PAGE database of normal MPCs. If a protein of interest does not exist in the normal MPC proteome, or if it exists in the normal MPC proteome but has not yet been characterized, then such proteins can be identified by MALDI-MS and/or Nano ESI MS/MS.

The system facilitates understanding of the pathogenetic mechanisms by identifying the phosphoproteins involved in cell signaling pathways. The systems immunoblots the whole cell lysate proteins of normal MPCs, untreated and treated with respective cytokines, using antibodies to phosphotyrosine, phosphoserine, and phosphothreonine. The system then locates the corresponding putative phosphoprotein spots on the gel and identifies the proteins by MALDI-MS and/or Nano ESI MS/MS. Similarly, the system can locate the altered phosphoproteins by immunoblotting the whole cell lysate proteins of untreated MPCs derived from leukemic patients. If a protein of interest does not exist in the normal MPC proteome, or if it exists in the normal MPC proteome but has not yet been identified, then MALDI-MS and/or Nano ESI MS/MS can identify the protein.

Bone Marrow MPCs Derived from a Leukemia Background Express Distinctively Different Patterns of Cell Adhesion Molecules from Normal MPCs.

BM stromal cells provide the background required for homing and subsequent proliferation and differentiation of hematopoietic stem cells. BM stromal cells also provide a rich microenvironment for metastases and growth of various leukemias. Based on the hypothesis that homing of normal hematopoietic cells and leukemic cells to marrow utilize the same adhesion mechanisms, it was questioned whether there are fine regulatory distinctions in terms of quantitative differences in the expression of the adhesion molecules in normal vs. leukemic BM microenvironments. In a pilot study 11 cell adhesion molecules (CAMs) and several lineage-associated markers for Northern blot analysis were targeted. Dexter-type cultures were grown under standard stromal cell culture conditions using bone marrow samples from a normal individual and from one patient diagnosed with and treated for acute myelogenous leukemia (AML). Representative cultures were treated with cytokines such as TNF α alone, IL-4 alone, and TNF α plus IL-4. MPCs from unstimulated and cytokine-treated cultures were purified using Percoll gradient techniques disclosed above. Total RNAs were extracted by a standard method and analyzed by Northern blotting. This study demonstrated expression by MPCs of several CAMs, heretofore unsuspected of expression by BM stroma. These include an embryonic endothelial cell protein Del1 (developmental endothelial locus 1), galectin-I, human milk fat globule protein (RMFG, lactadherin), and epithelial membrane protein I (EMP 1). Secondly, MPCs from the AML patient expressed significantly lower levels of mRNA for three CAMs Del-1, galectin-1, and collagen type 1 as well as for the adipocyte marker adipsin, and to a minor degree the muscle-associated protein caldesmon. On the other hand, mRNA for CAMs like TGF beta-inducible BiGH3, HMFG, osteoblast-specific cadherin 11, and VCAM1 were dramatically increased in AML-associated MPCs. CAMs such as integrin beta 5, fibronectin, EMP 1 and the muscle-associated molecule transgelin are variably increased in diseased MPCs and appear to be unaffected by treatment with cytokines tested. ICAM I was undetectable at basal level in either patient or normal samples, but was slightly elevated by TNF α and markedly elevated by TNF α plus IL-4. VCAM1 was mildly up regulated by TNF α alone or IL-4 alone, but markedly up regulated by TNF α/IL-4 in combination. Also, the MPCs from the patient were much more sensitive to stimulation by these inflammatory cytokines than were the normal MPCs. These studies establish that stromal cells in a leukemic patient are functionally defective.

Role of Leptin Receptor in Hematopoiesis Using Human Marrow Stromal Cells as a Model.

The receptor for the product of the obesity gene, leptin, is widely distributed in tissues ranging from central nervous system to reproductive system to hematopoietic system. Within hematopoietic system, OB-R is reportedly expressed on diverse cell types ranging from early CD 34+hematopoietic stem cells to circulating monocytes. Leptin acts on monocytes to induce production of TNF α and IL-6, which are powerful regulators of hematopoiesis. However, literature reports on the expression of leptin or its receptor on stromal cells are infrequent. To date, one particular report suggests that leptin acts on the stromal cells to enhance their differentiation into osteoblasts and to inhibit differentiation into adipocytes. Because leptin is an adipocyte-generated hormone and because marrow stromal cells represent a unique pluridifferentiated mesenchymal cell type expressing some adipocytic features, the expression of the leptin receptor by these cells was investigated in the hope of revealing its role in hematopoiesis.

By Northern blotting marrow stromal cells showed abundant expression of OB-R, consistent with their adipocytic nature. In terms of regulation, exposure of the stromal cultures to different cytokines revealed an interesting pattern of OB-R. As shown, G-CSF and TNF α down-regulated OB-R while IL-4 up-regulated OB-R expression by stromal cells. Simultaneous treatment of stromal cultures with TNF α and IL-4 nearly abolished OB-R expression. The expression of OB-R was also analyzed at the protein level by a high-resolution, high capacity 2-D, PAGE system, followed by Western blotting.

More specifically, the method provides the identification of leptin receptor in human BM stromal cell membrane protein extracts using 2-D Western blotting. The expression of OB-R was investigated at protein level using 2-D PAGE, followed by Western blotting. Two isoforms differing in molecular weight of 2.2 kDa (60.2; 62) and an isoelectric point of 0.2 pH unit (5.78; 5.98, respectively) have been identified (the pH was determined by using the values specified by the IPG strip manufacturer). The ability to subsequently stain the same Western blot with gold stain allowed precise localization of the immunoreactive protein spots of interest on the blot. The gold staining of the blot, by revealing other protein spots in addition to the immunoreactive spots, has provided the necessary landmarks in turn facilitating subsequent alignment with the silver-stained gel using an appropriate 2-D analysis software program (Melanie 3).

This technique has identified two OB-R isoforms that differ in molecular mass by 2.2 kDa (60.2; 62.4) and differ in their isoelectric point by 0.2 pH units (5.78; 5.98). The level of macrophage contamination is determined by two macrophage markers, CD68 and cathepsin B. The studies include the determination of OB-R expression in a) unfractionated stromal cells vs. isolated pluri-differentiated mesenchymal progenitor cells; b) unstimulated cultures vs. cultures stimulated with a variety of cytokine/hormones including leptin itself. The studies also include mass spectrometric characterization of the two OB-R isoforms detected by Western blotting in order to establish their exact structural differences.

Proteome Analysis of 2-D PAGE Separated Human BM Stromal Cell Membrane Proteins.

BM stromal cells support the growth and development of normal blood cells as well as providing a haven for malignant leukemia/lymphoma cells. Focusing on stromal cell-surface proteins as potentially playing a role in cell-to-cell communication in normal as well as in abnormal hematopoiesis, the mixtures of stromal-cell plasma membrane, and plasma membrane-associated proteins were analyzed by a high-resolution, high-capacity 2-D gel electrophoresis. The 2-D system described utilizes an immobilized pH gradient gel (pH 4–7) in the first dimension and a mini nondenaturing but high-resolution lithium dodecyl sulfate-polyacrylamide gel electrophoresis (LDS-PAGE) in the second dimension. As identified by silver staining, this system has resolved greater than 800 protein spots in a pH interval of 2.5 units (4.25–6.75, the isoelectric pH range for most of plasma membrane proteins to migrate) and a molecular mass range of 10–150 kDa. Equally important, the system is compatible with high sample loads (up to 1.5–2.0 mg of total protein in up to 350-µl sample volume). All the protein species identifiable by a silver stain that is compatible with subsequent mass spectrometric analysis have been analyzed by a 2-D gel software with respect to isoelectric point, molecular weight and mass abundance. The lectin-binding status of these proteins has also been determined by lectin blotting. Lectin blots and Western blots have subsequently been stained by a gold stain for detection of total proteins on the same PVDF membrane. Although gold-staining of the Western blot is not as sensitive as silver-staining of the gel, gold-staining of the Western blot generates the necessary landmarks for alignment with the silver stained gel, facilitating excision of spots of interest from the gel for identification by MALDI-MS. Representative protein spots were excised from gel and subjected to mass spectrometric profiling (MALDI-MS) and/or sequencing (Nano ESI MS/MS)

with subsequent database searching, resulting in a productive identification of ten proteins. The protein digests are then submitted in a near-ready state for mass spectrometry. Upon receiving the MS data the group performs the database searching. MALDI/MS has been used, which identifies a protein on the basis of its characteristic mass sizes, as well as MS/MS studies that provide amino acid sequences of selected masses to identify proteins with enhanced specificity and confidence level. This work represents the first systematic attempt to analyze BM stromal cell proteins by high-resolution 2-D gel electrophoresis and provides the basis for a full-scale proteome mapping of the marrow stromal cells. The present work can facilitate the long-term goal of deciphering the hematopoietic support functions of BM stromal cells.

Modulation of Stromal Cell Plasma Membrane Protein Expression by TNF α/IL-4.

The effects of TNF α/TM on bone marrow stromal cell plasma membrane protein expression has been tested using the described system. TNF α and IL-4 are regarded as negative regulators of hematopoiesis. Notably these cytokines, especially TNF α, are elevated in marrow plasma of patients with myelodysplastic syndromes (MDS), the clinical hallmarks of which are anemia, leukopenia and thrombocytopenia (i.e., pancytopenia). TNF α and IL-4 are thus possible mediators of hematopoietic dysregulation typical of MDS. TNF α/IL-4 treatment of the stromal cultures induced dramatic changes in the protein profile. Initial studies using plasma membrane protein samples show reduced expression of at least 7 proteins and enhanced expression of 13 proteins.

Analyzing the Insulin-Like Growth Factor System in Human Marrow Stromal Cells by 2-D PAGE Analysis of BM Stromal Cell Culture Supernatants.

Proliferation and development of normal and leukemic hematopoietic cells within bone marrow is regulated by interplay of various classes of molecules. These include cell adhesion molecules (CAMs), colony stimulating factors (CSFs), and cytokines as well as growth factors including insulin-like growth factors 1 and 2 (IGF 1 and IGF 2), which are small peptide homologs of proinsulin. IGF 1 has known erythropoietic activity, whereas the function of IGF 2 is less clear. IGF 1 and 2 exert their activities through two types of receptors. The type I IGF receptor, a tyrosine kinase receptor highly homologous to the insulin receptor, binds to IGF 1 and IGF 2 with high affinity. The type 11 IGF receptor, a mannose 6-phosphate receptor that lacks intrinsic kinase activity, binds IGF 2 with high affinity and IGF I with low affinity. The type and number of receptors expressed on a target cell determine the strength of the IGF signal. One important key to understanding the IGFs' role in hematopoiesis is to appreciate how biological effects of receptors are modulated by larger soluble proteins, the IGF binding proteins (IGFBPs), which share no homology with the IGF receptors. Because IGFs and IGFBPs play important roles in cell growth and proliferation in many tissues, and because marrow stromal cells support hematopoietic growth and development, the patterns of expression of the IGF system components by marrow stromal cells cultured under serum-free conditions is necessary. To this end, unfractionated and purified stromal cells were analyzed, side-by-side, by Northern blotting, under varied stimulatory conditions for expression of IGFs and IGFBPs with surprising results. IGF 2 is constitutively expressed at a high level by macrophages in Dexter cultures; it is down regulated markedly by TNF α alone; moderately by TNF α plus IL-4; and unaffected by IL-4 alone. On the other hand, IGF 2 is minimally expressed by unstimulated MPCs, but is markedly up regulated by TNF α alone or IL-4 alone; and moderately up regulated by combined TNF α and IL-4. IGFBP4 is abundantly expressed both by macrophages and MPCs and is unaffected by cytokine treatment. In contrast, IGFBPs 5, 7, and 10, selectively expressed by MPCs, show no evidence of expression by macrophages and are unaffected by cytokine treatments. IGF 1 and the precursor to IOFBP 3 are not expressed in either macrophages or MPCs, either constitutively or after stimulation with TNF α, IL-4 or both. In initial studies, bone marrow mononuclear cells expressed none of the IGFs or IGFBPs tested. These results provide important insights into the operation of the IGF system in stromal cells and it is likely that potentially novel IGFBPs can be uncovered by ligand blotting studies.

The present invention provides a large-format 2-D gel electrophoretic system for reproducible separation of MPG proteins and to prepare 2-D PAGE protein maps for normal bone marrow-derived MPCs (untreated and treated with representative cytokines, e.g. TNF α or IL-4) and for MPCs derived from patients with representative pre-leukemic and leukemic conditions. The pre-leukemic conditions include myelodysplastic syndromes (MDS) and the leukemic conditions include chronic myeloid leukemia (CML), acute myeloid leukemia (AML), chronic lymphocytic leukemia (CLL), acute lymphocytic leukemia (ALL), and multiple myeloma (MM). The protein samples can consist of culture supernatants/secreted proteins; extracellular matrix (ECM) proteins; plasma membrane proteins solubilized using a three-step differential extraction protocol employing conditions of progressively increasing solubility; and whole cell lysate proteins similarly solubilized using the three-step differential extraction protocol. This subproteome approach not only simplifies the 2-D PAGE electrophoretic protein patterns but also reveals additional proteins, which would otherwise have gone undetected.

Molecular Analysis Assay Involving the High-Resolution 2-D PAGE and Mass Spectrometric Identification of Gel-Separated Proteins.

The completion of human genome project has provided a huge proteome database including the theoretical mass databases generated on the basis of site-specific cleavage employing proteolytic enzymes, such as trypsin and others. The availability of highly sensitive biological mass spectrometers together with the capability of bioinformatics to search extremely large amounts of data and identify the relevant proteins matching the mass spectrometry data provides the basis for the current excitement in proteomics. The focus of the interest is the BM MPC proteome as expressed under varied functional and disease states. The goal of the present invention is to identify BM MPC proteins that have possible functional and/or pathologic significance, that is, those proteins that show altered levels of expression in response to cytokine treatments and various leukemic states.

Until recently, the focus of the laboratory has centered on isolation and characterization of BM stromal cell adhesion molecules using a novel 2-D cell blotting technique. For this purpose, applicants have established an analytical 2-D mini gel system that separates stromal cell plasma membrane proteins using 18-cm long 4–7 pH range IPG strips in the $1^{St}$ D (Amersham Pharmacia Biotech). Subsequent to IEF, the IPG strip is cut into appropriately small pieces and subjected to 2 D separation using nondenaturing lithium dodecyl sulfate-polyacrylamide gel electrophoresis (LDSPAGE) and mini gels. The reason for using mini gels in the $2^{nd}$ D is that they are compatible with a downstream functional assay involving cell adhesion. The stromal cell membrane proteins are blotted on to a PVDF membrane and assayed for hematopoietic cell-binding proteins directly on the blotting membrane. The system can be extended using 17-cm long 3–10 pH range IPG strips (Bio-Rad) for separation of stromal cell culture supernatants, ECM proteins, and whole cell lysates. As detected by silver staining of the gels, and analyzed by appropriate software (GelLab II or Melanie 3) this 2-D system has resolved greater than 800 membrane protein spots within a pH interval of 2.5 units (4.25–6.75) and a MW range of 10–150 kDa. Similarly, the ECM samples showed 475 spots; and conditioned media from BM stromal cell cultures grown under serum free conditions showed 524 spots. Not surprisingly, the total cell lysate of BM stromal cultures showed only 553 spots, most likely representing the abundant housekeeping proteins and masking detection of many functionally relevant proteins. These observations provide the rationale for the proposed subproteome approach involving the use of differential solubilization of sample proteins and multiple large gels. Membrane proteins thus far identified by mass spectrometry followed by database searching; proteins are identified by standard Western blotting. Select IGF binding proteins were identified by ligand Western blotting. The blotting shows the identification of IGF-binding proteins (IGFBPs) using 2-D ligand blotting. The conditioned media from BM stromal cultures grown under serum-free conditions were concentrated using Microcon concentrator, and proteins were fractionated using a high-resolution 2-D PAGE. The separated proteins were electroblotted onto PVDF membrane and subjected to Western ligand-blotting assays using 1–125 labeled IGF-2, resulting in the identification of a series of IGFBPs (up to 30 spots). Notably, TNF α treatment of the cultures down-regulated two LGFBPs and up-regulated IGFBP labeled 6.

By necessity the protein work began on BM stromal cells using a nondenaturing (LDS-PAGE) mini gel system that contained no reducing/alkylating agents. To preserve the function of 2-D gel separated proteins many otherwise powerful sample preparation methodologies designed for proteomic studies (such as multiple surfactant solution, MSS) were avoided. While mini gels are convenient and allow comparison and information transfer to large-format gels, they are less sensitive.

Subproteomes According to Sample Prefractionation.

In order to be able to identify the low-abundance proteins implicated in the regulatory and pathologic processes, a number of approaches to prefractionation of the whole cell lysates have been described. Applicant studied the subproteomes of secreted proteins from BM stromal cell culture supernatants as well as ECM proteins. Notably, the ECM protein samples can be a rich source of functionally relevant cytokines and chemokines since the latter are known to mediate function by binding to ECM. In addition, the plasma membrane and whole cell samples were subjected to the 3-step sequential solubilization protocol shown. The solubilizing solutions can be prepared in-house or purchased commercially (Bio-Rad). The first step involves the use of Tris base, which can solubilize the peripheral membrane proteins and cytosolic proteins. These proteins are lyophilized and subsequently solubilized prior to 2-D PAGE in a standard solubilizing medium (the modified O'Farrell cell lysis solution containing urea, CHAPS, DII, Iris, ampholytes and appropriate protease inhibitors). The resulting pellet can also be solubilized in the standard 2-D solubilizing medium and subjected to 2-D PAGE. Because the standard solution cannot solubulize some proteins, the membrane-rich pellet is finally solubilized in a potent multiple surfactant solution (MSS) consisting of urea, thitheea, Cl-LAPS, zwittergent 3–10 and tributyl phosphine (TBP) in addition to Iris base and ampholytes that is compatible with subsequent IEF. The MSS has been shown to solubilize the hydrophobic proteins with as many as 12 transmembrane regions (TMRs), facilitating their 2-D analysis. Another final step incorporating 1% SDS in boiling sample buffer can be used to test by 1-D SDS-PAGE if any proteins remained unsolubilized after these extractions (notably, SDS extract is unsuitable for 2-D PAGE analysis since SDS interferes with IEF). The prefractionation step clearly reduces the complexity of the sample. Thus, the serial extractions not only simplify the gel images and reduce spot overlapping frequently encountered in single-step extractions but also correlate closely with the cellular location of specific proteins, providing clues to their function. The prefractionation strategy can be extended to enriching low-abundance proteins in culture supernatants by selective removal of contaminating albumin using an Albumin Depletion Kit (containing Cibachron Blue resins) (Genomic Solutions, mc). Similarly membrane glycoproteins can be enriched by a Glycoprotein Enrichment Kit (containing lectins) prior to 2-D PAGE analysis (Genomic Solutions, Inc.).

Subproteomes According to Overlapping pH Gradients.

Using a series of medium-range and partially overlapping pH gradients (3–6, 5–8, 7–10, each 17-cm long) (Bio-Rad) can enhance reproducibility and resolution by creating "virtual" gels with up to 40 cm equivalent of PI separation across a pH 3–10 range. Alternatively, a combination of two pH gradients, pH 4–7 and pH 6–11, each 24 cm-long (Amersham Pharmacia Biotech) can be used, also providing a "virtual" separation distance of 40 cm across a pH range of 4–11. These strips accept micropreparative sample loads (1–2 mg). Notably, a given sample of cells yields a total of 8 protein samples. These samples include one protein sample composed of conditioned medium, one protein sample comprising of ECM proteins, three protein samples derived from plasma membrane lysates and three protein samples derived from total cell lysates, following application of a three-step protein extraction protocol to purified plasma membranes and total cells. Eight protein samples can thus translate into 24 large format (18 cm) gels corresponding to three overlapping $_1$st D gels; or 16 extra large format gels (24 cm) corresponding to two overlapping $_1$st D gels. Proteomics is no longer considered a single 2-D gel study. Taking advantage of the common spots in the 2nd D corresponding to overlapping regions, PDQUEST software can allow "stitching together" of the constituent gels, creating the so-called "cyber gel" providing a composite map for each protein sample. The data generated can be stored in an internet-accessible 2-D PAGE database in the form of 8 submaps. Three of these submaps correspond to plasma membrane proteins representing 3-step solubilization; one of them corresponds to secreted proteins; one of them corresponds to ECM proteins; and 3 of them correspond to total cell lysate proteins representing 3-step solubilization. These submaps can be linked to a master synthetic gel, a conglomerate of the submaps, representing the so-called "cyberproteome" of MPCs. Given the ability to run up to 12 IPG strips per 1st D gel (using IPGPhor) and 10 to 12 large or extra large SDS-PAGE gels per $_2$nd D gel run (using Hoefer DALI and Ettan DALI II, respectively), the resulting number of gels can be well within the manageable workload of one person (36). Although not easily accessible now, some innovative technological developments are on the horizon, e.g., development of fluorescence 2-D difference gel electrophoresis (DIGE), which could minimize the tedium. Unlike the current practice of running different protein samples on separate gels, and then staining and comparing the gels, DIGE technology uses matched, spectrally resolvable dyes (e.g., Cy2, Cy3 and Cy5) to label protein samples prior to 2-D separation. Differentially labeled protein samples are mixed and co-separated by 2-D electrophoresis, allowing analysis of at least three samples on a single gel. Gels are scanned and proteins are subjected to image analysis using appropriate software. Alternatively, one can use a highly sensitive silver stain to visualize the proteins after electrophoretic separation. Notably, the silver stain is compatible with subsequent mass spectrometry analysis.

Follow-Up Strategy for 2-D PAGE Using the So-Called Ultrazoom LPG Gels with Narrow-Range pH Gradients.

Commercially available narrow-range IPG strips include pH 3.54.5; 4.0–5.0; 4.5–5.5;5.0–6.0; 5.5–6.7. These are available as 18 cm and 24 cm-long strips, consequently allowing spanning of 1 pH unit over a distance of 18–24 cm and providing extraordinary resolution. By using narrow pH gradients (lpH unit) up to 10 mg of protein would be loaded onto a single IPG gel strip, either by repeated sample cup application or by in-gel rehydration without incurring vertical or horizontal streaking. Employing a combination of such narrow-range overlapping IPG strips, one study utilized up to 40 2-D gels for analysis of a single protein sample. The preference is not to follow such extreme approach but rather to use these gradients as a backup in situations where a functionally relevant protein is first detected by the front-end strategy but could not be studied by mass spectrometry for lack of adequate resolution or due to overlapping spots. The 24-cm long narrow IPG strips can be subjected to $_2$nd D using correspondingly extra large slab gels (the required precast, plastic-backed gels can be purchased from Amersham Pharmacia Biotech). However, the "giant 2-DE" 30×40 cm size gels are impractical to handle. The situations for the use of narrow range pH gradients include situations like detection of proteins by Western blotting using anti-phosphotyrosine antibodies or Western ligand blotting using labeled IGF 1 or 2, which are probably more sensitive than silver staining. Consequently, these assays identify the functionally relevant proteins but without providing the actual identity of the individual proteins. Because the front-end strategy can at least provide the range of the phosphoprotein or the IGF-binding protein identified, on the basis of this information samples can be subjected 2-D PAGE using the appropriate ultrazoom IPG strip, which as indicated above can permit loading of several mg of protein sample. Extra large precast slab gels (26×20 cm) with plastic backing suitable for running the 24-cm long ultrazoom IPG strips and the appropriate electrophoretic system (Ettan DALI II 2 dimension electrophoresis system) that runs up to 12 of these gels are commercially available (Amersham Pharmacia Biotech).

Summary of Subproteome Strategy.

The subproteome approach involves: 1) Cellular fractionation involving isolation of purified MPCs. 2) Subcellular fractionation involving preparation of functionally relevant protein sets. These include: 2a) secreted proteins such as colony stimulating factors (CSFs), cytokines, etc in the conditioned media; 2b) ECM proteins such as cell adhesion molecules (CAMs), etc; 2c) plasma membrane proteins such as various receptor molecules, CAMs and components of cell signaling systems, etc; 2d) finally, whole cell lysate proteins that include some of these proteins plus cytosolic and nuclear proteins. The cytosolic and nuclear proteins can be a rich source of target proteins for phosphorylation with a regulatory function.

2-D PAGE Data Capture and Analysis

2-D PAGE data capture and analysis can be performed using standard equipment and protocols. Silver-stained gels can be scanned using an imaging densitometer and processed with QuantOne software (Bio-Rad) whereas gels stained with fluorescent Sypro Ruby (with 450 nm in the excitation range) can be scanned using a STORM 860 gel and blot imaging system and processed with ImageQuant Solutions software (Amersham Pharmacia Biotech). A number of factors, including differences in sample preparation and loading, staining and image acquisition can influence the reproducibility of 2-D gel protein separation. Quantitative data are reported as spot volumes (integrated spot densities). In experiments comparing replicate 2-DE patterns of the same sample or 2-DE patterns of samples from different individuals, the spot volumes in each pattern are scaled to correct for differences in the total amount of protein loaded onto each gel. These variations are compensated by accurately comparing the quantity of any spot across multiple gels. These operations can be performed using a dedicated 2-D gel analysis software, Melanie 3. This program can analyze such variations by scatter analysis and can compensate for varying staining absorption across proteins by normalizing protein expression change. Varying stain intensities and sample sizes can be compensated for by relative spots quantification. The Melanie 3 software also has the capability to merge several gel electrophoretic patterns from the same sample into a composite gel, providing fine control over the included proteins. Finally, the software can compensate for gel distortions caused by variations in protein migration through alignment of the gels.

Mass Spectrometric Instrumentation.

Examples of such mass spectrometers include, but are not limited to, Voyager DE Pro (Applied Biosystems, formerly Perceptive Biosystems, Inc.) and QSTAR (Applied Biosystems). Voyager DE Pro is a matrix-assisted laser desorption time-of-flight mass spectrometer (MALDI-IOF) that can be operated in a linear mode for the analysis of large biomolecules or in a reflector mode for high-resolution analysis of smaller molecules, i.e., peptides. The MALDI-TOF instrument also utilizes delayed extraction technology that results in greatly increased resolution, sensitivity and mass accuracy. This is the instrument of choice for high throughput analysis, with a capacity of up to 100 samples per sample plate. On the other hand, the QSTAR is a hybrid quadrupole-quadrupole-time-of-flight mass• spectrometer. Samples are introduced in solution and are ionized by electrospray. For samples requiring the highest sensitivity, Dr. Jackson utilizes a low flow rate (25 nl miff') electrospray called nanoelectrospray, typically requiring only 1–2 µl of a solution for sample analysis. The QSTAR instrument yields data quite similar to those obtained from the MALDI-TOF instrument, except that the QSTAR data analysis is somewhat more complex due to the multiple charging of peptides by the electrospray process compared to the single charging applied to peptides on the MALDI-TOF instrument. One important additional characteristic of the QSTAR is its ability to determine structural information from sample molecules by tandem MS/MS. This is achieved by effectively "purifying" selected molecules within the mass spectrometer's first quadrupole section. For analysis of peptides produced by tryptic digestion, a single MS experiment is initially performed to determine the masses of components present in the mixture. Next, MS/MS experiments are carried out to select specific peptides for de novo amino acid sequence determination. Typically 2 µl of peptide mixture is sufficient for determining the sequences of ten to twelve peptides.

Mass Spectrometric Analysis by MALDI

The scheme for mass spectrometral analysis of in-gel tryptic digests of proteins for the purpose of protein identification consists of several steps. First, the peptides extracted from the gel must be cleaned and concentrated. The cleanup is necessary to remove residual detergent and other non-peptide materials that can interfere with the analysis of the tryptic peptides. This step involves binding of the peptides to a Microcon-SCX adsorptive microconcentrator. This is a cation exchange membrane held within a microcentrifuge device. At low pH, the peptides bind to the negatively charged membrane, while uncharged or negatively charged molecules pass through. After a brief wash, the peptides are eluted from the membrane in two 25-µl steps of 1.5 N ammonium hydroxide in 1:1 methanol/water. The samples are then speed-vac dried for 10 minutes, and fresh solvent is added for additional treatment to concentrate the sample prior to MS analysis. Initially, all samples can be analyzed by MALDI-TOF MS. For this analysis, the sample from the Microcon-SCX elution can be dissolved in 0.1% trifluoroacetic acid (TFA) in water and loaded on a ZipTipC 18 Pipette tip. The tip is then washed with the same solution and the peptides are then eluted directly onto the MALDI-TOF sample plate with 2 µl matrix solution (cyano-4-hydroxy-cinnamic acid, 10 mg/mi in 0.1% TFA in 1:1 acetonitrile/water). The spotted sample is dried at room temperature for at least five minutes before the sample plate is loaded in the instrument. The instrument calibration is performed externally by the addition of a calibration mixture to the sample plate. Samples are calibrated internally if the known tryptic autodigestion peptides are observed in the sample. This can be used as long as the specific type of trypsin used in the proteolytic digestion step is known. After data collection, the data can be further processed in two ways. First, the data can be treated by noise reduction software and second, it can be deisotoped. Software for both operations of these programs are standard features of the Data Explorer system provided with the Voyager DE Pro mass spectrometer. The obtained peptide mass data can be subjected to peptide fingerprint analysis utilizing one of the protein database search sites on the Internet, such as Mascot or MS-Fit. While each of these search sites has access to several databases, one can initially select either OWL or NCBlnr. One can search the database with a standard set of criteria without using a species filter. The practice is to select three variable modifications to allow for conversion of peptide N-terminal glutamine to pyro-glutamate, and oxidation of methionine residues; allowing for up to one missed cleavage. Neither the protein MW nor the PI can be used as a search parameter (these, however, can be used for subsequent validation of the matched protein). Also important is that expected peptide masses of known potential "contaminants" such as keratin and trypsin can be excluded from analysis. Finally, the peptide mass tolerance can be set to +1–0.15 Da relative to the monoisotopic MW of the singly charged peptide ion. Positive database hits are scored with a MOWSE number. The higher the number of hits the greater the confidence level. The database search algorithm relates the significance level for a given search. If a high MOWSE score is obtained indicating an unambiguous match, one can consider the protein positively identified, otherwise the sample can be subjected to analysis by use of the QSTAR mass spectrometer.

Mass Spectrometric Analysis by Nano ESI MS/MS.

Samples that require analysis utilizing the QSTAR, following cleanup by Microcon-SCX adsorptive microconcentrator, can be concentrated by binding the peptide mix to a small amount of POROS R12 reversed-phase C18 chromatographic support packed into a nanopurification capillary. The packed capillary column volume is ~10–15 nl. The sample, dissolved in 10-p.l of 5% acetic acid in water, is applied to the capillary by use of a ten-µl gel loading pipette tip. A brief centrifugation forces the liquid down the capillary so that the peptides can bind to the support. The support is then washed with 10–15 p.1 of 0.5% acetic acid in 1:50 methanol/water. The peptides are eluted from the purification capillary into a nanospray capillary by the addition of 2 µl of 0.5% act id in 1:1 methanol/water followed by brief centrifugation with the nanospray capillary stacked just below the purification capillary in a micropurification holder (MDS Protana). Initially, data for a single MS run is collected. The peak masses are labeled and peptides are selected for potential MS/MS sequencing by locating those that appear to be doubly charged. Most peptides resulting from a tryptic digest can have a significant doubly charged form, which is ideal for MS/MS sequencing. The first quadrupole of the QSTAR is tuned to pass a 2 Dalton window for the pre-selected doubly charged peptide ions, one at a time, for fragmentation by collision with low-pressure argon gas in the second quadrupole. Collision energy is adjusted for each peptide to obtain the best possible MS/MS spectra. Data are collected long enough to get good quality spectra. After MS/MS spectra are collected for all selected peptides, the data are manually interpreted. Internet protein database searches are performed similar to that for MALDI-TOF peptide fingerprint, except that the search is a partial amino acid sequence search with mass information (i.e., Mascot, employing Sequence Query format). The search criteria cannot screen for a species or a protein MW or PI (which, however, can be used for subsequent validation of the protein matched). Also important is that expected peptide masses of known potential "contaminants" such as keratin and trypsin can be excluded from MS/MS analysis. One missed cleavage can be allowed and two variable modifications can be selected, carbamidomethylation of cysteine and oxidation of methionine. The tolerance of the peptide monoisotopic mass can be set to +1–0.3 and the MS/MS tolerance can be set at +1–0.2. This type of search generally requires only two or three peptide sequences consisting of three of the amino acids per peptide to obtain a statistically significant match (a high MOWSE score). Once a match is identified, a list of the matched peptide's theoretical MS/MS fragments can be generated to compare with the observed fragments to further confirm the correctness of the match.

Establishment of Large-Format 2-D PAGE Protein Maps for MPCs Derived from Normal BM.

The normal cell samples include, A)-Untreated normal MPCs; B) Normal MPCs treated with TNF α; C) Normal MPCs treated with TNF-α and IL-4. Each cell sample can generate a total of 8 protein samples, 1) culture supernatants/secreted proteins (1 protein sample); 2) extracellular matrix (ECM) proteins (1 protein sample); 3) plasma membrane proteins solubilized using a three-step differential extraction protocol employing conditions of progressively increasing solubility (3 protein samples); 4) whole cell lysate proteins similarly solubilized using a 3-step differential extraction protocol (3 protein samples). Each protein sample can generate 3 large format 2 D gels (corresponding to 3 medium-range, overlapping IPG gradient gels, pH 3–6; 5–8; 7–10). This means each cell sample can generate 24 large format 2 D gels, leading to generation of at least 72 large format gels for analysis of normal MPCs. To account for duplicate or triplicate samples, the gel number falls in the range of 200–300.

Establishment of Large-Format 2-D PAGE Protein Maps for MPCs Derived from BM Involved with Representative Pre-Leukemic and Leukemic Conditions.

The disease-associated MPCs include those from MDS, CML, AML, CLL, ALL, and MM. As above, each MPC sample can generate 24 large-format 2 D gels. With 6 such diseases being studied, the gel number can reach 144. To account for duplicate or triplicate samples, the gel number falls within the range of 400–500. The use of IPGPhor, together with ready-made IPG strips, permits sample in-gel re-hydration and performance of unattended IEF overnight by adding automation to the 2-D procedure.

Using High-Resolution Proteomics and with the Added Power of High-Throughput Robotics, Identify on a Larger (Semi-Comprehensive) Scale the MPC Proteins that are Differentially Expressed in Conditions that Simulate Pre-Leukemic Bone Marrow (Following Stimulation with Different Cytokines); and in Actual Pre-Leukemic Disorders (MDS) as Well as in Overt Leukemias (CML, AML, CLL, ALL, MM).

A robotically guided system facilitates excision of protein spots (by a spot cutter or picker) from 2-D PAGE gels, transfer of protein samples to 96-well microplates, and automated protein digestion in the microwells. Such a system reduces the time and labor relative to manual procedures and provides high throughput while minimizing keratin contamination from human skin, a frequent problem in proteomics research. The preferred method is to excise all spots from a gel but to process only the spots of interest, storing the remaining excised proteins frozen at −70° C. for a later use. The robotic components can include MALDI slide spotter in addition to an automated protein spot picker and digestion station.

Example 8

Methods

Figure 15:
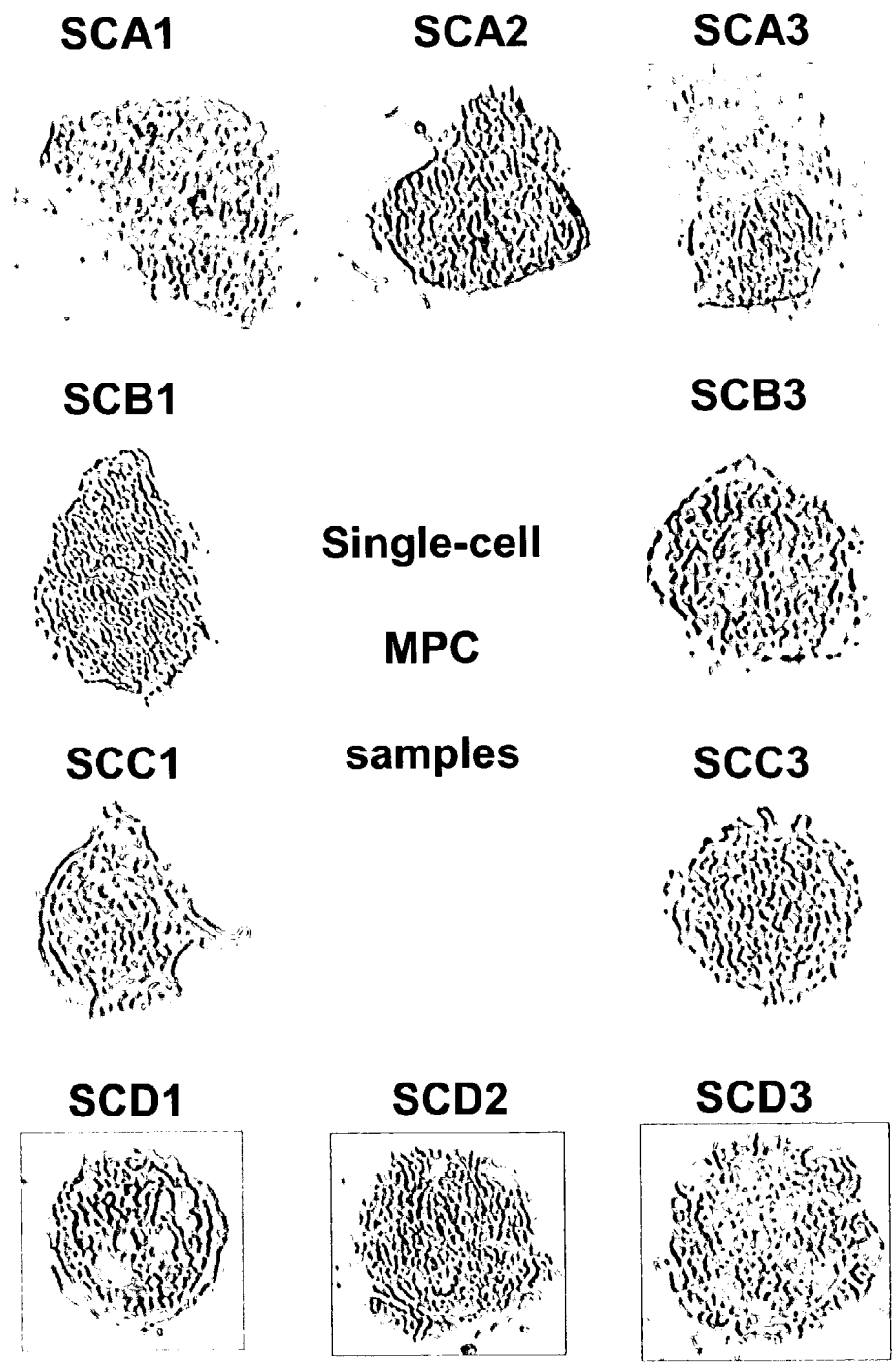
FIG. 15 shows photomicrographs of single-cell MPCs that were isolated by laser capture microdissection (LCM) and subsequently targeted for microarray analysis.

The present study involved microarray analysis of 23 samples and a corresponding number of chips. The samples were obtained from 4 normal healthy adult human subjects, consisting of mixtures of unfractionated stromal cells (collective USCs or cUSCs, 8 samples), Percoll gradient-purified MPCs (collective MPCs or cMPCs, 5 samples) and single-cell MPCs (sMPCs, 10 samples) obtained by laser-capture microdissection (LCM). The study design allowed for adequate controls and replicates appropriate for a comprehensive gene expression profiling of normal BM stromal cells. The isolated single stromal cells were selected on the basis of morphology. Wright-Giemsa stained cytospin preparation revealed characteristically large cells with a relatively irregular nucleus and cytoplasm compartmentalized into ectoplasm and endoplasm. Subsequently, applicant identified a hematoxylin stain as a substitute for Wright-Giemsa stain. The hematoxylin stain is simpler to use and provides morphologic detail sufficient to allow recognition and isolation of these cells by laser capture microdissection and does not interfere with the downstream microarray testing (see details under Materials & Methods). The photomicrographs of 10 stromal cells that have been subjected to microarray testing are shown in FIG. 15. To serve as controls and facilitate comparison, applicant analyzed side-by-side 8 samples of unfractionated stromal cells that are "contaminated" by up to 35% macrophages and 5% hematopoietic cells (referred to collective USC, or cUSC), and 5 samples of Percoll-gradient purified stromal cells, up to 95% pure (referred to collective MPC, or cMPC to distinguish from SMPC). RNA isolated from sMPC samples was subjected to 2 rounds of amplification using RiboAmp kit (Arcturus, Inc) prior to in vitro transcription (IVT). In contrast, RNA samples isolated from cUSCs and cMPCs were used without amplification for IVT. The subsequent steps of microarray testing were standard for all 3 types of samples and are schematized as follows: Preparation of total RNA→generation of cDNA→preparation of ds cDNA→in vitro transcription into cRNA→fragmentation of cRNA→hybridization of target RNA to a microarray of known genes (Affymetrix U95Av2 oligonucleotide microarray, with 12,625 probe sets)→Signal quantification and first-tier analysis using the microarray quantification software, Microarray Suite (MAS v. 5, Affymetrix, Inc). The presence of a gene within a given a sample was determined at a detection p-value of <0.05, according to the statistical expression analysis algorithm employed by MAS v.5, and was graded absent (A), marginal (M) or present/positive (P).

Assessment of RNA Amplification Method

Since single-cell microarrays are relatively novel, applicant critically reviewed the data with respect to two important statistics that would reflect on the reliability of RNA amplification assay procedure employed before analysis involving data-mining techniques. a) 3': 5' ratios of housekeeping control genes: As shown in Table 9, these ratios were close to 1 in the standard unamplified samples, whereas, they were increased in the amplified samples. Although this is to be expected due to preferential amplification toward 3' end, since amplification may not proceed all the way up to 5' end, applicant wanted to exclude possible sample degradation. For reasons unclear, in the case of ACTB (beta actin), the 3':5' ratios were highly variable across single cell MPG samples. In any event, the 3':5' ratios in case of GAPD (glyceraldehyde 3-phosphate dehydrogenase) were relatively tight, suggesting no evidence of sample degradation. Furthermore, both GAPD and ACTB gene probes that were employed as part of the standard gene probe set yielded relatively stable signals across replicates in each sample type, which is further evidence of intactness of RNA samples targeted for microarray analysis. b) Number of genes present or detected: As outlined in Table 9, the amplified single cell MPG RNA samples expectedly showed significantly lower number of genes compared to the standard RNA samples (on average 34% vs. 46% of the genes etched on the array). The fact that the number is relatively constant across single cell replicate samples is further indication of the reliability of the data. Notwithstanding the shortcomings of the amplification procedure, it is important to bear in mind that the conclusions are based only on those stromal cell genes that are detected commonly across unamplifed cMPCs and cUSCs as well as in amplified sMPCs (but do not include the genes undetected or the genes selectively detected in sMPCs).

Data Mining and Reproducibility of Overall Procedures

Figure 16:
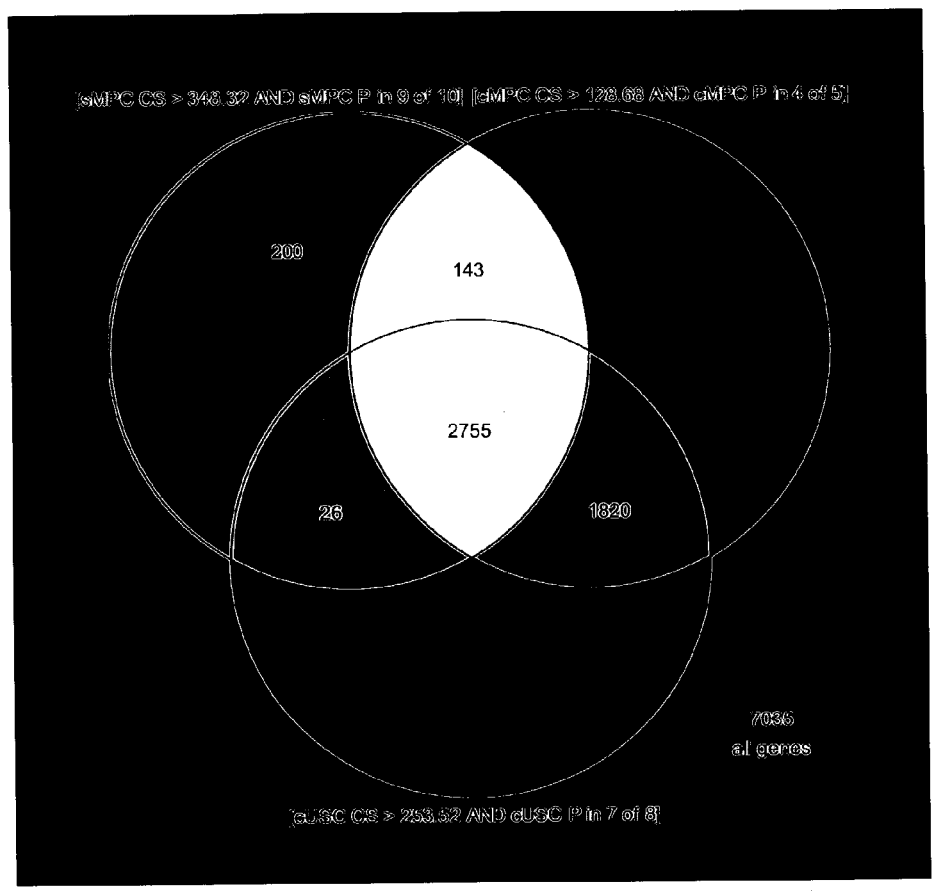
FIG. 16 shows a Venn diagram displaying the stromal-cell gene-list. Stromal cell genes are operationally defined as being active in at least 9 out of 10 single cell MPCs AND 4 out of 5 collective MPC samples AND 7 out of 8 collective USC samples, i.e., 20 of 23 samples tested. This criterion was very stringent and automatically excluded the outliers, independently of filtering for genes with weak expressions on the basis of control strength (referred to as C or CS). The stromal cell gene list of 2755 includes 13 AFFX microarray-assay positive controls.
Figure 17:
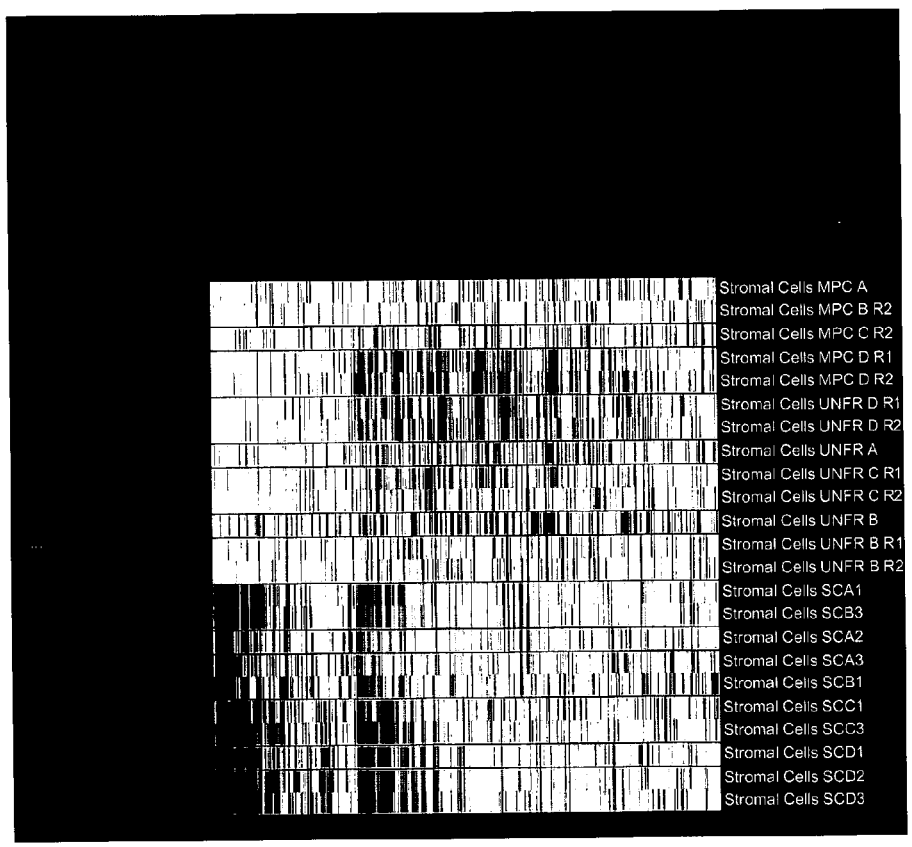
FIG. 17 shows a two-dimensional hierarchical clustering of 2755 stromal cell genes based on the expression profiles of 23 samples. The gene tree is displayed on top and the experiment or sample tree is shown on left. Accordingly, each column represents a particular gene on the chip and each row represents a separate stromal cell sample.

The thrust of the present invention is to identify genes that are relatively uniformly expressed across normal untreated bone marrow stromal cell samples, regardless whether they are of single cell type or collective cell samples, purified or unpurified. As detailed under Materials & Methods, Gene-Spring was used to achieve the following data-analysis objectives: a) Filtering for genes reliably detected in each sample group by eliminating the genes with weak expressions that are statistically close to the background estimate. b) Filtering for genes that are active or "present" across replicates in each sample group. c) Exclusion of genes with weak expressions from genes "present" in each sample group. d) Preparation of master stromal cell gene list by intersecting gene lists from step (c) (as shown in FIG. 16). These steps have led to identification of a list of 2755 genes that are detected in at least 7 of 8 cUSC samples AND 4 of 5 cMPC samples AND 9 of 10 sMPC samples, i.e., in at least 20 of 23 stromal cell samples investigated. The main conclusions of the present report are based on this "stromal cell gene list" that is broadly representative of all 3 types of stromal cell samples investigated, and not on a gene list that is selective to sMPCs. A hallmark of the quality of microarray data can be discerned from hierarchical cluster analysis of replicates, which involves the principles of vector algebra. An array of numbers representing expression levels of a particular gene in terms of normalized signal intensity in a group of samples is considered a gene expression vector. Likewise, an array of numbers showing expression levels of a group of genes by a particular tissue sample is considered a tissue expression vector. In the case, applicants have 2755 gene expression vectors and 23 tissue or sample expression vectors. These vectors are amenable to algebraic treatment, facilitating calculation of similarity between any two gene- or tissue-expression vectors on the basis of a correlative metric or a similarity-measure employed, e.g., Euclidean angle. Grouping together of two samples on the basis of these principles signifies that they are most closely related out of all the samples in terms of their overall pattern of gene expression. Construction of a bone marrow stromal cell hierarchical tree has enabled visualization of global gene expression patterns across replicates and conditions. As shown in FIG. 17, stromal cell genes that are expressed at a relatively lower level in amplified samples (sMPCs) are clustered to the left of gene tree, genes that are more strongly expressed in sMPCs are prominently figured in the middle of gene tree, and genes that are expressed approximately at same level as in unamplified samples (cMPCs and cUSCs) are clustered to right of gene tree. Even more important as noticeable on the sample or experiment tree, hierarchical clustering segregated the members of each sample type into a separate group (cMPC, cUSC and SMPC). Note within each sample type, corresponding subject replicates clustered together with minor exceptions. This is a reflection on the reproducibility of the overall assay-procedures employed, which encompass a variety of stages and steps in addition to target RNA amplification prior to in vitro transcription (see Materials & Methods for details).

Figure 18:
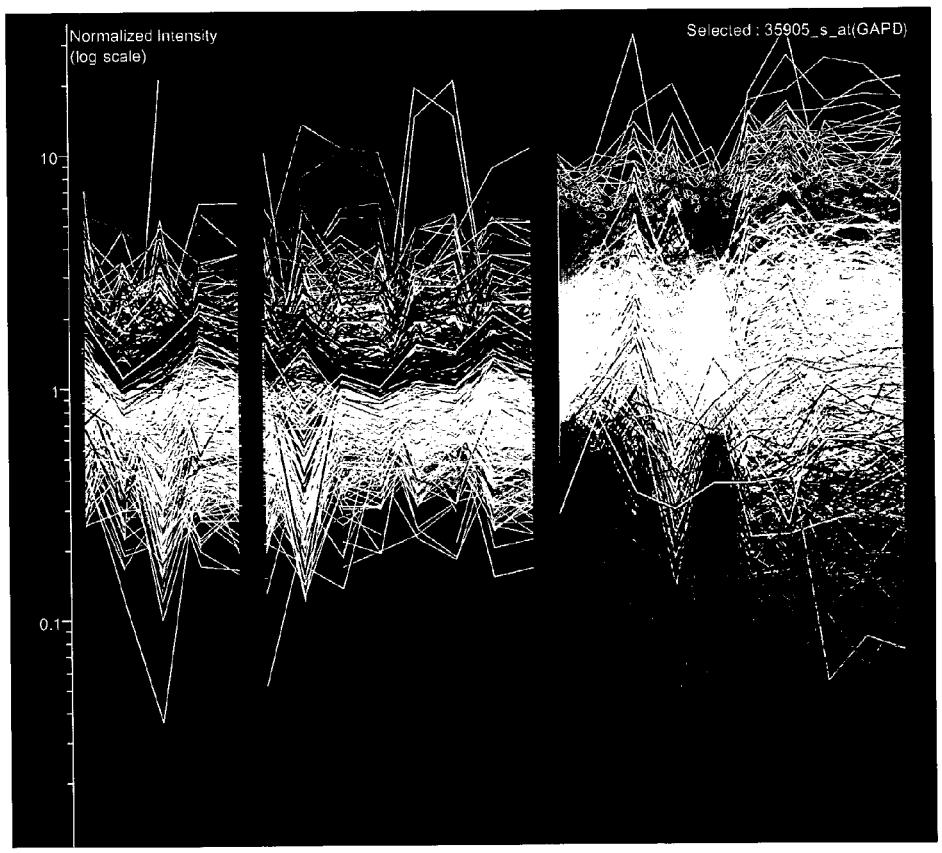
FIG. 18 shows composite gene-expression plots of 2755 stromal cell genes comparing collective purified stromal cell samples (cMPC), collective unpurified stromal cell samples (cUSC) and single-cell stromal cell samples (sMPC). Individual samples are represented on X-axis. Normalized intensity of gene expression is shown on Y-axis in log scale.

Finally, it is important to keep in mind that the measured level of a transcript following amplification does not necessarily provide a quantitative estimate of gene expression, but only provides a qualitative indication that the gene is transcriptionally active, which by itself is sufficient grounds for the conclusions arrived at in the present report. As shown in FIG. 18, the expression of genes within the stromal cell gene list ranges from 0.2 to 6 (on the log scale) in unamplified samples (cMPC and cUSC) and from 0.02 to 36 in amplified samples (sMPC), thus showing much greater variability in the amplified samples. For illustration purpose, the coloring of gene expression curves (following the linear color bar shown on the right) was based on the gene expression pattern of a particular single-cell sample, SCA1. Note that the genes that are detected at a low level in this sample (as indicated in blue) are not necessarily expressed at a low level in unamplified samples (as read by the log scale on Y-axis). In fact, a significant number of them are expressed at a high level in the unamplified samples. This finding together with the observation that amplified samples detected about 34% of genes as opposed to unamplified samples detecting about 46% of genes tested (Table 9), strikes a cautious note that some genes do not amplify at all by the method used, and other genes amplify to a sufficient degree to be detectable (shown in blue), while some other genes amplify to a degree equal to (in yellow) or surpassing (in red) the amounts in the collective samples. (The curve shown in white is the housekeeping gene, GAPD.) The statistical algorithm as implemented in the latest version of Microarray Analysis Suite (MAS v.5) determined that a gene within a given sample as positive, regardless of grading. To overcome the limitations of the amplification procedure employed, applicant focused only on genes that were positive in at least 20 of the 23 stromal cell samples investigated.

A stromal cell gene list is expected to be representative of typical stromal cell gene expression profile. Such master gene list forms the basis for derivation of all other stromal cell gene lists, organized in accordance with lineage or functional categories. As depicted in FIGS. 19 and 20, and listed in Tables 10 through Table 17, that were prepared according to lineage/functional assignment, the findings show that isolated single cells simultaneously express genes associated with diverse mesenchymal cell lineages, namely osteoblasts, muscle cells, fibroblasts, adipocytes, epithelial cells, endothelial cells, nerve cells and glial cells, providing confirmation of the existence of a pluridifferentiated progenitor cell type. By definition the stromal cell genes are present in at least 4 of 5 collective MPC samples AND 7 of 8 collective USC samples AND 9 of 10 single cell MPC samples; consequently, they are active in at least 20 of 23 samples tested, representing a typical genomic profile of stromal cells. The following gene lists are sub-lists of the master stromal cell gene list consisting of 2,755 genes. The stromal cell gene list contains a number of genes that are capable of causing endothelial differentiation and vasculogenesis within the marrow microenvironment; however, these genes themselves are not necessarily endothelial cell markers. In fact, stromal cells express a gene, EDF1, the expression of which inversely correlates with endothelial cell differentiation within the stromal cells. Of the 67AFFX control genes present on the U95A v2 chip, 22 genes are detected in at least 7 of 8 cUSC samples, 24 genes are detected in 4 of 5 cMPC samples and 19 genes are detected in at least in 9 of 10 sMPC samples. Thirteen of these genes are present in the stromal cell gene list, i.e., in 20 of the 23 samples investigated.

Figure 21:
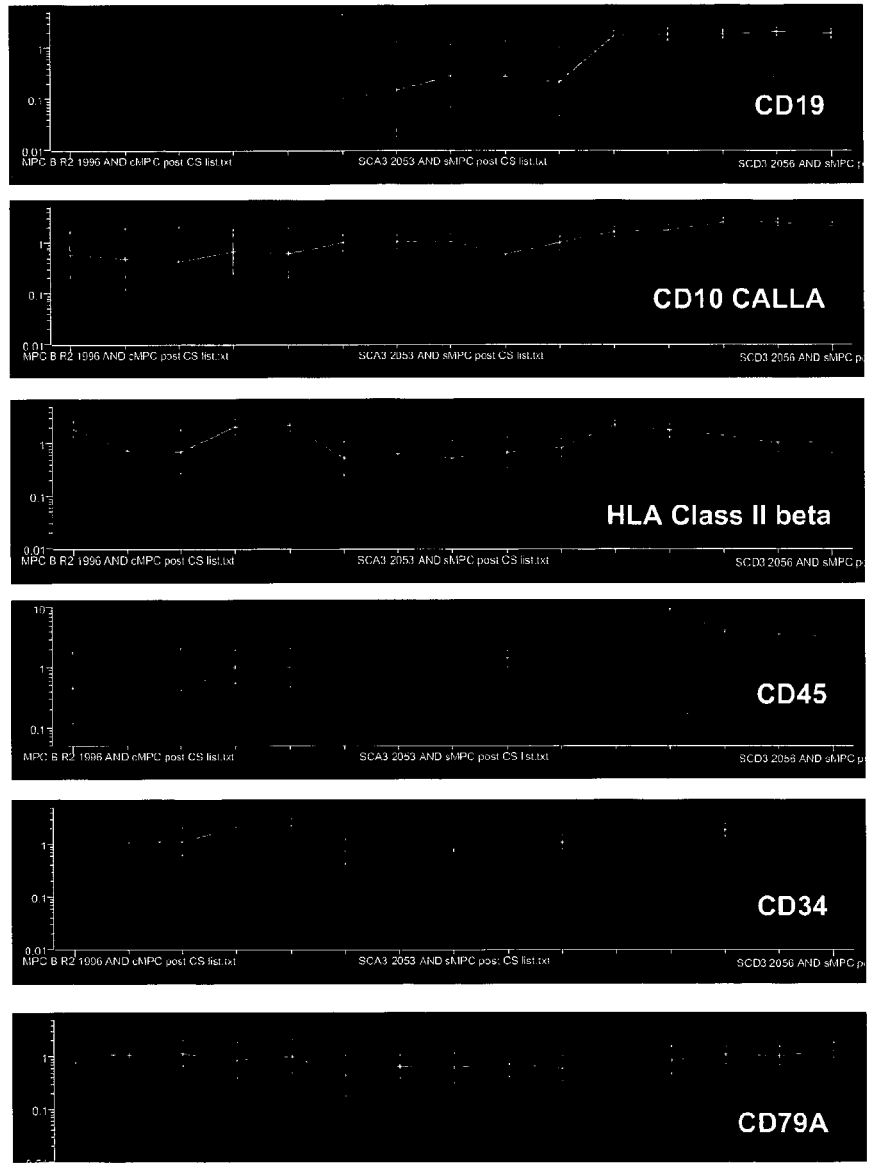
FIG. 21 shows gene-expression plots of representative precursor B-lymphocyte-associated genes by collective MPCs and single-cell MPCs. Individual samples are represented on X-axis. Signal intensity of a transcript in log scale normalized across samples is shown on Y-axis. Note that the CD markers that are traditionally associated with hematopoietic cells, CD45 (probe ID 40518_at), CD19 (ID 1116_at) and CD34 (ID 538_at), are expressed by sMPCs. CD45, when present, is more abundantly detected in single MPCs than in collective MPCs, and is particularly noticeable by wide range of log scale for CD45. The other pre-B cell associated markers that are expressed by sMPCs are CD10 (ID 1389_at), HLA-Dr (ID 33261_at) and CD79A (ID 34391_at). Samples 1–5, respectively, represent MPC A, MPC B R2, MPC C R2, MPC D R1, MPC D R2. Samples 6–15, respectively, represent SCA1, SCA2, SCA3, SCB1, SCB3, SCC1, SCC3, SCD1, SCD2, SCD3.

As evident from these gene lists, note that an isolated single stromal cell simultaneously expresses transcripts for epithelial and neuroectodermal cell types as well. Departing even further from the initial thinking, the findings add to the evidence that the MPCs within the Dexter system might represent a form or stage of the progenitor cell that is common to nonhematopoietic and hematopoietic cells. As depicted in FIG. 21, and listed in Table 18 through Table 21, the isolated single stromal cells express transcripts that are typical of hematopoietic cells, in particular precursor B cells. That BM stromal cells express CD10 (CALLA) is not novel since BM stromal cells as well as endometrial stromal cells and normal breast myoepithelial cells are known to express CD10. However, the expression of CD19, CD79A and immunoglobulin enhancer binding factors E12/E47 (proto-oncogene TCF3) by BM stromal cells is unforeseen, and forms the basis for postulating the existence of a common progenitor with B cell lineage. B-cell progenitors typically display the phenotype, (CD45 +/−, CD34 +/−, CD20 +/−, (CD10+, CD19+, CD79A+, HLA-Dr+), which as reported here is also displayed by isolated single stromal cells at least at the transcriptome level.

As described above, attached hereto is a compact disk containing the file "2755 Master Stromal Cell Ge," created on Oct. 3, 2002, the size of which is 499 kilobytes.

CD45 positivity by cMPC and cUSC samples is attributable to coexisting or contaminating hematopoietic cells in these samples as evidenced by concurrent positivity for myelomonocytic markers CD13, CD33 and CD14 (Table 21). However, a products or transcripts for CD45 and CD19 are most likely present in stromal cells at a basal level that is beyond the detection limits of conventional techniques, e.g., immunocytochemistry and Northern blotting, respectively. Conceivably, two rounds of amplification prior to IVT sufficiently increased their transcript levels to be detected by microarray analysis. In fact, the CD45 levels were severalfold lower in cMPC and cUSC compared to CD45 levels in sMPC, and CD19 was undetectable in unamplified samples. Finally, note that CD45 and CD19 are not isolated examples in this regard since applicant has identified at least 200 other genes that are uniquely present across sMPC samples but undetectable in cMPC and cUSC (FIG. 16).

The Issue of Stromal Cell—B Cell Connection

Although no anlage of Bursa of Fabricius exists in mammals, bone marrow is generally regarded as the site of B-cell generation. While the Dexter type stromal cell culture system was devised for investigation of hematopoiesis, specifically myelopoiesis (see Introduction), Whitlock and Witte developed another system for the study of B-lymphopoiesis. Whitlock-Witte cultures, like Friedenstein cultures, are grown in the absence of hydrocortisone and horse serum. When stromal cell layers in W—W cultures are seeded with fresh bone marrow as a source of B cell precursors or with purified B cell precursors, the latter then differentiate into mature B cells. On the other hand, although Dexter cultures do not promote B cell maturation, Dexter cultures do contain B cell precursors, which upon switching of culture conditions from those of Dexter to Whitlock-Witte, differentiate into mature B cells. While BM stromal cells in one form or another are definitely known to support B-lymphopoiesis, it has not been so clear as to whether stromal cells actually give rise to B-cell precursors. Evidence for a progenitor cell common to stromal cells and hematopoietic cells has been coming to light piecemeal in the form of isolated reports. 1) Singer J W et al in 1984 in the course of investigating bone marrow cultures from human patients with clonal myeloproliferative disorders showed that the nonhematopoietic stromal cells were derived from the same clonal progenitors that were involved by the hematopoietic neoplasm, as revealed by G6PD marker analysis. 2) Huss R et al in 1995 in the course of investigating a canine BM stromal cell line showed that the adherent stromal cells had "turned" into nonadherent hematopoietic cells, especially when the latter were cultured in presence of stem cell factor. 3) Pessina et al in 1997 showed that a particular murine stromal cell line upon stimulation with bFGF, expressed a B-cell phenotype, including CD45R and surface immunoglobulin. Although not by design, applicant shows for the first time that isolated single stromal cells express transcripts that are typically associated with hematopoietic lineage, namely, CD45 and CD19, as well as relevant proto-oncogenes and transcription factors. These results are strongly supportive of the existence of a progenitor cell common to bone marrow stromal cells and hematopoietic cells, particularly the bone marrow-derived (B) lymphocytes. Note that the study involves no feeder cells, no embryonic stem cells, no cell lines and no colonies of cells. Contrasting with the existing literature, the present study embarks on a new path of investigation entailing gene expression analysis of single, primary, normal human stromal cells that suggest a broad capacity for multilineage differentiation. On this model, progenitor cells express genes that are characteristic of any of the lineage fates that these cells are capable of adopting.

Perspective on Pluripotentiality vs. Pluridifferentiation

The present investigation involves isolated single stromal cells, consisting of 10 cells from 4 different individuals (FIG. 15). The cell culture system has been earlier characterized at light microscopic level, ultrastructural level and by karyotypic analysis, showing no evidence to suggest the artifacts discussed. Spontaneous cell fusion most likely involves monocytes/macrophages, forming multinucleated giant cells; however applicant observed no expression of myelomonocytic marker genes by isolated single stromal cells (Table 12). Keep in mind that the readout of in vivo transdifferentiation studies involves localization of different lineage cells in different tissues or organs; such a situation only requires fusion between two cell types (one donor cell and one recipient cell) for the investigators to believe the artifact as transdifferentiation. In contrast, applicant shows here presence of genes for a variety of cell-lineages simultaneously within the same cell. The probability of an array of different cell types fusing into one cell which then masquerading as a pluridifferentiated cell, and that too happening with 10 of 10 cells investigated, is in the opinion close to zero. There has never before been an opportunity to assess the extent of differentiation within these multipotential progenitor cells in molecular terms at the single-cell level. Theoretically, a) A stem cell can directly become a terminally differentiated cell, or b) A stem cell can enter a phase of multilineage differentiation prior to becoming a single-lineage, mature cell. To the knowledge, this study is the first systematic attempt to answer these questions at the single cell level by using the marrow stromal cells as a model. Although numerous forward-looking reviews exist on the topic of single-cell genomics, only a rare report is available on the actual application of this technology. Applicant has applied this frontier technology to show that a phase of multilineage differentiation indeed exists at least in Dexter-type stromal cells. Pluripotentiality of the bone marrow mesenchymal stromal cells in terms of their ability to become muscle cells, bone cells, fat cells and fibroblasts under select culture conditions has been described by other investigators. Instead of documenting another example of the phenomenon per se, the results provide an independent validation of the studies on transdifferentiation by casting light at the molecular basis of cellular plasticity. Finally, to borrow a concept from the clinical practice setting, a morphologically "poorly" differentiated neoplasm expressing hematopoietic markers is classified as a leukemia/lymphoma and treated as such. Similarly, a morphologically "undifferentiated" neoplasm marking for epithelial gene expression is diagnosed as a carcinoma and treated according to the protocols designed for a carcinoma. It is in this sense that applicant uses the term "pluridifferentiated" as opposed to "pluripotential" to characterize the BM stromal cells. Notwithstanding the semantics, applicant shows that the pluripotent stromal cells are pluridifferentiated, at least at the molecular level.

Conclusions

The findings of the present study clarify the on-going controversy as to the co-existence of multiple stromal cell types vs. one stromal cell type with co-expression of multiple phenotypes within the Dexter system of BM stromal cell cultures. An isolated single stromal cell from these cultures simultaneously expresses an array of phenotypes, i.e., osteoblasts, fibroblasts, muscle cells, adipocytes, epithelial cells, endothelial cells, neural cells/glial cells and even hematopoietic cells, in particular, B-lymphoid progenitors, thus documenting its wide differentiation repertoire. The significance of the findings is three-fold, $1^{st}$) They validate the hypothesis that the BM stromal cells express a pluridifferentiated progenitor cell phenotype, providing insight into the molecular basis of cellular plasticity as well as establishing the utility of single-cell genomics, $2^{nd}$) They provide evidence for a common progenitor for mesenchymal progenitors and BM-derived (B) lymphoid progenitors, $3^{rd}$) By establishing a comprehensive phenotype of cultured bone marrow stromal cells at single cell level for the first time, the findings pave the road for ultimate identification and investigation of these cells in fresh samples of marrow, normal as well as diseased, in which they occur at a low frequency.

Materials & Methods

Second-Tier Data-Analysis/Data Mining

The microarray data outputted by MAS v.5 (in the form of tab delimited text files) were imported into GeneSpring™ software version 4.2.1 (Silicon Genetics, Redwood City, Calif.). Following instructions accompanying GeneSpring, each gene was normalized to itself (per-gene normalization) by using the median of the gene's expression values over all the samples of an experimental group (or groups) and dividing each measurement for that gene by the corresponding median value, assuming that it was at least 0.01. The ratios were then log transformed to base e. No per-sample normalization was performed in GeneSpring since it was already accomplished as part of MAS v.5 analysis. The purpose of the above data transformations, including scaling and normalization, was to remove systematic error within and across conditions or experimental groups prior to further analysis. GeneSpring was used to achieve the following data-analysis objectives. a) Filtering for reliably present genes by eliminating the genes with weak expressions that are statistically close to the background estimate. As per the instructions accompanying GeneSpring, random error was estimated from control strength or median measurement level using the two-component global error model of Rocke-Lorenzato that assumes variability between replicates, as being similar for all genes showing similar measurement level. The formula for the error model of normalized expression levels can be written as follows:

$$S(\text{norm})^2 = a^2/C^2 + b^2$$

Where, S=standard error of normalized expression data, a & b are the two error components, a=an absolute or fixed error component impacting at lower measurement values, b=a relative or proportional error component impacting at higher measurement levels, and C=control strength. According to the manufacturer, a curve is fitted for each group of replicates, with standard error of normalized data on Y-axis vs. control strength on X-axis. At lower end of control strength, the, normalized standard error would be high and as the control strength increases, the standard error would decrease reaching a point where the curve flattens and data become more reliable. Control strength for each condition or sample group at which the above-referred two error components contribute equally, was calculated as follows, for collective MPCs, C=128.68; collective USCs, C=253.52; single-cell MPCs, C=348.32. Each condition was filtered for genes expressing signals greater than the respective control strength, thus eliminating the genes with weak expressions from each group. Note 7,196 genes (out of 12,625 gene probes tested) passed the restriction in case of cMPCs, 7,287 genes in case of cUSCs and 5,937 in case of sMPCs. Corresponding gene lists were created. b) Filtering for genes "present" across replicates in each sample group. GeneSpring's "Add data file restriction" feature was used to prepare the respective lists of genes that were present (or expressed or active) in a least 7 of 8 cUSC samples, 4 of 5 cMPC samples, and 9 of 10 sMPC samples. Note 5,204 genes (out of 12,625 gene probes tested) passed the restriction in case of cMPCs, 4,763 genes in case of cUSCs, and 3,124 genes in case of sMPCs. Corresponding gene lists were created. c) Exclusion of genes with weak expressions from genes "present" in each sample group. Respective gene-lists for each sample group from steps (a) and (b), were intersected via Venn diagrams. Note 5,204 genes passed the restriction in case of cMPCs, 4,761 genes in case of cUSCs, and 3,124 genes in case of sMPCs, which are almost identical to the numbers obtained as under step (b), except for a difference of 2 genes in case of cUSCs, thus providing no significant improvement in restricting the data beyond under step (b). This is a reflection of the high stringency of the criterion employed under step (b). The 2 genes in case of cUSCs that passed the restriction under step (b) but failed the combined restriction under step (c) did show weak expressions (raw signals ranging, 142–331). Corresponding gene lists were created. d) Preparation of master stromal cell gene list. Respective gene lists for the three sample groups from step (c) were intersected via Venn diagrams, resulting in identification of a list of 2,755 genes that are uniformly present or expressed in at least 20 of 23 stromal cell samples investigated. The stromal cell gene list thus arrived at contained genes that are representative of diverse mesenchymal lineages. Parenthetically, intersecting of gene lists corresponding to the three sample groups from step (b) resulted in a stromal cell gene list consisting of 2,756 genes, thus differing by 1 gene from the "official" master stromal cell gene list. e) Two-way hierarchical clustering of 2755 stromal cell genes based on expression profiles in 23 stromal cell samples. Only the data that were "cleaned up" of genes with weak expressions as outlined under step (a) were used for hierarchical clustering. This necessitated further processing of data in Microsoft Access prior to analysis by GeneSpring. Note that the data for each individual sample as outputted by MAS v.5 contained probe IDs, quantitative and qualitative data, as well as other information such as annotations and are readily recognizable by GeneSpring. In contrast, the gene list, resulting from step (a), contained only probe IDs and could not contain the data associated with each individual sample and was not recognizable by GeneSpring for inputting as part of an Experiment. Therefore, the microarray data for each group of individual samples (in Excel format) as well as the corresponding gene list for that group from step (a) (also in Excel format) were imported into an Access database. The genes that did not pass the test under step (a) were deleted from the microarray data for each individual sample by querying and intersecting with the appropriate post-clean-up gene list. The resulting data files were saved first as Excel files, then re-saved as tab delimited text files and then imported into GeneSpring. Per-gene normalization and log transformation were applied as described above. "Gene Tree" and "Experiment Tree" were constructed by applying a method similar to that of Eisen et al as implemented in GeneSpring and by using the stromal cell gene list and the following parameters: standard correlation as similarity measure; a minimum distance of 0.001; and a separation ratio of 0.5 in case of Gene Tree and 1.0 in case of Experiment Tree. f) Preparation of stromal cell gene lists as relevant to different cellular phenotypes and/or functions. The gene lists associated with distinct mesenchymal cell lineages or phenotypes, i.e., osteoblasts, fibroblasts, muscle cells and adipocytes, etc, were prepared using a combination of methods. These include 1) Visually inspecting the entire stromal-cell gene list for relevant key words. 2) Directly searching the stromal cell gene list by using key words of interest via "Advanced Find Genes" feature under Edit menu in GeneSpring and by selecting "Search Only Current Gene List". 3) Intersecting the stromal cell gene list with gene lists of interest from Gene Ontology lists, e.g., list of oncogenes, via Venn diagrams. g) Visualization of gene-expression plots. The expression pattern of a gene across a given group (or groups) of samples of interest was pictured via Gene Inspector window, utilizing desired display options.

Throughout this application, various publications, are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

The preceding descriptions of the invention are merely illustrative and should not be considered as limiting the scope of the invention in any way. From the foregoing description, one of ordinary skill in the art can easily ascertain the essential characteristics of the instant invention, and without departing from the spirit and scope thereof, can make various changes and/or modifications of the inventions to adapt it to various usages and conditions. As such, these changes and/or modifications are properly, equitably, and intended to be, within the full range of equivalence of the following claims.

TABLE 5

Summary of bone marrow stromal cell samples targeted for microarray analysis with an outline of the corresponding indicators of assay quality performance

|  | Unfractionated stromal cells (Collective USC, 8 replicates) | Percoll gradient-purified stromal cells (Collective MPC, 5 replicates) | LCM-dissected single cell samples (Single Cell MPC, 10 replicates) |
| --- | --- | --- | --- |
| Subject A | UNFR A | MPC A | SCA1, SCA2, SCA3 |
| Subject B | UNFR B,UNFR B R1, UNFR B R2 | MPC B R2 | SCB1, SCB3 |
| Subject C | UNFR C R1, UNFR C R2 | MPC C R2 | SCC1, SCC3 |
| Subject D | UNFR D R1, UNFR D R2 | MPC D R1, MPC D R2 | SCD1, SCD2, SCD3 |
| Amplification of RNA before IVT | No | No | Two rounds |
| Number of genes present (% of 12,625) | Mean: 46.63 SD: 5.95 | Mean: 46.54 SD:3.66 | Mean: 33.93 SD: 3.94 |
| 3':5' ratio, GAPD M33197 (Probe used as part of housekeeping control gene probe set) | Mean: 0.89 SD: 0.33 | Mean: 1.23 SD:0.53 | Mean: 6.76 SD: 2.97 |
| GAPD signal 35905_s_at (Probe used as part of standard gene probe set) | Mean: 130,723 SD: 36,990 | Mean: 164,593 SD: 40,204 (See Figure 5B.) | Mean: 43,235 SD: 14,413 (See Figure 5B.) |
| 3':5' ratio, ACTB X00351 (Probe used as part of housekeeping control gene probe set) | Mean: 1.44 SD: 0.60 | Mean: 2.29 SD: 1.57 | Mean: 57.92 SD: 67.82 |
| ACTB signal 32318_s_at (Probe used as part of standard gene probe set) | Mean: 86,104 SD: 18,458 | Mean: 100,383 SD: 28,427 (See Figure 5B.) | ♦Mean: 4,445 ♦SD: 884 (See Figure 5B.) |

Footnote to Table 5
Replicate samples shown under each sample type as indicated correspond to each subject. The replicates of collective USC and collective MPC represent cell-culture or biological replicates of stromal cells grown in parallel flasks (instead of technical replicates). We started with 27 samples of which 2 collective MPC samples and 2 single cell MPC samples failed either at the test chip stage or produced unusual results in terms of the number of genes present and/ or 3':5'ratios and were therefore excluded as outliers. Only those samples that were targeted for the data mining analysis are represented in this table. The statistics shown (means and SDs) were based on the number of sample replicates indicated in the top row of the table except for ACTB-signal for single cell MPCs (noted in the table by ♦), which were based on 9 replicates instead of 10.

TABLE 6

| Osteoblast/bone cell/bone disorders (Seshi, B) | | | | |
|---|---|---|---|---|
| Systematic | Common | Genbank | Description | Phenotype/Function |
| 38112_g_at | CSPG2 | X15998 | chondroitin sulfate proteoglycan 2 (versican) | |
| 38111_at | CSPG2 | X15998 | chondroitin sulfate proteoglycan 2 (versican) | |
| 38126_at | BGN | J04599 | biglycan | |
| 36976_at | CDH11 | D21255 | cadherin 11, type 2, OB-cadherin (osteoblast) | |
| 37315_f_at | BM036 | AI057607 | uncharacterized bone marrow protein BM036 | |
| 36996_at | OS-9 | U41635 | amplified in osteosarcoma | |
| 41202_s_at | OS4 | AF000152 | conserved gene amplified in osteosarcoma | |
| 671_at | SPARC | J03040 | secreted protein, acidic, cysteine-rich (osteonectin) | |
| 2087_s_at | CDH11 | D21254 | cadherin 11, type 2, OB-cadherin (osteoblast) | |
| 1916_s_at | c-fos | V01512 | Human cellular oncogene c-fos (complete sequence). | OMIM Notes: c-fos restricted to perichondrial growth regions of the cartilaginous skeleton. |
| 1915_s_at | c-fos | V01512 | Human cellular oncogene c-fos (complete sequence). | |
| 1388_g_at | VDR | J03258 | vitamin D (1,25-dihydroxyvitamin D3) receptor | ?Osteoporosis, involutional; Rickets, vitamin D-resistant |
| 1451_s_at | OSF-2 | D13666 | osteoblast specific factor 2 (fasciclin I-like) | |
| 32094_at | CHST3 | AB017915 | carbohydrate (chondroitin 6) sulfotransferase 3 | |
| 32307_s_at | COL1A2 | V00503 | collagen, type I, alpha 2 | Ehlers-Danlos syndrome, type VIIA2; Marfan syndrome, atypical; Osteogenesis imperfecta, 3 clinical forms, 166200, 166210; Osteoporosis, idiopathic |
| 32306_g_at | COL1A2 | J03464 | collagen, type I, alpha 2 | Ehlers-Danlos syndrome, type VIIA2; Marfan syndrome, atypical; Osteogenesis imperfecta, 3 clinical forms, 166200, 166210; Osteoporosis, idiopathic |
| 32305_at | COL1A2 | J03464 | collagen, type I, alpha 2 | Ehlers-Danlos syndrome, type VIIA2; Marfan syndrome, atypical; Osteogenesis imperfecta, 3 clinical forms, 166200, 166210; Osteoporosis, idiopathic |
| 34321_i_at | GS3786 | D87120 | predicted osteoblast protein | |
| 34342_s_at | SPP1 | AF052124 | secreted phosphoprotein 1 (osteopontin, bone sialoprotein I, early T-lymphocyte activation 1) | |
| 34763_at | CSPG6 | AF020043 | chondroitin sulfate proteoglycan 6 (bamacan) | |
| 222_at | EXT1 | S79639 | exostoses (multiple) 1 | Chondrosarcoma; Exostoses, multiple, type 1 |
| 36822_at | WAC | U51334 | WW domain-containing adapter with a coiled-coil region | Chondrosarcoma, extraskeletal myxoid |
| 41202_s_at | OS4 | AF000152 | conserved gene amplified in osteosarcoma | |
| 40790_at | BHLHB2 | AB004066 | basic helix-loop-helix domain containing, class B, 2; OMIM Notes: Alternative title, DEC1, expressed primarily in differentiated chondrocytes. | /transcription factor |

TABLE 7

Muscle/muscle disorders (Seshi, B)

| Systematic | Common | Genbank | Description | Phenotype/Function |
|---|---|---|---|---|
| 38251_at | MLC1SA | AI127424 | myosin light chain 1 slow a | |
| 38923_at | FRG1 | L76159 | FSHD (Facioscapulohumoral muscular dystrophy) region gene 1 | |
| 37012_at | CAPZB | U03271 | capping protein (actin filament) muscle Z-line, beta | |
| 37279_at | GEM | U10550 | GTP binding protein overexpressed in skeletal muscle | /GTPase |
| 36791_g_at | TPM1 | M19267 | tropomyosin 1 (alpha) | Cardiomyopathy, familial hypertrophic, 3 |
| 36790_at | TPM1 | M19267 | tropomyosin 1 (alpha) | Cardiomyopathy, familial hypertrophic, 3 |
| 36792_at | TPM1 | Z24727 | tropomyosin 1 (alpha) | |
| 36678_at | TAGLN2 | D21261 | transgelin 2 | |
| 36641_at | CAPZA2 | U03851 | capping protein (actin filament) muscle Z-line, alpha 2 | |
| 36931_at | TAGLN | M95787 | transgelin | |
| 37631_at | MYO1E | U14391 | myosin IE | |
| 41439_at | MYO1B | AJ001381 | myosin IB | |
| 40910_at | CAPZA1 | U56637 | capping protein (actin filament) muscle Z-line, alpha 1 | /binds barbed ends of actin filaments |
| 41187_at | MLC-B | U26162 | myosin regulatory light chain | |
| 41747_s_at | MEF2A | U49020 | Human myocyte-specific enhancer factor 2A (MEF2A) gene, last coding exon, and complete cds. | |
| 41738_at | CALD1 | M64110 | caldesmon 1 | |
| 41739_s_at | CALD1 | M83216 | caldesmon 1 | |
| 39791_at | ATP2A2 | M23114 | ATPase, Ca++ transporting, cardiac muscle, slow twitch 2 | Darier disease |
| 39790_at | ATP2A2 | M23115 | ATPase, Ca++ transporting, cardiac muscle, slow twitch 2 | Darier disease |
| 39378_at | BECN1 | U17999 | beclin 1 (coiled-coil, myosin-like BCL2 interacting protein) | |
| 40488_at | DMD | M18533 | dystrophin (muscular dystrophy, Duchenne and Becker types) | Becker muscular dystrophy; Cardiomyopathy, dilated, X-linked; Duchenne muscular dystrophy |
| 40438_at | PPP1R12A | D87930 | protein (myosin) phosphatase 1, regulatory (inhibitor) subunit 12A | OMIM Notes: Regulates the interaction of actin and myosin downstream of the guanosine triphosphatase Rho. |
| 32838_at | smooth muscle myosin heavy chain isoform SMemb | S67247 | Homo sapiens cDNA: FLJ23324 fis, clone HEP12482, highly similar to HUMMYOHCB Human nonmuscle myosin heavy chain-B (MYH10) mRNA | |
| 32755_at | ACTA2 | X13839 | actin, alpha 2, smooth muscle, aorta | |
| 33994_g_at | MLC | M22919 | Human nonmuscle/smooth muscle alkali myosin light chain gene, complete cds. | |
| 33447_at | MLCB | X54304 | myosin, light polypeptide, regulatory, non-sarcomeric (20 kD) | |
| 32313_at | TPM2 | M12125 | tropomyosin 2 (beta) | OMIM Notes: Fibroblast and muscle isoforms result from alternative splicing on exons 6 and 9. |
| 35362_at | MYO10 | AB018342 | myosin X | |
| 34306_at | MBNL | AB007888 | muscleblind-like (Drosophila) | |
| 36989_at | DAG1 | L19711 | dystroglycan 1 (dystrophin-associated glycoprotein 1) | |
| 40022_at | FCMD | AB008226 | Fukuyama type congenital muscular dystrophy (fukutin) | ?Walker-Warburg syndrome; Muscular dystrophy, Fukuyama congenital |
| 39031_at | COX7A1 | AA152406 | cytochrome c oxidase subunit VIIa polypeptide 1 (muscle) | |
| 35729_at | MYO1D | AB018270 | myosin ID | |
| 32378_at | PKM2 | M26252 | pyruvate kinase, muscle | |
| 40375_at | EGR3 | X63741 | early growth response 3; OMIM Notes: Expressed in deveolping muscle spindles. | |
| 1637_at | MAPKAPK3 | U09578 | mitogen-activated protein kinase-activated protein kinase 3; OMIM Notes: Expressed especially high in heart and skeletal muscle. | |

TABLE 7-continued

Muscle/muscle disorders (Seshi, B)

| Systematic | Common | Genbank | Description | Phenotype/Function |
|---|---|---|---|---|
| 40399_r_at | MEOX2 | A1743406 | mesenchyme homeobox 2 (growth arrest-specific homeobox). OMIM Notes: Important regulator of myogenesis. | |
| 39565_at | BMPR1A | Z22535 | bone morphogenetic protein receptor, type IA. OMIM Notes: Alternative title, activin receptor-like kinase 3; ALK3. Expressed almost exclusively in skeletal muscle with weak expression in heart and placenta. | Polyposis, juvenile intestinal |
| 41449_at | SGCE | AJ000534 | sarcoglycan, epsilon | Dystonia, myoclonic |

TABLE 8

Fibroblast (Seshi, B)

| Systematic | Common | Genbank | Description | Phenotype/Function |
|---|---|---|---|---|
| 39333_at | COL4A1 | M26576 | Human alpha-1 collagen type IV gene, exon 52. | |
| 37037_at | P4HA1 | M24486 | procollagen-proline, 2-oxoglutarate 4-dioxygenase (proline 4-hydroxylase), alpha polypeptide I | |
| 36666_at | P4HB | M22806 | precursor; Human prolyl 4-hydroxylase beta-subunit and disulfide isomerase (P4HB) gene, exon 11, clones 6B-(1,3,5,6). | |
| 41504_s_at | MAF | AF055376 | v-maf musculoaponeurotic fibrosarcoma oncogene homolog (avian) | |
| 39757_at | SDC2 | J04621 | syndecan 2 (heparan sulfate proteoglycan 1, cell surface-associated, fibroglycan) | |
| 39945_at | FAP | U09278 | fibroblast activation protein, alpha | OMIM Notes: Expressed in fetal normal mesenchymal tissues and stromal fibroblasts within common types of epithelial tumors. |
| 32835_at | MAFF | AA725102 | v-maf musculoaponeurotic fibrosarcoma oncogene homolog F (avian) | |
| 32535_at | FBN1 | X63556 | fibrillin 1 (Marfan syndrome) | Ectopia lentis, familial; Marfan syndrome; MASS syndrome; Shprintzen-Goldberg syndrome |
| 2057_g_at | FGFR1 | M34641 | fibroblast growth factor receptor 1 (fms-related tyrosine kinase 2, Pfeiffer syndrome) | Jackson-Weiss sydnrome; Pfeiffer syndrome |
| 1380_at | FGF7 | M60828 | fibroblast growth factor 7 (keratinocyte growth factor) | OMIM Notes: May play a role in mesenchymal stimulation of epithelial cell proliferation. |
| 32313_at | TPM2 | M12125 | tropomyosin 2 (beta) | OMIM Notes: Fibroblast and muscle isoforms result from alternative splicing on exons 6 and 9. |
| 31720_s_at | FN1 | M10905 | fibronectin 1 | |
| 31719_at | FN1 | X02761 | fibronectin 1 | |
| 35835_at | PDL-108 | AB019409 | periodontal ligament fibroblast protein | |
| 34390_at | P4HA2 | U90441 | procollagen-proline, 2-oxoglutarate 4-dioxygenase (proline 4-hydroxylase), alpha polypeptide II | |

TABLE 9

Adipocyte (Seshi, B, et al)

| Probe ID | Gene Name | Genbank ID | Description | OMIM Notes |
|---|---|---|---|---|
| 34378_at | ADRP | X97324 | adipose differentiation-related protein (adipophilin)/lipid-droplet binding/ adipocyte-specific | mRNA levels are induced rapidly and maximally after triggering adipocyte differentiation. |
| 40282_s_at | DF | M84526 | D component of complement (adipsin) | High level of expression in fat. |
| 33337_at | DEGS | AF002668 | degenerative spermatocyte homolog, lipid desaturase (Drosophila) | |
| 39673_i_at | ECM2 | AB011792 | extracellular matrix protein 2, female organ and adipocyte specific | |
| 39674_r_at | ECM2 | AB011792 | extracellular matrix protein 2, female organ and adipocyte specific | |
| 31504_at | HDLBP | M64098 | high density lipoprotein binding protein (vigilin) | |
| 37542_at | LHFPL2 | D86961 | lipoma HMGIC fusion partner-like 2 | |
| 36073_at | NDN | U35139 | necdin homolog (mouse)/Prader-Willi syndrome | |
| 37122_at | PLIN | AB005293 | Perilipin (Did not meet the criteria to be included in stromal cell gene list because it was positive in 5 of 5 cMPC and 9 of 10 sMPCs, but only 6 of 8 cUSc instead of 7 of 8 cUSC samples). | Plays an important role in adipocyte metaboloism. Has significant sequence relationship with ADRP. |

TABLE 10

Epithelial cell/carcinoma (Seshi, B)

| Systematic | Common | Genbank | Description | Phenotype/Function |
|---|---|---|---|---|
| 38590_r_at | PTMA | M14630 | prothymosin, alpha (gene sequence 28) | |
| 38589_i_at | PTMA | M14630 | prothymosin, alpha (gene sequence 28) | |
| 38610_s_at | KRT10; KPP | X14487 | unnamed protein product; Human gene for acidic (type I) cytokeratin 10. | Epidermolytic hyperkeratosis |
| 37326_at | A4 | U93305 | integral membrane protein; swiss-prot accession: O04901; may play role in cell differentiation in intestinal epithelium | |
| 36812_at | BCAR3 | U92715 | breast cancer anti-estrogen resistance 3 | |
| 36953_at | MADH4 | U44378 | MAD, mothers against decapentaplegic homolog 4 (Drosophila) | Pancreatic cancer; Polyposis, juvenile intestinal |
| 36852_at | N33 | U42349 | Putative prostate cancer tumor suppressor | |
| 36851_g_at | N33 | U42360 | 39 kDa protein; Human N33 protein form 2 (N33) gene, exon 11 and complete cds. | ?Prostate cancer, susceptibility to |
| 37762_at | EMP1 | Y07909 | epithelial membrane protein 1 | /receptor |
| 37731_at | EPS15 | Z29064 | epidermal growth factor receptor pathway substrate 15 | |
| 40856_at | SERPINF1; PEDF; EPC-1 | U29953 | PEDF; Human pigment epithelium-derived factor gene, complete cds. | |
| 41431_at | ICK | AB023153 | intestinal cell kinase | |
| 39363_at | BC-2 | AF042384 | putative breast adenocarcinoma marker (32 kD) | |
| 39631_at | EMP2 | U52100 | epithelial membrane protein 2 | |
| 39542_at | ENC1 | AF059611 | ectodermal-neural cortex (with BTB-like domain) | /associates with p110(RB) |
| 40454_at | FAT | X87241 | FAT tumor suppressor homolog 1 (Drosophila) | |
| 32781_f_at | BPAG1 | AA058762 | bullous pemphigoid antigen 1 (230/240 kD) | |
| 32780_at | BPAG1 | AB018271 | bullous pemphigoid antigen 1 (230/240 kD) | |
| 32329_at | KRTHB6 | X99142 | keratin, hair, basic, 6 (monilethrix) | Monilethrix |
| 34005_at | PIGR | X73079 | polymeric immunoglobulin receptor, expressed in glomerular epithelial cells. | /Binds and transports polymeric immunoglobulin |

TABLE 10-continued

Epithelial cell/carcinoma (Seshi, B)

| Systematic | Common | Genbank | Description | Phenotype/Function |
|---|---|---|---|---|
| 1846_at | LGALS8 | L78132 | lectin, galactoside-binding, soluble, 8 (galectin 8); OMIM Notes: Expressed in prostate carcinoma cells but only rarely in prostatic hypertrophy. | |

TABLE 11

Endothelial cell (Seshi, B)

| Systematic | Common | Genbank | Description | Phenotype/Function |
|---|---|---|---|---|
| 32755_at | ACTA2 | X13839 | actin, alpha 2, smooth muscle, aorta | |
| 39315_at | ANGPT1 | D13628 | angiopoietin 1 | |
| 1929_at | ANGPT1 | U83508 | angiopoietin 1 | /ligand for the TIE2 receptor |
| 40387_at | EDG2 | U80811 | endothelial differentiation, lysophosphatidic acid (LPA) G-protein-coupled receptor, 2 | |
| 40874_at | EDF1 | AJ005259 | endothelial differentiation-related factor 1; OMIM Notes: EDF1 level inversely correlates with the level of endothelial differentiation. Inhibition of EDF1 expression promotes endothelial cell differentiation. It is postulated that EDF1 may function as a bridging molecule that interconnects regulatory proteins and the basal transcriptional machinery, thus modulating the transcription of the genes involved in endothelial differentiation. | |
| 37907_at | F8A; DXS522E | M34677 | Factor VIII-associated gene 1; CpG island protein; Human nested gene protein gene, complete cds. | |
| 41433_at | VCAM1 | M73255 | Human vascular cell adhesion molecule-1 (VCAM1) gene, complete CDS. | |
| 36988_at | TNFAIP1 | M80783 | tumor necrosis factor, alpha-induced protein 1 (endothelial); OMIM Notes: Involved in the promary response of the endothelium to TNF. | |
| 583_s_at | VCAM1 | M30257 | vascular cell adhesion molecule 1 | |
| 1953_at | VEGF | AF024710 | vascular endothelial growth factor | |
| 36100_at | VEGF | AF022375 | vascular endothelial growth factor | |
| 37268_at | VEGFB | U43368 | vascular endothelial growth factor B | |
| 159_at | VEGFC | U43142 | vascular endothelial growth factor C | /ligand and activator of the receptor tyrosine kinase Flt4 |

TABLE 12

Nerve cell/neuroendocrine/neurologic disorders (Seshi, B)

| Systematic | Common | Genbank | Description | Phenotype/Function |
|---|---|---|---|---|
| 37298_at | GABARAP | AF044671 | GABA(A) receptor-associated protein | |
| 37692_at | DBI GABARAPL | AI557240 | diazepam binding inhibitor (GABA receptor modulator, acyl-Coenzyme A binding protein) | |
| 35767_at | 2 GABARAPL | AI565760 | GABA(A) receptor-associated protein-like 2 | |
| 35785_at | 1 | W28281 | GABA(A) receptor-associated protein like 1 | |
| 38406_f_at | PTGDS | AI207842 | prostaglandin D2 synthase (21 kD, brain) | |
| 38657_s_at | CLTA | M20471 | clathrin, light polypeptide (Lca), brain specific insertion sequences | |
| 38653_at | PMP22 | D11428 | peripheral myelin protein 22 | Charcot-Marie-Tooth disease with deafness; |

TABLE 12-continued

Nerve cell/neuroendocrine/neurologic disorders (Seshi, B)

| Systematic | Common | Genbank | Description | Phenotype/Function |
|---|---|---|---|---|
| | | | | Charcot-Marie-Tooth neuropathy-1A; Dejerine-Sottas disease; Neuropathy, recurrent, with pressure palsies |
| 38291_at | PENK | J00123 | preproenkephalin (; Human enkephalin gene: exon 3 and 3'flank. | |
| 39072_at | MXI1 | L07648 | MAX interacting protein 1 | Neurofibrosarcoma; Prostate cancer, susceptibility to/ transcription factor; forms heterodimers with Max protein |
| 38841_at | GDBR1 | AF068195 | putative glialblastoma cell differentiation-related | |
| 38818_at | SPTLC1 | Y08685 | serine palmitoyltransferase, long chain base subunit 1 | Neuropathy, hereditary sensory and autonomic, type 1 |
| 36990_at | UCHL1 | X04741 | ubiquitin carboxyl-terminal esterase L1 (ubiquitin thiolesterase), neuron-specific. OMIM Notes: Highly specific to neurons and to cells of the diffuse neuroendocrine system and their tumors. | Parkinson disease, familial |
| 37005_at | NBL1 | D28124 | neuroblastoma, suppression of tumorigenicity 1 | |
| 37286_at | NRCAM | AB002341 | neuronal cell adhesion molecule | |
| 36667_at | PYGB | U47025 | phosphorylase, glycogen; brain | |
| 36965_at | ANK3 | U13616 | ankyrin 3, node of Ranvier (ankyrin G) | /peripheral proteins believed to act as membrane-cytoskeleton linker molecules |
| 38040_at | SPF30 | AF107463 | splicing factor 30, survival of motor neuron-related | |
| 37958_at | BCMP1 | AL049257 | brain cell membrane protein 1 | |
| 41221_at | PGAM1 | J04173 | phosphoglycerate mutase 1 (brain) | |
| 40936_at | CRIM1 | AI651806 | cysteine-rich motor neuron 1 | |
| 41091_at | FALZ | U05237 | fetal Alzheimer antigen. OMIM Notes: Abnormally expressed in fetal brain. The corresponding antibody ALZ50 recognizes neurofibrillary pathology associated with Alzheimer's disease. | |
| 41136_s_at | APP | Y00264 | amyloid beta (A4) precursor protein (protease nexin-II, Alzheimer disease) | Alzheimer disease-1, APP-related; Amyloidosis, cerebroarterial, Dutch type; Schizophrenia, chronic |
| 763_at | GMFB | AB001106 | glia maturation factor, beta | |
| 641_at | PSEN1 | L76517 | presenilin 1 (Alzheimer disease 3) | Alzheimer disease, familial, with spastic paraparesis and unusual plaques; Alzheimer disease-3 |
| 39793_at | GBAS | AF029786 | glioblastoma amplified sequence | |
| 40023_at | BDNF | X60201 | brain-derived neurotrophic factor | |
| 39687_at | E46L | AI524873 | like mouse brain protein E46 | |
| 39686_g_at | E46L | AL050282 | like mouse brain protein E46 | |
| 39542_at | ENC1 | AF059611 | ectodermal-neural cortex (with BTB-like domain) | /associates with p110(RB). OMIM Notes: Expressed highest in brain. |
| 40193_at | ENO2 | X51956 | Human ENO2 gene for neuron specific (gamma) enolase. | |
| 40121_at | HIP2 | U58522 | huntingtin interacting protein 2 | |
| 40467_at | SDHD | AB006202 | succinate dehydrogenase complex, subunit D, integral membrane protein | Paragangliomas, familial central nervous system; Paragangliomas, familial nonchromaffin, 1, with and without deafness; Pheochromocytoma |
| 40281_at | NEDD5 | D63878 | neural precursor cell expressed, developmentally down-regulated 5 | |
| 32824_at | CLN2 | AF039704 | deficient in late-infantile neuronal ceroid lipofuscinosis; Homo sapiens lysosomal pepstatin insensitive protease (CLN2) gene, complete cds. | Ceroid-lipofuscinosis, neuronal 2, classic late infantile |

TABLE 12-continued

Nerve cell/neuroendocrine/neurologic disorders (Seshi, B)

| Systematic | Common | Genbank | Description | Phenotype/Function |
|---|---|---|---|---|
| 32607_at | BASP1 | AF039656 | brain abundant, membrane attached signal protein 1 | |
| 33817_at | D10S102 | S63912 | FBRNP; heterogeneous ribonucleoprotein homolog; This sequence comes from FIG. 3; D10S102 = FBRNP [human, fetal brain, mRNA, 3043 nt]. | |
| 33942_s_at | STXBP1 | AF004563 | syntaxin binding protein 1 | /implicated in vesicle trafficking and neurotransmitter release |
| 1659_s_at | RHEB2 | D78132 | Ras homolog enriched in brain 2 | |
| 1695_at | NEDD8 | D23662 | neural precursor cell expressed, developmentally down-regulated 8 | |
| 2053_at | CDH2 | M34064 | cadherin 2, type 1, N-cadherin (neuronal) | |
| 216_at | PTGDS | M98539 | Human prostaglandin D2 synthase gene, exon 7, brain | |
| 32102_at | SACS | AB018273 | spastic ataxia of Charlevoix-Saguenay (sacsin) | Spastic ataxia, Charlevoix-Saguenay type |
| 31896_at | NAG | AL050281 | neuroblastoma-amplified protein | |
| 35681_r_at | ZFHX1B | AB011141 | zinc finger homeobox 1b. OMIM Notes: SMAD-interacting protein 1 (SMADIP1) appears to be essential to embryonic neural and neural crest development. | Hirschsprung disease-mental retardation syndrome; Hirschsprung disease-mental retardation syndrome without Hirschsprung disease |
| 35268_at | AXOT | AL050171 | axotrophin | |
| 36190_at | CDR2 | M63256 | cerebellar degeneration-related protein (62 kD) | |
| 36609_at | SLC1A3 | D26443 | solute carrier family 1 (glial high affinity glutamate transporter), member 3 | |
| 35973_at | HYPH | AB023163 | Huntingtin interacting protein H | |
| 36142_at | SCA1 | X79204 | spinocerebellar ataxia 1 (olivopontocerebellar ataxia 1, autosomal dominant, ataxin 1) | Spinocerebellar ataxia-1 |
| 34817_s_at | A2LP | U70671 | ataxin 2 related protein | |
| 34777_at | ADM | D14874 | adrenomedullin | |
| 34394_at | ADNP | AB018327 | activity-dependent neuroprotector | |
| 32606_at | BASP1 | AA135683 | brain abundant, membrane attached signal protein 1 | |
| 38233_at | HOMER-3 | AF093265 | Homer, neuronal immediate early gene, 3 | |
| 36998_s_at | SCA2 | Y08262 | spinocerebellar ataxia 2 (olivopontocerebellar ataxia 2, autosomal dominant, ataxin 2) | Spinocerebellar ataxia-2 |
| 35150_at | TNFRSF5 | X60592 | tumor necrosis factor receptor superfamily, member 5 | Immunodeficiency with hyper-IgM, type 3 |
| 34166_at | SLC6A7 | S80071 | solute carrier family 6 (neurotransmitter transporter, L-proline), member 7 | |
| 34265_at | SGNE1 | Y00757 | secretory granule, neuroendocrine protein 1 (7B2 protein) | |
| 654_at | MXI1 | L07648 | MAX interacting protein 1 | Neurofibrosarcoma; Prostate cancer, susceptibility to/ transcription factor; forms heterodimers with Max protein |
| 37945_at | BACH | U91316 | brain acyl-CoA hydrolase | |
| 39685_at | E46L | AL050282 | like mouse brain protein E46 | |
| 33769_at | MPZL1 | AF087020 | myelin protein zero-like 1 | |
| 39356_at | NEDD4L | AB007899 | neural precursor cell expressed, developmentally down-regulated 4-like | |
| 38800_at | STMN2 | D45352 | stathmin-like 2; OMIM Notes: Neuronal growth-associated protein SCG10. | |
| 36933_at | NDRG1 | D87953 | N-myc downstream regulated gene 1 | Neuropathy, hereditary motor and sensory, Lom type |
| 40140_at | ZFP103 | D76444 | zinc finger protein 103 homolog (mouse); OMIM Notes: Alternative title, KF1, expressed in normal cerebellum and Alzheimer disease | |

TABLE 12-continued

Nerve cell/neuroendocrine/neurologic disorders (Seshi, B)

| Systematic | Common | Genbank | Description | Phenotype/Function |
|---|---|---|---|---|
| 1452_at | LMO4 | U24576 | cerebral cortex, but not in normal cerebral cortex. LIM domain only 4 | OMIM Notes: is highly expressed in the cranial neural crest cells, somite, dorsal limb bud mesenchyme, motor neurons, Schwann cell progenitors, and T-lymphocyte lineage. |
| 1058_at | WASF3 | S69790 | WAS protein family, member 3 | |

TABLE 13

Drosophila and/or homeotic genes (Seshi, B)

| Systematic | Common | Genbank | Description | Phenotype/Function |
|---|---|---|---|---|
| 38288_at | SNAI2 | U69196 | snail homolog 2 (Drosophila). OMIM Notes: Neural crest transcription factor SLUG. A zinc fanger protein that plays an important role in the transition of epithelial to mesenchymal characteristics within the neural crest. | |
| 39037_at | MLLT2 | L13773 | myeloid/lymphoid or mixed-lineage leukemia (trithorax homolog, Drosophila); translocated to, 2 | |
| 39070_at | SNL | U03057 | singed-like (fascin homolog, sea urchin) (Drosophila). OMIM Notes: Positive in dendritic cells of lymph nodes and Reed-Sternberg cells. | |
| 39164_at | ARIH2 | AF099149 | ariadne homolog 2 (Drosophila). OMIM Notes: Upregulated during retinoic acid-induced granulocytic differentiation of APL cells. | |
| 38750_at | NOTCH3 | U97669 | Notch homolog 3 (Drosophila). OMIM Notes: Promotes the differentiation of astroglia from multipotent progenitors. | Cerebral (autosomal dominant) arteriopathy with subcortical infarcts and leukoencephalopathy (CADASIL) |
| 38944_at | MADH3 | U68019 | MAD, mothers against decapentaplegic homolog 3 (Drosophila) | OMIM Notes: SMAD3 signal transduction important in the regulation of muscle-specific genes. |
| 37693_at | NUMB | L40393 | numb homolog (Drosophila) | OMIM Notes: Numb directs neuronal cell fate decisions. |
| 40004_at | SIX1 | X91868 | sine oculis homeobox homolog 1 (Drosophila) | OMIM Notes: Expressed in adult skeletal muscle, and in multiple tumors including mammary carcinoma. |
| 39610_at | HOXB2 | X16665 | homeo box B2 | OMIM Notes: Essential for motor neuron development. Within the hematopoietic compartment, expressed specifically in erythromegakaryocytic cell lines. |
| 40575_at | DLG5 | AB011155 | discs, large (Drosophila) homolog 5 | OMIM Notes: Expressed in prostate gland epithelial cells. |
| 40570_at | FOXO1A | AF032885 | forkhead box O1A (rhabdomyosarcoma) | Rhabdomyosarcoma, alveolar. OMIM Notes: Activates myogenic transcription program. |
| 40127_at | PMX1 | M95929 | paired mesoderm homeo box 1 | OMIM Notes: Expressed in cardiac, skeletal and smooth muscle tissues. |

TABLE 13-continued

Drosophila and/or homeotic genes (Seshi, B)

| Systematic | Common | Genbank | Description | Phenotype/Function |
|---|---|---|---|---|
| 40454_at | FAT | X87241 | FAT tumor suppressor homolog 1 (Drosophila) | OMIM Notes: Expressed in many epithelial, some endothelial and smooth muscle cells. |
| 40328_at | TWIST | X99268 | twist homolog (acrocephalosyndactyly 3; Saethre-Chotzen syndrome) (Drosophila) | Saethre-Chotzen syndrome. OMIM Notes: Required for cranial neural tube morphogenesis. |
| 33222_at | FZD7 | AB017365 | frizzled homolog 7 (Drosophila) | OMIM Notes: Highest expression adult skeletal muscle and fetal kidney. FZD7 dependent PKC signaling controls cell sorting behaviour in the mesoderm. |
| 32696_at | PBX3 | X59841 | pre-B-cell leukemia transcription factor 3 | |
| 33337_at | DEGS | AF002668 | degenerative spermatocyte homolog, lipid desaturase (Drosophila); adipocyte associated. | |
| 1857_at | MADH7 | AF010193 | MAD, mothers against decapentaplegic homolog 7 (Drosophila) | OMIM Notes: MAD proteins were originally defined in Drosophila as essential components of the signaling pathways of the TGF-beta receptor family (e.g., TGFBR1). MADH7 and MADH6 as shown by IHC and ISH are predominantly expressed in vascular endothelium. |
| 1955_s_at | MADH6 | AF035528 | MAD, mothers against decapentaplegic homolog 6 (Drosophila) | /inhibitor of BMP signaling |
| 1013_at | MADH5 | U59913 | MAD, mothers against decapentaplegic homolog 5 (Drosophila) | OMIM Notes: SMAD5 plays a critical role in the signaling pathway by which TGF-beta inhibits the proliferation of human hematopoietic progenitor cells. |
| 1453_at | MADH2 | U68018 | MAD, mothers against decapentaplegic homolog 2 (Drosophila) | |
| 1433_g_at | MADH3 | U68019 | MAD, mothers against decapentaplegic homolog 3 (Drosophila) | OMIM Notes: SMAD2/SMAD3 signal transduction appears to be important in the regulation of muscle-specific genes. |
| 35681_r_at | ZFHX1B | AB011141 | zinc finger homeobox 1b. OMIM Notes: SMAD-interacting protein 1 (SMADIP1) appears to be essential to embryonic neural and neural crest development, | Hirschsprung disease-mental retardation syndrome; Hirschsprung disease-mental retardation syndrome without Hirschsprung disease |
| 35226_at | EYA2 | U71207 | eyes absent homolog 2 (Drosophila) | OMIM Notes: Expressed in extensor tendons, and in lens fibers and participates inconnective tissue patterning. |
| 36308_at | ZIC1 | D76435 | Zic family member 1 (odd-paired homolog, Drosophila) | OMIM Notes: Specifically expressed in nervous tissue and in particular cerebellar granule cells, potential biomarker for cerebellar granule cell lineage and medulloblastoma. |
| 34306_at | MBNL | AB007888 | muscleblind-like (Drosophila) | OMIM Notes: Expressed in skeletal muscle myoblasts, also in lymphoblastoid cell lines. |

TABLE 13-continued

Drosophila and/or homeotic genes (Seshi, B)

| Systematic | Common | Genbank | Description | Phenotype/Function |
|---|---|---|---|---|
| 33710_at | C3F | U72515 | putative protein similar to nessy (Drosophila) | OMIM Notes: Expressed in fibroblasts and hepatocytes. |

TABLE 14

B-cell/B-cell neoplasms (Seshi, B)

| Systematic | Common | Genbank | Description | Phenotype/Function |
|---|---|---|---|---|
| 41562_at | BMI1 | L13689 | B lymphoma Mo-MLV insertion region (mouse) | /proto-oncogene |
| 37294_at | BTG1 | X61123 | B-cell translocation gene 1 anti-proliferative | |
| 38418_at | CCND1 | X59798 | cyclin D1 (PRAD1: parathyroid adenomatosis 1) | Centrocytic lymphoma; Leukemia/lymphoma, B-cell, 1; Multiple myeloma; Parathyroid adenomatosis 1 |
| 37730_at | p100 | U22055 | EBNA-2 co-activator (100 kD); OMIM Notes: EBNA-2 activates transcription of specific genes and is essential for EBV-mediated B-lymphocyte transformation. | /associates with the EBV nuclear protein 2 acidic domain |
| 466_at | GTF2I | U77948 | general transcription factor II, I; OMIM Notes: Alternative title, BTK-associated protein, 135 kD (BAP135). Bruton's tyrosine kinase (BTK) is essential for B-cell activation and phosphorylates BAP135 in B cells. | |
| 36875_at | IBTK | AL050018 | inhibitor of Bruton's tyrsoine kinase | |
| 38438_at | NFKB1 | M58603 | nuclear factor of kappa light polypeptide gene enhancer in B-cells 1 (p105) | |
| 39730_at | ABL1 | X16416 | v-abl Abelson murine leukemia viral oncogene homolog 1 | Leukemia, chronic myeloid |
| 38743_f_at | RAF1 | X06409 | v-raf-1 murine leukemia viral oncogene homolog 1 | |
| 36645_at | RELA | L19067 | v-rel reticuloendotheliosis viral oncogene homolog A, nuclear factor of kappa light polypeptide gene enhancer in B-cells 3, p65 (avian) | |
| 41436_at | ZNF198 | AJ224901 | zinc finger protein 198; OMIM Notes: ZNF198 involves T-or B-cell lymphoblastic lymphoma, myeloid hyperplasia, and eosinophilia and evolves toward AML. This multilineage involvement suggests the malignant transformation of primitive hematopoietic stem cell. | Stem-cell leukemia/lymphoma syndrome |
| 40091_at | BCL6 | U00115 | B-cell CLL/lymphoma 6 (Zinc finger protein 51); OMIM Notes: BCL6 is predominantly expressed in the B-cell lineage, especially mature B cells (centrocytes and centroblasts). | Lymphoma, B-cell, Diffuse Large |
| 32776_at | RALB | M35416 | v-ral simian leukemia viral oncogene homolog B (ras related; GTP binding protein) | |
| 32696_at | PBX3 | X59841 | pre-B-cell leukemia transcription factor 3 | |
| 33791_at | DLEU1 | Y15227 | deleted in lymphocytic leukemia, 1 | |
| 34005_at | PIGR | X73079 | polymeric immunoglobulin receptor | /Binds and transports polymeric immunoglobulin |
| 1636_g_at | ABL | U07563 | ABL is the cellular homolog proto-oncogene of Abelson's murine leukemia virus and is associated with the 19:22 chromosomal translocation with the BCR gene in chronic myelogenous and acute lymphoblastic leukemia. | Leukemia, chronic myeloid |
| 1728_at | BMI1 | L13689 | B lymphoma Mo-MLV insertion region (mouse) | /proto-oncogene |
| 2020_at | CCND1 | M73554 | cyclin D1 (PRAD1: parathyroid adenomatosis 1) | Centrocytic lymphoma; Leukemia/lymphoma, B-cell, 1; Multiple myeloma; Parathyroid adenomatosis 1 |
| 1295_at | RELA | L19067 | v-rel reticuloendotheliosis viral oncogene homolog A, nuclear factor of kappa light polypeptide gene enhancer in B-cells 3, p65 (avian) | |

TABLE 14-continued

B-cell/B-cell neoplasms (Seshi, B)

| Systematic | Common | Genbank | Description | Phenotype/Function |
|---|---|---|---|---|
| 1377_at | NFKB1 | M58603 | nuclear factor of kappa light polypeptide gene enhancer in B-cells 1 (p105) | |
| 1461_at | NFKBIA | M69043 | nuclear factor of kappa light polypeptide gene enhancer in B-cells inhibitor, alpha | /IkB-like activity |
| 1389_at | MME | J03779 | membrane metallo-endopeptidase (neutral endopeptidase, enkephalinase, CALLA, CD10) | |
| 35350_at | GALNAC4S-6ST | AB011170 | B cell RAG associated protein | |
| 35992_at | MSC | AF087036 | musculin (activated B-cell factor-1, ABF1); OMIM Notes: Downstream target of B-cell receptor signal transduction pathway. Also expressed in proliferating undifferentiated myeloblasts. | /basic helix-loop-helix transcription factor |
| 34344_at | IKBKAP | AF044195 | inhibitor of kappa light polypeptide gene enhancer in B-cells, kinase complex-associated protein | Dysautonomia, familial |
| 34350_at | RSN | X64838 | restin (Reed-Sternberg cell-expressed intermediate filament-associated protein); Note R-S cell is a form of B-cell. | |
| 36204_at | PTPRF | Y00815 | protein tyrosine phosphatase, receptor type, F; OMIM Notes: Alternative title, Leukocyte antigen-related tyrosine phosphatase (LAR). Both LAR and LCA (CD45) map to chromosome 1. LCA is protein-tyrosine phosphatase, receptor-type C, PTPRC, whereas LAR is PTPRF. | |
| 34391_at | IGBP1 | Y08915 | immunoglobulin (CD79A) binding protein 1. | IGBP1, a marker for early B-cells |
| 1373_at | TCF3 | M31523 | proto-oncogene or transcription factor 3 TCF3 (E2A immunoglobulin enhancer binding factors E12/E47); OMIM Notes: E2A mutant mice will have selective failure to develop B cells, all other hematopoietic cell lineages being intact. The block to B cell development occurs before immunoglobulin D(H)–J(H) rearrangement. | Leukemia, acute lymphoblastic. A homeobox gene contributing the DNA binding domain of the t(1:19) translocation protein in precursor B-cell ALL. |
| 35150_at | TNFRSF5 | X60592 | tumor necrosis factor receptor superfamily, member 5; OMIM notes: Alternative title, B-cell associated molecule CD40; expressed on the surface of all mature B cels, most mature B-cell malignancies and some early B-cell ALL. | Immunodeficiency with hyper-IgM, type 3 |
| 38740_at | ZFP36L1 | X79067 | zinc finger protein 36, C3H type-like 1; OMIM Notes: Alternative title, BERG36 (B-cell early response gene encoding a 36 kD protein). | |
| 37026_at | COPEB | AF001461 | core promoter element binding protein; OMIM Notes: Alternative title, B-cell-derived 1, BCD1. The expression of BCD1 was limited to two tissues, CD19+ B-cells and testis of normal individuals. B-cell maturation is associated with BCD1 expression. | /transcription factor involved in hepatic wound healing |
| 38050_at | BTF | D79986 | Bcl-2-associated transcription factor | |
| 32696_at | PBX3 | X59841 | pre-B-cell leukemia transcription factor 3 | |

TABLE 15

Myeloid cell/myeloid leukemia (Seshi, B)

| Systematic | Common | Genbank | Description | Phenotype/Function |
|---|---|---|---|---|
| 39037_at | MLLT2 | L13773 | myeloid/lymphoid or mixed-lineage leukemia (trithorax homolog, Drosophila); translocated to, 2 | |
| 37486_f_at | MEIS3 | U68385 | Meis1, myeloid ecotropic viral integration site 1 homolog 3 (mouse) | |
| 37685_at | PICALM | U45976 | phosphatidylinositol binding clathrin assembly protein | Leukemia, acute myeloid; Leukemia, acute T-cell lymphoblastic |

TABLE 15-continued

Myeloid cell/myeloid leukemia (Seshi, B)

| Systematic | Common | Genbank | Description | Phenotype/Function |
|---|---|---|---|---|
| 41220_at | MSF | AB023208 | MLL septin-like fusion; a fusion partner gene of MLL | Leukemia, acute myeloid, therapy-related; Ovarian carcinoma |
| 41175_at | CBFB | L20298 | core-binding factor, beta subunit | Myeloid leukemia, acute, M4Eo subtype |
| 943_at | RUNX1 | D43968 | runt-related transcription factor 1 (acute myeloid leukemia 1; aml1 oncogene) | Leukemia, acute myeloid; Platelet disorder, familial, with associated myeloid malignancy |
| 39730_at | ABL1 | X16416 | v-abl Abelson murine leukemia viral oncogene homolog 1 | Leukemia, chronic myeloid |
| 33146_at | MCL1 | L08246 | myeloid cell leukemia sequence 1 (BCL2-related) | |
| 1636_g_at | ABL | U07563 | ABL is the cellular homolog proto-oncogene of Abelson's murine leukemia virus and is associated with the t9:22 chromosomal translocation with the BCR gene in chronic myelogenous and acute lymphoblastic leukemia. | Leukemia, chronic myeloid |
| 277_at | MCL1 | L08246 | myeloid cell leukemia sequence 1 (BCL2-related) | |
| 41388_at | MEIS2 | AF017418 | Meis 1, myeloid ecotropic viral integration site 1 homolog 2 (mouse) | |
| 40189_at | SET | M93651 | SET translocation (myeloid leukemia-associated, M2/M4 AML); SET stands for suppressor of variegation, enhancer of zeste and trithorax. | |
| 38992_at | DEK | X64229 | DEK oncogene (DNA binding) | Leukemia, acute nonlymphocytic |
| 36941_at | AF1Q | U16954 | ALL1-fused gene from chromosome 1q | Leukemia, acute myelomonocytic |

TABLE 16

T cell/NK cell (Seshi, B)

| Systematic | Common | Genbank | Description | Phenotype/Function |
|---|---|---|---|---|
| 37685_at | PICALM | U45976 | phosphatidylinositol binding clathrin assembly protein | Leukemia, acute myeloid; Leukemia, acute T-cell lymphoblastic |
| 498_at | TAX1BP1 | U33821 | Tax1 (human T-cell leukemia virus type I) binding protein 1 | |
| 40822_at | NFATC3 | L41067 | nuclear factor of activated T-cells, cytoplasmic, calcineurin-dependent 3 | |
| 34003_at | CD4 | U47924 | major receptor for HIV-1; member of immunoglobulin supergene family; T cell surface glycoprotein T4 | /T-cell coreceptor; involved in antigen recognition; participant in signal transduction pathway |
| 32602_at | RAP1GDS1 | X63465 | RAP1, GTP-GDP dissociation stimulator 1 | Lymphocytic leukemia, acute T-cell (T-ALL) |
| 35279_at | TAX1BP1 | U33821 | Tax1 (human T-cell leukemia virus type I) binding protein 1 | |
| 34234_f_at | NKTR | AI688640 | natural killer-tumor recognition sequence; OMIM Notes: The protein product of the NKTR gene is present on the surface of LGLs and facilitates their binding to tumor targets. | |
| 39426_at | TCERG1 | AF017789 | transcription elongation regulator 1 (CA150) | /HIV-1 Tat transcriptional coactivator |
| 32602_at | RAP1GDS1 | X63465 | RAP1, GTP-GDP dissociation stimulator 1 | Lymphocytic leukemia, acute T-cell |

TABLE 17

Stromal cells showing expression of genes that are typically affiliated with B-cell progenitors

| Gene | Probe ID | GenBank ID | cMPC | cUSC | sMPC |
|---|---|---|---|---|---|
| CD45 | 40518_at | | Positive in 4/5 samples | Positive in 8/8 samples | Positive in 6/10 samples |
| CD34 | 538_at | | 4/5 | 5/8 | 4/10 |
| CD19 | 1116_at | | 0/5 | 0/8 | 10/10 |
| CD20 | 619_at | | 1/5 | 0/8 | 3/10 |
| CD22 | 38521_at | | 0/5 | 2/8 | 1/10 |
| *CD10 (CALLA) Common acute lymphoblastic leukemia antigen. | 1389_at | | 5/5 | 8/8 | 10/10 |
| *Transcription factor 3 (E2A) Immunoglobulin enhancer binding factors E12/E47 | 1373_at | | 5/5 | 8/8 | 9/10 |
| *CD79A (IGBP1) Immunoglobulin binding protein 1, a marker for early B-cells | 34391_at | | 5/5 | 8/8 | 9/10 |
| *HLA class II, Dr alpha | 37039_at | | 5/5 | 8/8 | 9/10 |
| *HLA class II, Dr beta 1 | 33261_at | | 5/5 | 8/8 | 10/10 |
| *B2M Beta-2 microglobulin | 34644_at | | 5/5 | 8/8 | 10/10 |
| CD2 | 40738_at | | 1/5 | 2/8 | 2/10 |
| CD5 | 32953_at | | 0/5 | 0/8 | 0/10 |
| CD7 | 771_s_at | | 0/5 | 0/8 | 0/10 |
| CD13 | 39385_at | | 5/5 | 8/8 | 0/10 |
| CD33 | 36802_at | | 2/5 | 4/8 | 0/10 |
| CD14 | 36661_at | | 3/5 | 8/8 | 0/10 |

Footnote to Table 17
Genes marked with asterisk (*) have met the criteria for inclusion in stromal cell gene list.

References

Agarwal R, Doren 5, Hicks B, Dunbar C E: Long-term culture of chronic myelogenous leukemia marrow cells on stem cell factor-deficient stroma favors benign progenitors. Blood 85:1306–13 12, 1995

Agarwal, R., Doren, S., Hicks, B. & Dunbar, C. E. (1995) Blood 85, 1306–12.

Ahizadeh A A, Eisen M B, Davis R E, Ma C, Lossos I S, Rosenwald A, Boldrick I C, Sabet H, Iran I, Yu X, Powell 11, Yang L, Marti G~, Moore I, Hudson 1, Lu L, Lewis D B, libshirani R, Sherlock 0, Chan W C, Greiner I C, Weisenburger D D, Armitage 10, Wamke R, Staudt L M, et al.: Distinct types of diffuse large B-cell lymphoma identified by gene expression profiling. Nature 403:503–511., 2000

Alaiya, A. A., Franzen, B., Auer, G. & Linder, S. (2000) Electrophoresis 21, 1210–7.

Alexandrakis M, Coulocheri 5, Xylouri I, Ganotakis E, Ehiakis P, Karkavitsas N, Eliopoulos G D: Elevated serum TN7F-alpha concentrations are predictive of shortened survival in patients with high-risk myelodysplastic syndromes. Haematologia (Budap) 29:13–24, 1998

Alexandrakis, M., Coulochein, S., Xylouri, I., Ganotakis, E., Eliakis, P., Karkavitsas, N. & Eliopoulos, G. D. (1998) Haematologia (Budap) 29, 13–24.

Alon U, Barkai N, Notterman D A, Gish K, Ybarra S, Mack D, Levine A J: Broad patterns of gene expression revealed by clustering analysis of tumor and normal colon tissues probed by ohigonucleotide arrays. Proc Natl Acad Sci USA, 96:6745–6750., 1999

Appel, R. D., Bairoch, A., Sanchez, J. C., Vargas, J. R., Golaz, 0., Pasquali, C. & Hochstrasser, D. F. (1996) Electrophoresis 17, 540–6.

Appel, R. D., Hoogland, C., Bairoch, A. & Hochstrasser, D. F. (1999) in 2-D Proteome Analysis Protocols, ed. Link, A. 3. (Huniana Press, Totowa, N.J.), pp. 411416.

Auerbach R: Patterns of tumor metastasis: organ selectivity in the spread of cancer cells. Lab Invest 58:361–364, 1988

Auerbach, R. (1988) Lab Invest 58, 36 14.

Bennett 3M, Catovsky D, Daniel M I, Flandrin G, Galton D A, Gralnick H R. Sultan C: Proposals for the classification of the myelodysplastic syndromes. Br 1 Haematol 5 1:189–199, 1982

Bhatia R, McGlave P B, Dewald G W, Blazar B R, Verfaillie C M: Abnormal function of the bone marrow microenvironment in chronic myelogenous leukemia: role of malignant stromal macrophages. Blood 85:3636–3645., 1995

Bjornson C R, Rietze R L, Reynolds B A, Magli M C, Vescovi A L: Turning brain into blood: a hematopoietic fate adopted by adult neural stem cells in vivo [see comments]. Science 283:534–537, 1999

Budak-Alpdogan I, Alpdogan 0, Akoglu I: Morphological and functional characteristics of short-term and long-term bone marrow cultures in chronic myelogenous leukemia. Am 1 Hematol 62:212–220., 1999

Bustin S A: Absolute quantification of mRNA using real-time reverse transcription polymerase chain reaction assays. I Mol Endocrinol 25:169–193., 2000

Celis J E, Kruhoffer M, Gromova I, Frederilcsen C, Ostergaard M, Thykjaer I, Gromov P, Yu 3, Palsdottir H, Magnusson N, Orntoft I F: Gene expression profiling: monitoring transcription and translation products using DNA microarrays and proteomics. FEBS Lett 480:2–16, 2000

Celis, 3. E., Kruhoffer, M., Gromova, 1., Frederiksen, C., Ostergaard, M., Thykjaer, T., Gromov, P., Yu, 3., Palsdottir, H., Magnusson, N. & Orntoft, I. F. (2000) *FEBSLett* 480, 2–16.

Celis, J. E. & Gromov, P. (1999) *Curr Opin Biotechnol* 10, 16–21.

Chambers, G., Lawrie, L., Cash, P. fray, G. I. (2000) *JPathol* 192, 280–288.

Chen D, Chang R E, Huang Y L: Breast cancer diagnosis using self-organizing map for sonography. Ultrasound Med Biol 26:405–411, 2000

Clark E A, Golub I R, Lander E S, Hynes R0: Genomic analysis of metastasis reveals an essential role for RhoC. Nature 406:532–535., 2000

Cordwell, S. 3., Nouwens, A. S., Verrills, N. M., McPherson, 3. C., Hams, P. G., van Dyk, D. D. & Walsh, B. 3. (1999) *Electrophoresis* 20, 3580–8.

Cordwell, S. J., Nouwens, A. S., Verrills, N. M., Basseal, D. J. & Walsh, B. J. (2000) *Electrophoresis* 21,1094–103.

Crino P B, Trojanowski J Q, Dichter M A, Eberwine 1: Embryonic neuronal markers in tuberous sclerosis: singlecell molecular pathology. Proc Natl Acad Sci USA 93:14152–14157., 1996

Damiano I S, Cress A E, Hazlehurst L A, Shtil A A, Dalton W S: Cell adhesion mediated drug resistance (CAMDR): role of integrins and resistance to apoptosis in human myeloma cell lines. Blood 93:1658–1667, 1999

Damiano I S, Dalton W S: Integrin-mediated drug resistance in multiple myeloma. Leuk Lymphoma 38:71–81, 2000

Damiano, 3. S. & Dalton, W. S. (2000) *LeukLymphoma* 38, 71–81.

Damiano, 3. S., Cress, A. E., Hazlehurst, L. A., Shtil, A. A. & Dalton, W. S. (1999) *Blood* 93, 1658–67.

Deeg H I, Beckham C, Loken M R, Bryant E, Lesnikova M, Shulman H M, Gooley I: Negative regulators of hemopoiesis and stroma function in patients with myelodysplastic syndrome. Leuk Lymphoma 37:405–414, 2000

Deeg, H. J., Beckham, C., Loken, M. R., Bryant, E., Lesnikova, M., Shuhnan, H. M. & Gooley, 1. (2000) *Leuk Lymphoma* 37, 405–14.

Dexter T M, Allen I D, Lajtha L G: Conditions controlling the proliferation of haemopoietic stem cells in vitro. 1 Cell Physiol 91:335–344, 1977

Dexter, T. M., Allen, T. D. & Lajtha, L. G. (1977) *J Cell Physiol* 91, 335–44.

Diana C, Dominici M, Lanza F, Punturieri M, Pauhi 5, Tieghi A, Dabusti M, Scapoli 0, 0. C: Impairment of stromal cells compartment in hypoplastic myelodysplastic syndromes (Abstract). Blood 96:357a, 2000

Eaves A C, Eaves Ci: Maintenance and proliferation control of primitive hemopoietic progenitors in long-term cultures of human marrow cells. Blood Cells 14:355–368, 1988

Eaves, A. C. & Eaves, C. J. (1988) *Blood Cells* 14, 355–68.

Eglitis M A, Mezey E: Hematopoietic cells differentiate into both microglia and macroghia in the brains of adult mice. Proc Natl Acad Sci USA 94:4080–4085, 1997

Eisen M B, Spellman P T, Brown P0, Botstein D: Cluster analysis and display of genome-wide expression patterns. Proc Natl Acad Sci USA 95:14863–14868, 1998

Emmert-Buck M R. Bonner R E, Smith P D, Chuaqui R E, Zhuang Z, Goldstein S R. Weiss R A, Liotta L A: Laser capture nticrodissection. Science 274:998–1001., 1996

Felley-Bosco, E., Demalte, I., Barcelo, S., Sanchez, J. C., Hochstrasser, D. F., Schlegel, W. & Reymond, M. A. (1999) *Electrophoresis*20, 3508–13.

Finedenstein, A. J., Gorskaja, J. F. & Kulagina, N. N. (1976) *Exp Hematol* 4, 267–74.

Franitza, S., Hershkoviz, R., Kam, N., Lichtenstein, N., Vaday, G. G., Alon, R. & Lider, 0. (2000) *JImmunol* 165, 2738–47.

Friedenstein A J, Gorskaja iF, Kulagina N N: Fibroblast precursors in normal and irradiated mouse hematopoietic organs. Exp Hematol 4:267–274, 1976

Gartner 5, Kaplan H S: Long-term culture of human bone marrow cells. Proc Natl Acad Sci USA 77:47564759, 1980

Gartner, S. & Kaplan, H. S. (1980) *Proc NatlAcad Sci USA* 77, 4756–9.

Gazitt, Y., Freytes, C. 0., Callander, N., Tsai, I. W., Alsina, M., Anderson, 3., Holle, L., Cruz, 3., Devore, P., McGrath, M., West, G., Alvarez, R. & Montgomery, W. (1999) *JHematother* 8, 173–83.

Gianni, A. M., Siena, S., Bregni, M., Tarella, C., Stern, A. C., Pileri, A. & Bonadonna, G. (1989) Lancet2, 580–5.

Godovac-Zimmermann, 3., Soskic, V., Poznanovic, S. & Brianza, F. (1999) *Electrophoresis* 20, 952–6 1.

Golub T R, Slonim D K, lamayo P, Huard C, Gaasenbeek M, Mesirov I P, Coller H, Loh M L, Downing J R. Cahigiuri M A, Bloomfield C D, Lander E S: Molecular classification of cancer: class discovery and class prediction by gene expression monitoring. Science 286:531–537., 1999

Gorg, A., Obermaier, C., Boguth, G., Harder, A., Scheibe, B., Wildgruber, R. & Weiss, W. (2000) *Electrophoresis* 21, 1037–1053

Greenberg P, Anderson 3, de Witte I, Estey E, Fenaux P, Gupta P, Hamblin I, Hellstrom-Lindberg E, List A, Mufti 0, Neuwirtova, Ohyashiki K, Oscier D, Sanz 0, Sanz M, Willnian C: Problematic WHO reclassification of myelodysplastic syndromes. Members of the International MDS Study Group. I Chin Oncol 18:3447–3452., 2000

Greenberger J S: Sensitivity of corticosteroid-dependent insulin-resistant lipogenesis in marrow preadipocytes of obese-diabetic (db/db) mice. Nature 275:752–754, 1978

Greenberger, J. S. (1978) *Nature* 275, 7524.

Gurney K: Self-organization: An Introduction to Neural Netv~orks (ed First). London, UCL Press Limited, 1997, p 115–146

Harris N L, Jaffe E S, Diebold 1, Flandrin G, Muller-Hermelink H K, Vardiman 1, Lister T A, Blooniefield C D: World Health Organization classification of neoplastic diseases of the hematopoietic and lymphoid tissues: report of the Clinical Advisory Committee meeting-Ailie House, Virginia, Nov. 1997. 3Chin Oncol 17:3835–3849, 1999

Hidai C, Zupancic I, Penta K, Mikhail A, Kawana M, Quertermous E E, Aoka Y, Fukagawa M, Matsui Y, Platika D, Auerbach R, Hogan B L, Snodgrass R, Quertermous I: Cloning and characterization of developmental endothehial locus1: an embryonic endothehial cell protein that binds the alphavbeta3 integrin receptor. Genes Dev 12:21–33., 1998

Hofmann W-K, deVos 5, Tsukasaki K, Wachsman W, Pinkus O S, Said 1W, Koeffler H P: Altered apoptosis pathways in mantle cell lymphoma detected by ohigonucleotide microarray (Abstract). Blood 96:468a, 2000

Hoving, S., Voshol, H. & van Oostrum, J. (2000) *Electrophoresis* 21, 2617–21.

In L, Thompson C A, Qian X, Kuecker S I, Kuhig E, Lloyd R V: Analysis of anterior pituitary hormone mRNA expression in immunophenotypically characterized single cells after laser capture microdissection. Lab Invest 79:511–512., 1999

Jensen, 0. N., Wilm, M., Shevchenko, A. & Mann, M. (1999) in *2-D Proteome Analysis Protocols*, ed. Link, A. J. (Humana Press, Totowa, N.J.), pp. 57 1–588.

Johnson R A, Wichern D W: Clustering: Applied Multivariate Statistical Analysis (ed Third). Englewood Cliffs, Prentice Hall, 1992, p 573–627

Kacharmina J E, Crino P B, Eberwine 3: Preparation of cDNA from single cells and subcellular regions. Methods Enzymol 303:3–18., 1999

Klose, J. (1975) *Humangenetik* 26, 23143.

Kohonen I: Self-Organizing Maps (ed Second). New York, Springer-Verlag, 1997

Lagneaux L, Delforge A, Bron D, De Bruyn C, Stryckmans P: Chronic lymphocytic leukemic B cells but not normal B cells are rescued from apoptosis by contact with normal bone marrow stromal cells. Blood 9 1:2387–2396, 1998

Lagneaux L, Delforge A, Dc Bruyn C, Bernier M, Bron D: Adhesion to bone marrow stroma inhibits apoptosis of chronic lymphocytic leukemia cells. Leuk Lymphoma 35:445–453, 1999

Lagneaux, L., Delforge, A., Bron, D., De Bruyn, C. & Stsyckmans, P. (1998) *Blood* 91, 23 87–96.

Lagneaux, L., Delforge, A., Dc Bruyn, C., Bernier, M. & Bron, D. (1999) *LeukLymphoma* 35, 445–53:

Le Bousse-Kerdiles M C, Martyre M C: Dual implication of fibrogenic cytokines in the pathogenesis of fibrosis and myeloprohiferation in myeloid metaplasia with myelofibrosis. Ann Hematol 78:437–444, 1999

Le Bousse-Kerdiles, M. C. & Martyre, M. C. (1999) *Ann Hematol* 78, 43744.

Lichtman M A: Myelodysplasia or Myeloneoplasia: Thoughts on the Nosology of Clonal Myeloid Diseases. Blood Cells Mol Dis 26:572–58 1, 2000

Lichtman M A: The ultrastructure of the hemopoietic environment of the marrow: a review. Exp Hematol 9:391–410, 1981

Lockhart D J, Winzeler E A: Genomics, gene expression and DNA arrays. Nature 405:827–836., 2000

Lokhorst H M, Lamme I, de Smet M, Klein 5, de Weger R A, van Oers R, Bloem A C: Primary tumor cells of myeloma patients induce interleukin-6 secretion in long-term bone marrow cultures. Blood 84:2269–2277, 1994

Lokhorst, H. M., Lamme, T., de Smet, M., Klein, S., de Weger, R. A., van Oers, R. & Bloem, A. C. (1994) *Blood* 84, 2269–2277

Lopez, M. F. (2000) *Electrophoresis* 21, 1082–93.

Luo L, Salunga R C, Guc ctner A, Joy K C, Galindo J E, Xiao H, RoL ~i, Wan I S, Jackson M R, Erlander M G: Gene expression profiles of laser-captured adjacent neuronal subtypes. Nat Med 5:117–122., 1999

Manabe A, Coustan-Smith E, Behm F G, Raimondi S C, Campana D: Bone marrow-derived stromal cells prevent apoptotic cell death in B-lineage acute lymphoblastic leukemia. Blood 79:2370–2377, 1992

Manabe, A., Coustan-Smith, E., Behm, F. G., Raimondi, S. C. & Campana, D. (1992) *Blood* 79Q 2370–7.

Marini F, Zompetta C, Wang R-Y, Studeny M, Zoltick P, Wilson I, Andreeff M: Mesenchymal stem cells (MSC) from patients with chronic myelogenous leukemia (CML) patients can be transduced with common gene transfer vectors at high efficiency, and are genotypically normal (Abstract). Blood 96:740a, 2000

Minguell 31, Martinez 1: Growth pattern and function of bone marrow fibroblasts from normal and acute lymphoblastic leukemia patients. Exp Hematol 11:522–526., 1983

Miyazato A, Ohmine K, Ueda M, Ozawa K, Mano H: Identification of myelodysplastic syndrome-specific genes by DNA microarray analysis with "blast bank" samples (Abstract). Blood 96:544a, 2000

Molloy, M. P., Herbert, B. R., Walsh, B. J., Tyler, M. I., Traini, M., Sanchez, J. C., Hochstrasser, D. F., Williams, K. L. & Gooley, A. A. (1998) *Electrophoresis* 19, 837–44.

Mundle S D, Ahi A, Cartlidge I D, Reza 5, Alvi 5, Showel M M, Mativi B Y, Shetty V T, Venugopal P, Gregory S A, Raza A: Evidence for involvement of tumor necrosis factor-alpha in apoptotic death of bone marrow cells in myelodysplastic syndromes. Am 3 Hematol 60:3647, 1999

Mundle S D, Reza 5,Ahi A, Mativi Y, Shetty V, Venugopal P, Gregory S A, Raza A: Correlation of tumor necrosis factor alpha (TNF alpha) with high Caspase 3-like activity in myelodysplastic syndromes. Cancer Lett 140:201–207, 1999

Mundle, S. D., Au, A., Cartlidge, J. D., Reza, S., Alvi, S., Showel, M. M., Mativi, B. Y., Shetty, V. T., Venugopal, P., Gregory, S. A. & Raza, A. (1999) *Am JHematol* 60, 3647.

Mundle, S. D., Reza, S., Ali, A., Mativi, Y., Shetty, V., Venugopal, P., Gregory, S. A. & Raza, A. (1 999) *Cancer Lett* 140, 201–7.

Nagao I, Yamauchi K, Komatsuda M, Noguchi K, Shimizu M, Yonekura 5, Nozaki H: Inhibition of human bone marrow fibroblast colony formation by leukemic cells. Blood 62:1261–1265., 1983

Nagao I, Yamauchi K, Komatsuda M: Serial in vitro bone marrow fibroblast culture in human leukemia. Blood 61:589–592., 1983

O'Dell DM, McIntosh 1 K, Eberwine J H: Single-cell molecular biology: implications for the diagnosis and treatment of neurological disease. Arch Neurol 56:1453–1456., 1999

O'Farrell, P. H. (1 975) *JBiol Chem* 250, 4007–21.

Paget 5: The distribution of secondary growths in cancer of the breast. Lancet i:57I, 1889

Paget, S. (1 889) *Lancet* 1, 571.

Peled A, Lee B C, Steinberg D, Toledo 3, Aracil M, Zipori D: Interactions between leukemia cells and bone marrow stromal cells: stroma-supported growth vs. serum dependence and the roles of TGF-beta and M-CSF. Exp Hematoh 24:728–737., 1996

Penta K, Varner J A, Liaw L, Hidai C, Schatzrnan R, Quertermous T: Dell induces integrin signaling and angiogenesis by ligation of alphaVbeta3. I Biol Chem 274: 11101 –11109., 1999

Perou C M, Jeffrey S S, van de Run M, Rees C A, Eisen M B, Ross D I, Pergamenschikov A, Williams C E, Thu S X, Lee I C, Lashkari D, Shalon D, Brown P O, Botstein D: Distinctive gene expression patterns in human mammary epithehial cells and breast cancers. Proc Nati Acad Sci USA 96:9212–9217., 1999

Phillips E J L, Ernst R E, Brunk B, Ivanova N, Mahan M A, Deanehan 1K, Moore K A, Overton G C, Lemischka I R:

Pittenger M E, Mackay A M, Beck S C, Jaiswal R K, Douglas R, Mosca I D, Moorman M A, Simonetti D W, Craig 5, Marshak D R: Multilineage potential of adult human mesenchymal stem cells. Science 284:143–147, 1999

Pittenger, M. F., Mackay, A. M., Beck, S. C., Jaiswal, R. K., Douglas, R., Mosca, J. D., Moorman, M. A., Simonetti, D. W., Craig, S. & Marshak, D. R. (1999) *Science* 284, 143–7.

Querol, S., Cancelas, 3. A., Amat, L., Capniany, G. & Garcia, 3. (1999) *Haematologica* 84, 493–8.

Raza A, Mundle 5, Shetty V, Alvi 5, Chopra H, Span L, Parcharidou A, Dar 5, Venugopal P, Borok R, Gezer 5, Showel 3, Loew 3, Robin E, Rifldn 5, Alston D, Hernandez B, Shah R, Kaizer H, Gregory 5: Novel insights into the biology of myelodysplastic syndromes: excessive apoptosis and the role of cytokines. Intl Hematol 63:265–278, 1996

Raza, A., Mundle, S., Shetty~V., Alvi, S., Chopra, H., Span, L., Parcharidou, A., Dar, S., Venugopal, P., Borok, R., Gezer, S., Showel, J., Loew, J., Robin, E., Rifkin, S., Alston, D., Hemandez, B., Shah, R., Kaizer, H. & Gregory, S. (1996) *mt J Hematol* 63, 265–78.

Record, M., Bes, J. C., Chap, H. & Douste-Bla.zy, L. (1982) *Biochim Biophys Acta* 688, 57–65.

Reilly I T: Idiopathic myelofibrosis: pathogenesis, natural history and management. Blood Rev 11:233–242, 1997

Reilly, 3. T. (1997)*Blood Rev* 11,233–42.

Roberts I A, McMullin M E: A practical miniature long-term bone marrow culture system for investigating early myelodysplasia. Leuk Res 16:737–741, 1992

Rowley, S. D. (2000) in *HEMATOLOGY: Basic Principles and Practice*, eds. Hoffman, R., Benz, 3., E. J., Shattil, S. 3., Furie, B., Cohen, H. 3., Silberstein, L. E. & McGlave, P. (Churchill Livingstone, Pa.), pp. 1642–1658.

Santos-Alvarez, J., Goberna, R. & Sanchez-Margalet, V. (1999) *Cell Immunol* 194, 6–11.

Sawada K, Sato N, Koike I: Inhibition of GM-CSF production by recombinant human interleukin-4: negative regulator of hematopoiesis. Leuk Lymphoma 19:33–42, 1995

Sawada, K., Sato, N. & Koike, T. (1995) *Leuk Lymphoma* 19, 3342.

Sesbi, B. (1995) *Blood* 86, 309a.

Seshi B, Kumar 5, Sellers D: Human bone marrow stromal cell: coexpression of markers specific for multiple mesenchymal cell lineages. Blood Cells Mol Dis 26:234–246, 2000

Seshi B: Cell adhesion to proteins separated by lithium dodecyl sulfate-polyacrylamide gel electrophoresis and blotted onto a polyvinylidene difluoride membrane: a new cell-blotting technique. I Immunol Methods 176:185–201, 1994

Seshi B: Discovery of novel hematopoietic cell adhesion molecules from human bone marrow stromal cell membrane protein extracts by a new cell-blotting technique. Blood 83:2399–2409, 1994

Seshi B: Patterns of progenitor cell adhesion to novel bone marrow stromal CAMs using 2-D cell blotting demonstrate complex adhesive interactions (Abstract). Blood 86:309a, 1995

Seshi B: The dual recognition systems of I lymphocytes: a model. I Theor Biol 99:827–830., 1982

Seshi, B. (1994) *Blood* 83, 2399–409.

Seshi, B. (1994)*JImmunol Methods* 176, 185–201.

Seshi, B., Kumar, S. & Sellers, D. (2000) *Blood Cells Mol Dis* 26, 234–246.

Shain K I L T, Landowski T H, Dalton W S: The tumor microenvironment as a determinant of cancer cell survival: a possible mechanism for de novo drug resistance. Curr Opin Oncol 12:557–563., 2000

Sherlock 0: Analysis of large-scale gene expression data. Curr Opin Immunol 12:20 1–205, 2000

Shevchenko, A., Wilm, M., Vorm, 0. & Mann, M. (1996) *Anal Chem* 68, 850–8.

Silva I P: Software Review: GeneSpring 3.1: HMS Beagle: The BioMedNet Magazine (Issue Jul., 7, 2000), 2000, p http://news.bmn.com,'hmsbeagle/82/reviews/sreview Simmons P I, Przepio Thomas E D, Torok-Storb B: Host ori~marrow stromal cells following allogeneic bone marrow transplantation. Nature 328:429432, 1987

Soskic, V., Gorlach, M., Poznanovic, S., Boehmer, F. D. & Godovac-Zimmermann, J. (1999) *Biochemistry* 38, 1757–64.

Tamayo P, Slonim D, Mesirov I, Zhu Q, Kitareewan 5, Dmitrovsky E, Lander E S, Golub T R: Interpreting patterns of gene expression with self-organizing maps: methods and application to hematopoietic differentiation. Proc Nath Acad Sci USA 96:2907–29 12, 1999

Tempst, P., Erdjument-Bromage, H., Posewitz, M. C., Geromanos, S., Freckleton, G., Grewal, A., Lacomis, L., Lui, M. & Philip, J. (2000) in *Mass Spectrometty in Biology & Medicine*, eds. Burlingame, A. L., Can, S. A. & Baldwin, M. A. (Huxnana Press, Totowa, N.J.), pp. 121–142.

The genetic program of hematopoietic stem cells. Science 288:1635–1640., 2000

Thiele D L, Kurosaka M, Lipsky P E: Phenotype of the accessory cell necessary for mitogen-stimulated I and B cell responses in human peripheral blood: delineation by its sensitivity to the lysosomotropic agent, L-leucine methyl ester. I]Immunol 13 1:2282–2290, 1983

Thiele, D. L., Kurosaka, M. & Lipsky, P. E. (1983) *JImmunol* 131, 2282–90.

Thomas, T., Gori, F., Khosla, S., Jensen, M. D., Burguera, B. & Riggs, B. L. (1999) *Endocrinology* 140, 1630–8.

Torok-Storb B: Cellular interactions. Blood 72:373–385, 1988

Torok-Storb, B. (1988) *Blood* 72, 373–85.

Unlu, M., Morgan, M. E. & Minden, J. S. (1997) *Electrophoresis* 18, 2071–7.

Verfailhie C M: Anatomy and physiology of hematopoiesis, in Hoffman R, Benz 1, E. J., Shattil Si, Furie B, Cohen Hi, Silberstein L E, McGlave P (eds): HEMATOLOGY: asic Principles and Practice (ed 3rd). New York, Churchill Livingstone, 2000, p 139–154

Verfaillie, C. M. (2000) in *HEMATOLOGY Basic Principles and Practice*, eds. Hoffman, R., Benz, J., E. J., Shattil, S. J., Furie, B., Cohen, H. J., Silberstein, L. E. & McGlave, P. (Chuschill Livingstone, N.Y.), pp. 139–154.

Wallace S R, Oken M M, Ness By, Maselhis A M: Abnormalities of bone marrow mesenchymal stem cells in multiple myeloma (Abstract). Blood 94:547a, 1999

Wallace, S. R., Oken, M. M., Ness, B. V. & Masellis, A. M. (1999) *Blood*94, 547a.

Whetton, A. D. & Spooncer, E. (1998) *Curr Opin Cell Biol*10, 721–6.

Williams, K. L. & Hochstrasser, D. F. (1997) in *Proteome Research: New frontiers in Functional Genomics*, eds. Wilikins, M. R., Williams, K. L., Appel, R. D. & Hochstrasser, D. F. (Springer, N.Y.), pp. 1–12.

Willman C L: Acute leukemias: a paradigm for the integration of new technologies in diagnosis and classification. Mod Pathol 12:218–228., 1999

Wilmut I, Schnieke A E, McWhir 1, Kind A J, Campbell K H: Viable offspring derived from fetal and adult mammalian cells [see comments] [published erratum appears in Nature 1997 Mar. 13;386(6621):200]. Nature 385:810–813, 1997

Wooster R: Cancer classification with DNA microarrays is less more? Trends Genet 16:327–329., 2000

Yanagida, M., Miura, Y., Yagasaki, K., Taoka, M., Isobe, I. & Takahashi, N. (2000) *Electrophoresis* 21, 1890–8.

Young R A: Biomedical discovery with DNA arrays. Cell 102:9–15., 2000

What is claimed is:

1. A method for diagnosing a leukemic disease state in a patient, the method comprising:
   (a) providing a gene expression profile of a patient's bone marrow derived isolated pluri-differentiated mesenchymal progenitor cell of unknown state, wherein the isolated pluri-differentiated mesenchymal progenitor cell simultaneously expresses a plurality of genes at the protein level that are markers for multiple cell lineages, wherein the multiple cell lineages comprise at least four different mesenchymal cell lineages, and wherein each of the markers is specific for a single cell lineage; and
   (b) comparing the patient's gene expression profile to a reference gene expression profile obtained from a normal bone marrow derived pluri-differentiated mesenchymal progenitor cell, wherein the reference gene expression profile comprises an expression value of a target gene selected from the group consisting of human mRNA for cartilage specific proteoglycan, *Homo sapiens* tyrosine phosphatase, X-linked mental retardation candidate gene, human interleukin-10 receptor mRNA, H-interferon inducible peptide (6-16), interferon-inducible 56 kD protein, human insulin-like growth factor binding protein 5 (IGFBP5), winged helix transcription factor, interferon gamma, human mRNA for zinc finger protein (clone 431), apolipoprotein D precursor, p53 tumor antigen, *Homo sapiens* Kueppel family zinc finger protein, major group rhinovirus receptor precursor, ICE like protease, caspase-10/b, human transcription factor SIM2, CMP-N-acetylneuraminic acid hydroxylase, *Homo sapiens* cDNA clone DKFZp586G0421 (symptom: hute 1), human mRNA for histone H1x, putative monocarboxylate transporter *Homo sapiens* gene for LD78 alpha precursor, wg82b12.x1 Soares *Homo sapiens* cDNA clone, human atrial natriuretic peptide clearance receptor (ANP C-receptor), human 71 kDa 2'5' oligoadenylate synthetase (p69 2-5A synthetase), *Homo sapiens* hMmTRA1b, human GOS2 protein gene, preproenkephalin, human guanylate binding protein isoform I (GBP-2), human gene for hepatitis C associated microtubular aggregate protein p44, GS3686, human monoamine oxidase B (MAOB), insulin-like growth factor II precursor, cDNA DKFZp434A202, beta-tropomyosin, *Homo sapiens* clone 24659, human DNA helicase Q1, OSF, ym22b12.r1, Soares infant brain 1NIB *Homo sapiens* cDNA clone, human mRNA for pre-mRNA splicing factor SRp20, human golgi alpha-mannosidasell, OSF-2os, *Homo sapiens* proline synthetase, hk02952 cDNA clone for KIAA0683, wi24g10.x1 *Homo sapiens*, Lysosomal enzyme deficient in Sanfilippo B syndrome, CTP synthetase (AA 1-591), human 5'-terminal region of UMK, *Homo sapiens* chemokine exodus-1, human GPI-H, *Homo sapiens* RAMP1, transforming growth factor-beta-2 precursor, and *Homo sapiens* KIAA0763 protein, wherein differential expression of the target gene is indicative of a leukemic disease state, and wherein the leukemic disease state is selected from the group consisting of acute myeloid leukemia (AML), chronic myeloid leukemia (CML), and multiple myeloma (MM).

2. The method of claim 1, wherein the reference gene expression profile is contained within a database.

3. The method of claim 1, wherein said comparing is carried out using a computer algorithm.

4. The method of claim 1, wherein said method further comprises isolating the bone marrow derived isolated pluri-differentiated mesenchymal progenitor cell of unknown state from the patient.

5. The method of claim 1, wherein said method further comprises preparing the patient's gene expression profile.

6. The method of claim 1, wherein said method further comprises:
   (c) providing a gene expression profile of a bone marrow derived isolated pluri-differentiated mesenchymal progenitor cell from the patient after the patient has undergone a treatment regimen for a leukemic disease state; and
   (d) comparing the post-treatment patient gene expression profile to the reference gene expression profile, to monitor the patient's response to the treatment regimen.

7. The method of claim 1, wherein said method further comprises:
   (c) providing a leukemic disease state diagnosis to the patient.

8. The method of claim 1, wherein the bone marrow derived isolated pluri-differentiated mesenchymal progenitor cell of unknown state comprises a single cell.

9. The method of claim 1, wherein the patient's bone marrow derived isolated pluri-differentiated mesenchymal progenitor cell of unknown state comprises a plurality of cells.

10. The method of claim 1, wherein the patient's isolated pluri-differentiated mesenchymal progenitor cells have been obtained by providing a cell culture preparation by the Dexter method, treating the cells of the cell culture preparation to obtain a cell suspension, removing macrophages from the cell suspension, fractionating the remaining cells, and collecting the fraction of cells containing the normal state pluri-differentiated mesenchymal progenitor cells.

11. The method of claim 1, wherein the at least four different mesenchymal cell lineages comprise adipocyte, osteoblast, fibroblast, and muscle cell.

12. The method of claim 1, wherein the markers specific for a single cell lineage are selected from the group consisting of Nile Red, Oil Red O, adipsin, alkaline phosphatase, cadherin-11, chondroitin sulfate, collagen type I, decorin, fibronectin, prolyl-4-hydroxylase, actin, caldesmon, and transgelin.

13. The method of claim 1, wherein the target gene is human mRNA for cartilage specific proteoglycan, and wherein down-regulation of the target gene is indicative of a leukemic disease state.

14. The method of claim 1, wherein the target gene is *Homo sapiens* tyrosine phosphatase, and wherein down-regulation of the target gene is indicative of a leukemic disease state.

15. The method of claim 1, wherein the target gene is X-linked mental retardation candidate gene, and wherein down-regulation of the target gene is indicative of a leukemic disease state.

16. The method of claim 1, wherein the target gene is human interleukin-10 receptor mRNA, and wherein down-regulation of the target gene is indicative of a leukemic disease state.

17. The method of claim 1, wherein the target gene is H-interferon inducible peptide (6-16), and wherein down-regulation of the target gene is indicative of a leukemic disease state.

18. The method of claim 1, wherein the target gene is interferon-inducible 56 kD protein, and wherein down-regulation of the target gene is indicative of a leukemic disease state.

19. The method of claim 1, wherein the target gene is insulin-like growth factor binding protein 5, and wherein down-regulation of the target gene is indicative of a leukemic disease state.

20. The method of claim 1, wherein the target gene is winged helix transcription factor, and wherein down-regulation of the target gene is indicative of a leukemic disease state.

21. The method of claim 1, wherein the target gene is interferon-gamma, and wherein up-regulation of the target gene is indicative of a leukemic disease state.

22. The method of claim 1, wherein the target gene is human mRNA for zinc finger protein (clone 431), and wherein up-regulation of the target gene is indicative of a leukemic disease state.

23. The method of claim 1, wherein the target gene is apolipoprotein D precursor, and wherein up-regulation of the target gene is indicative of a leukemic disease state.

24. The method of claim 1, wherein the target gene is p53 tumor antigen, and wherein up-regulation of the target gene is indicative of a leukemic disease state.

25. The method of claim 1, wherein the target gene is *Homo sapiens* Kueppel family zinc finger protein, and wherein up-regulation of the target gene is indicative of a leukemic disease state.

26. The method of claim 1, wherein the target gene is major group rhinovirus receptor precursor, and wherein up-regulation of the target gene is indicative of a leukemic disease state.

27. The method of claim 1, wherein the target gene is ICE like protease, and wherein up-regulation of the target gene is indicative of a leukemic disease state.

28. The method of claim 1, wherein the target gene is caspase-10/b and wherein up-regulation of the target gene is indicative of a leukemic disease state.

29. The method of claim 1, wherein the target gene is human transcription factor SIM2, and wherein up-regulation of the target gene is indicative of a leukemic disease state.

30. The method of claim 1, wherein the reference gene expression profile comprises expression values of human mRNA for cartilage specific proteoglycan, *Homo sapiens* tyrosine phosphatase, X-linked mental retardation candidate gene, human interleukin-10 receptor mRNA, H-interferon inducible peptide (6-16), interferon-inducible 56 kD protein, insulin-like growth factor binding protein 5, winged helix transcription factor, interferon gamma, human mRNA zinc finger protein (clone 431), apolipoprotein D precursor, p53 tumor antigen, *Homo sapiens* Kueppel family zinc finger protein, major group rhinovirus receptor precursor, ICE like protease, caspase-10/b, and human transcription factor SIM2.

31. The method of claim 1, wherein the target gene is CMP-N-acetylneuraminic acid hydroxylase, and wherein down-regulation of the target gene is indicative of a leukemic disease state.

32. The method of claim 1, wherein the target gene is *Homo sapiens* cDNA clone DKFZp586G0421 (symptom: hute 1), and wherein down-regulation of the target gene is indicative of a leukemic disease state.

33. The method of claim 1, wherein the target gene is Human mRNA for histone H1x, and wherein down-regulation of the target gene is indicative of a leukemic disease state.

34. The method of claim 1, wherein the target gene is putative monocarboxylate transporter *Homo sapiens* gene for LD78 alpha precursor, and wherein down-regulation of the target gene is indicative of a leukemic disease state.

35. The method of claim 1, wherein the target gene is wg82b12.x1 Soares *Homo sapiens* cDNA clone, and wherein down-regulation of the target gene is indicative of a leukemic disease state.

36. The method of claim 1, wherein the target gene is human atrial natriuretic peptide clearance receptor (ANP C-receptor), and wherein down-regulation of the target gene is indicative of a leukemic disease state.

37. The method of claim 1, wherein the target gene is human 71 kDa 2'5' oligoadenylate synthetase (p69 2-5A synthetase), and wherein down-regulation of the target gene is indicative of a leukemic disease state.

38. The method of claim 1, wherein the target gene is *Homo sapiens* hMmTRA1b, and wherein down-regulation of the target gene is indicative of a leukemic disease state.

39. The method of claim 1, wherein the target gene is human GOS2 protein gene, and wherein down-regulation of the target gene is indicative of a leukemic disease state.

40. The method of claim 1, wherein the target gene is preproenkephalin, and wherein down-regulation of the target gene is indicative of a leukemic disease state.

41. The method of claim 1, wherein the target gene is human guanylate binding protein isoform I (GBP-2), and wherein down-regulation of the target gene is indicative of a leukemic disease state.

42. The method of claim 1, wherein the target gene is human gene for hepatitis C associated microtubular aggregate protein p44, and wherein down-regulation of the target gene is indicative of a leukemic disease state.

43. The method of claim 1, wherein the target gene is GS3686, and wherein down-regulation of the target gene is indicative of a leukemic disease state.

44. The method of claim 1, wherein the target gene is human monoamine oxidase B (MAOB), and wherein down-regulation of the target gene is indicative of a leukemic disease state.

45. The method of claim 1, wherein the target gene is insulin-like growth factor II precursor, and wherein down-regulation of the target gene is indicative of a leukemic disease state.

46. The method of claim 1, wherein the target gene is cDNA DKFZp434A202, and wherein down-regulation of the target gene is indicative of a leukemic disease state.

47. The method of claim 1, wherein the target gene is beta-tropomyosin, and wherein up-regulation of the target gene is indicative of a leukemic disease state.

48. The method of claim 1, wherein the target gene is *Homo sapiens* clone 24659, and wherein up-regulation of the target gene is indicative of a leukemic disease state.

49. The method of claim 1, wherein the target gene is human DNA helicase Q1, and wherein up-regulation of the target gene is indicative of a leukemic disease state.

50. The method of claim 1, wherein the target gene is OSF, and wherein up-regulation of the target gene is indicative of a leukemic disease state.

51. The method of claim 1, wherein the target gene is ym22b12.r1 Soares infant brain 1NIB *homo sapiens* cDNA clone, and wherein up-regulation of the target gene is indicative of a leukemic disease state.

52. The method of claim 1, wherein the target gene is human mRNA for pre-mRNA splicing factor SRp20, and wherein up-regulation of the target gene is indicative of a leukemic disease state.

53. The method of claim 1, wherein the target gene is human golgi alpha-mannosidaseII, and wherein up-regulation of the target gene is indicative of a leukemic disease state.

54. The method of claim 1, wherein the target gene is OSF-2os, and wherein up-regulation of the target gene is indicative of a leukemic disease state.

55. The method of claim 1, wherein the target gene is *Homo sapiens* proline synthetase, and wherein up-regulation of the target gene is indicative of a leukemic disease state.

56. The method of claim 1, wherein the target gene is hk02952 cDNA clone for KIAA0683, and wherein up-regulation of the target gene is indicative of a leukemic disease state.

57. The method of claim 1, wherein the target gene is wi24g10.x1 *Homo sapiens,* and wherein up-regulation of the target gene is indicative of a leukemic disease state.

58. The method of claim 1, wherein the target gene is Lysosomal enzyme deficient in Sanfilippo B syndrome, and wherein up-regulation of the target gene is indicative of a leukemic disease state.

59. The method of claim 1, wherein the target gene is CTP synthetase (AA 1-591), and wherein up-regulation of the target gene is indicative of a leukemic disease state.

60. The method of claim 1, wherein the target gene is human 5'-terminal region of UMK, and wherein up-regulation of the target gene is indicative of a leukemic disease state.

61. The method of claim 1, wherein the target gene is *Homo sapiens* chemokine exodus-1, and wherein up-regulation of the target gene is indicative of a leukemic disease state.

62. The method of claim 1, wherein the target gene is human GPI-H, and wherein up-regulation of the target gene is indicative of a leukemic disease state.

63. The method of claim 1, wherein the target gene is *Homo sapiens* RAMP1, and wherein up-regulation of the target gene is indicative of a leukemic disease state.

64. The method of claim 1, wherein the target gene is transforming growth factor-beta-2 precursor, and wherein up-regulation of the target gene is indicative of a leukemic disease state.

65. The method of claim 1, wherein the target gene is *Homo sapiens* KIAA0763 protein, and wherein up-regulation of the target gene is indicative of a leukemic disease state.

* * * * *

UNITED STATES PATENT AND TRADEMARK OFFICE
CERTIFICATE OF CORRECTION

PATENT NO. : 7,049,072 B2  Page 1 of 1
APPLICATION NO. : 10/263419
DATED : May 23, 2006
INVENTOR(S) : Beerelli Seshi It is certified that error appears in the above-identified patent and that said Letters Patent is hereby corrected as shown below:

Column 1,
Line 15, "09/914,508, filed Nov. 7, 2001," should read
--09/914,508, filed Aug. 28, 2001,--.

Column 42,
Line 17, "separation of MPG" should read --separation of MPC--.

Column 48,
Line 59, "A)-Untreated" should read --A) Untreated--.

Column 50,
Line 11, "from SMPC)." should read --from sMPC).--.

Column 51,
Line 49, "and SMPC)." should read --and sMPC).--.

Column 87,
Line 65, "Blood 79Q 2370-7." should read --Blood 79, 2370-7.--.

Column 90,
Line 45, "HEMATOLOGY: asic" should read --HEMATOLOGY: Basic--.

Signed and Sealed this

Twentieth Day of February, 2007

JON W. DUDAS
*Director of the United States Patent and Trademark Office*